US010000808B2

(12) United States Patent
Barrie et al.

(10) Patent No.: US 10,000,808 B2
(45) Date of Patent: Jun. 19, 2018

(54) METHODS OF DETECTING CERVICAL CANCER

(71) Applicant: Cepheid, Sunnyvale, CA (US)

(72) Inventors: Cecilia Svanholm Barrie, Bromma (SE); Olivier Delfour, Caraman (FR); David H. Persing, San Martin, VA (US)

(73) Assignee: Cepheid, Sunnyvale, CA (US)

( * ) Notice: Subject to any disclaimer, the term of this patent is extended or adjusted under 35 U.S.C. 154(b) by 605 days.

(21) Appl. No.: 14/445,417

(22) Filed: Jul. 29, 2014

(65) Prior Publication Data

US 2015/0051103 A1  Feb. 19, 2015

Related U.S. Application Data

(63) Continuation of application No. 13/658,276, filed on Oct. 23, 2012, now abandoned, which is a continuation of application No. 12/715,179, filed on Mar. 1, 2010, now abandoned, which is a continuation-in-part of application No. 12/688,784, filed on Jan. 15, 2010.

(60) Provisional application No. 61/145,439, filed on Jan. 16, 2009, provisional application No. 61/165,835, filed on Apr. 1, 2009.

(51) Int. Cl.
 *C12Q 1/68* (2018.01)

(52) U.S. Cl.
 CPC ......... *C12Q 1/6883* (2013.01); *C12Q 1/6886* (2013.01); *C12Q 2600/118* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 5,846,704 A | 12/1998 | Maertens et al. | |
| 6,706,867 B1 | 3/2004 | Lorenz | |
| 7,709,616 B2 | 5/2010 | Bentwich et al. | |
| 7,723,055 B2 | 5/2010 | Jones et al. | |
| 7,825,229 B2 | 11/2010 | Bentwich et al. | |
| 7,943,318 B2 | 5/2011 | Croce et al. | |
| 2005/0075492 A1 | 4/2005 | Chen et al. | |
| 2005/0208496 A1 | 9/2005 | Ohtani | |
| 2005/0221370 A1 | 10/2005 | Hodge | |
| 2006/0105360 A1 | 5/2006 | Croce et al. | |
| 2006/0134663 A1 | 6/2006 | Harkin et al. | |
| 2008/0026951 A1 | 1/2008 | Brown et al. | |
| 2008/0193943 A1 | 8/2008 | Murray | |
| 2008/0286763 A1 | 11/2008 | Russworm et al. | |
| 2010/0227325 A1 | 9/2010 | Vilanova et al. | |
| 2010/0233704 A1 | 9/2010 | Michot et al. | |
| 2010/0240049 A1 | 9/2010 | Svanholm Barrie et al. | |
| 2010/0305185 A1 | 12/2010 | Bjorck et al. | |
| 2011/0015080 A1 | 1/2011 | Golub et al. | |
| 2011/0053158 A1 | 3/2011 | Mambo et al. | |
| 2012/0184453 A1 | 7/2012 | Wang et al. | |
| 2012/0231970 A1 | 9/2012 | Nakagama et al. | |
| 2012/0244530 A1 | 9/2012 | Michot et al. | |
| 2013/0084343 A1 | 4/2013 | Vilanova et al. | |
| 2013/0102488 A1 | 4/2013 | Barrie et al. | |
| 2013/0157886 A1 | 6/2013 | Michot et al. | |

FOREIGN PATENT DOCUMENTS

| | | |
|---|---|---|
| EP | 1783645 | 5/2007 |
| WO | 99/47706 | 9/1999 |
| WO | WO 2005/098029 | 10/2005 |
| WO | WO 2005/116250 A2 | 12/2005 |
| WO | WO 2006/069584 | 7/2006 |
| WO | WO 2007/054520 | 5/2007 |
| WO | 2007081196 | 7/2007 |
| WO | WO 2007/073737 | 7/2007 |
| WO | WO 2008/040355 | 4/2008 |
| WO | WO 2008/046911 | 4/2008 |
| WO | WO 2008/074328 | 6/2008 |
| WO | WO 2008/115387 A2 | 9/2008 |
| WO | WO 2008/125883 A1 | 10/2008 |
| WO | WO 2009/036332 | 3/2009 |
| WO | WO 2009/100430 | 8/2009 |
| WO | 2010088668 | 8/2010 |
| WO | 2010112316 | 10/2010 |

OTHER PUBLICATIONS

Muralidhar et al. (J Pathol 2007; 212:368-377; cited in IDS).*
NCBI GEO record describing Platform GPL7766, including full miRNA_LIST table accessed from http://www.ncbi.nlm.nih.gov/geo on Jul. 10, 2013 (14 pages)(cited in IDS).*
Saetre (Molecular Brain Research. 2004. 126: 198-206).*
Liu et al (Clinical Immunology. 2004. 112: 225-230).*
Coleman (Drug Discovery Today. 2003. 8: 233-235).*
Applied Biosystems, TaqMan MicroRNA Assays and Arrays Product Bulletin, 2011, 4 pages.
Baraniskin et al, Circulating U2 small nuclear RNA fragments as a novel diagnostic biomarker for pancreatic colorectal adenocarcinoma, Int J Cancer (2012), Accepted Article, doi:10.1002/ijc.27791, 57 pages.
Butnor, Avoiding Underdiagnosis, Overdiagnosis, and Misdiagnosis of Lung Carcinoma, Arch Pathol Lab Med (2008), 132:1118-1132.
Castle et all, Digital Genome-Wide ncRNA Expression, Including SnoRNAs, across 11 Human Tissues Using PolyA-Neutral Amplification, PLoS One, 2010, 5(7):e11779, 9 pages.
Coleman, "Of mouse and man—what is the value of the mouse in predicting gene expression in humans," DDT, 2003, 8(6):233-235.
Dermer, "Another Anniversary for the War on Cancer," Biotechnology, 1994, 12:320.
Dziadziuszko et al, Advances in Genomic and Proteomic Studies of Non-Small-Cell Lung Cancer: Clinical and Translational Research Perspective, Clinical Lung Cancer (2008), 9(2):78-84.

(Continued)

*Primary Examiner* — Juliet C Switzer
(74) *Attorney, Agent, or Firm* — McNeill Baur PLLC

(57) ABSTRACT

Methods of detecting cervical dysplasia, such as cervical dysplasia likely to progress to carcinoma in a sample of human cervical cells, are provided. Methods of detecting changes in expression of one or more microRNAs or mRNAs associated with cervical dysplasia or cervical cancer are also provided. Compositions and kits are also provided.

6 Claims, 5 Drawing Sheets

(56) References Cited

OTHER PUBLICATIONS

Fabbri et al., "MicroRNA-29 family reverts aberrant methylation in lung cancer by targeting DNA methyltransferases 3A and 3B," PNAS, 2007, 104(40):15805-15810.
Field et al, Lung Cancer Screening: the way forward, British Journal of Cancer (2008), 99:557-562.
Gao et al., MiR-21 overexpression in human primary squamous cell lung carcinoma is associate with poor patient prognosis,: J Cancer Res Clin Oncol, 2011, 137:557-566.
Guo et al, Cross-Mapping Events in miRNAs Reveal Potential miRNA-Mimics and Evolutionary Implications, PLoS One (2011), 6: e20517, 7 pages.
Heegaard et al, Circulating microRNA Expression Profiles in Early Stage Non-Small Cell Lung Cancer, International Journal of Cancer, doi:10.1002/ijc.26153, Aug. 26, 2011; 26 pages.
Kotake et al. Splicing factor SF3b as a target of the antitumor natural product pladeinolide, Nature Chem. Biol. (2007), 3(9):570-575.
Langenberger et al., Identification and Classification of Small RNAs in Transcriptome Sequence Data, Pacific Symposium on Biocurnuting, 2010, 15:80-87.
Liu et al., "Comparision of differentially expressed genes in T lymphocytes between human autoimmune disease and murine models of autoimmune disease," Clin Immunol, 2004, 112:225-230.
Mascaux et al, Evolution of microRNAs expression during human brochial squamous carcinogenesis, ERJ Express (2008), doi: 10.1183/09031936.00084108; 23 pages.
Nallar et al., GRIM-1, a Novel Growth Suppressor, Inhibits rRNA Maturation by Suppressing Small Nucleolar RNAs, PLoS One, 2011, 6(9):e24082, 12 pages.
Palmer et al., "Cell-type specific gene expression profiles of leukocytes in human peripheral blood," BMC Genomics, 2006, 7:115-129.
Patnaik et al., MicroRNA Expression Profiles of Whole Blood in Lung Adenocarcinoma, PLoS One, 2012, 7(9): e46045, 12 pages.
Saetre et al., "From wild wolf to domestic dog: gene expression changes in the brain," Molecular Brain Research, 2004, 126:198-206.
Volinia et al., "A microRNA expression signature of human solid tumors defines cancer gene targets," PNAS, 2006, 103(7):2257-2261.
Volinia et al., "A microRNA expression signature of human solid tumors defines cancer gene targets, Supporting information" PNAS, 2006, doi:10.1073/pnas.0510565103, 24 pages.
Wang et al., Comparing the MicroRNA Spectrum between Serum and Plasma, PLoS One, 2012, 7(7):e41561, 9 pages.
Watahiki et al, MicroRNAs Associated with Metastatic Prostate Cancer, PLoS One (2011), 6(9):e24950, 13 pages.
Weiss et al, EGFR regulation by microRNA in lung cancer: correlation with clinical response and survival to gefitinib and EGFR expression in cell lines, Annals of Oncology (2008), 19:1053-159.
Wulfken et al, MicroRNAs in Renal Cell Carcinoma: Diagnostic Implications of Serum miR-1233 Levels, PLoS One, 2011, 6(9):e25787, 7 pages.
Zhou et al., Integrating microRNAs into a system biology approach to acute lung injury, Transl Res, 2011, 157 (4):180-190.
Zuker, Mfold web server for nucleic acid folding and hybridization prediction, Nucleic Acids Research (2003), 31:3406-3415.
SEQ ID No. 68404 from US2006/0134663, published Jun. 22, 2006; 2 pages.
SEQ ID No. 115101 from US2006/0134663, published Jun. 22, 2006; 1 page.
SEQ ID No. 2501 from US2007/0050146, published Mar. 1, 2007; 1 page.
International Search Report and Written Opinion dated Sep. 7, 2010, for Application No. PCT/US2010/025446, filed Feb. 25, 2010; 17 pages.
International Search Report and Written Opinion dated Jul. 11, 2012, for Application No. PCT/US2012/022756, filed Jan. 26, 2012; 21 pages.
International Search Report and Written Opinion dated Feb. 11, 2013, for Application No. PCT/US2012/055457, filed Sep. 14, 2012; 19 pages.
International Search Report and Written Opinion dated Jul. 20, 2010, for Application No. PCT/US2010/022885, filed Feb. 2, 2010; 17 pages.
GenBank BJ069802.1. NIBB Mochii normalized Xenopus tailbud library Xenopus laevis cDNA clone XL054k04 5-, mRNA sequence. Sep. 29, 2003, 1 page.
GenBank: CR759927.12. Zebrafish DNA sequence from clone CH211-196C10 in linkage group 8, complete sequence. Jan. 29, 2005, 39 pages.
GenBank: AC116208.5. Rattus norvegicus clone CH230-129C14, Working Draft Sequence, 2 unordered pieces. May 13, 2003, 44 pages.
Gen Bank: CW684880.1. OG_BBa0042M07.r OG_BBa Oryza glaberrima genomic clone OG_BBa0042M07 3-, genomic survey sequence. Nov. 1, 2004, 1 page.
GenBank: FC748656.1. CBBI4053.rev CBBI Lottia gigantea 26h, 37h, 61h larvae (L) Lottia gigantea cDNA clone CBBI4053 3-, mRNA sequence. Dec. 19, 2007, 1 page.
Palma et al. MicroRNAs are exported from malignant cells in customized particles, Nucleic Acids Research, 2012, 40 (18): 9125-9138, 14 pages.
Boyd, Everything you wanted to know about small RNA but were afraid to ask, Laboratory Investigation (2008), 88: 569-578.
Chen et al, Real-time quantification of microRNAs by stern-loop RT-PCR, Nucleic Acids Research (2005) 33(20): e179.
Dalmay, MicroRNAs and cancer, Journal of Internal Medicine (2008) 263: 366-375.
Griffiths-Jones et al, miRBase: microRNA sequences, targets and gene nomenclature, Nucleic Acids Research (2006), 34:D140-D144.
Griffiths-Jones et al, miRBase: tools for microRNA genomics, Nucleic Acids Research (2008), 36:D154-D158.
Gusev et al, MicroRNA expression profiling in cancer from a bioinformatics prospective, Expert Review of Molecular Diagnostics (2007), 7(6): 787-792.
Hammond, microRNA detection comes of age, Nature Methods (2006), (3)1: 12-13.
Liu et al, Expression profiling of microRNA using oligo DNA arrays, Science Direct (2008), Methods 44: 22-30.
Mora et al, Enzymatic microRNA detection in microliter plates with DNA dendrimers, BioTechniques (2006), 41:420-424.
Mora et al, High-sensitivity detection methods for low-abundance RNA species: applications for functional genomics research, Expert Review of Molecular Diagnostics (2007), 7(6): 775-785.
Nelson et al, Microarray-based, high-throughput gene expression profiling of microRNAs, Nature Methods (2004), 1 (2): 1-7.
Chang et al, miR-122, a Mammalian Liver-Specific microRNA, is Processed from her mRNA and May Downregulate the High Affinity Cationic Amino Acid Transporter CAT-1, RNA Biology (2004), 1(2): 106-113.
Varallyay et al, MicroRNA detection by northern blotting using locked nucleic acid probes, Nature Protocols (2008), 3(2): 190-196.
Wark et al, Multiplexed Detection Methods for Profiling MicroRNA Expression in Biological Samples, Angew. Chem. Int. Ed. (2008) 47: 644-652.
Wilkinson, A rapid and convenient method for isolation of nuclear, cytoplasmic and total cellular RNA, Nucleic Acids Research (1988), 16(22): 10934.
Zuker, Mfold web server for nucleic acid folding and hybridization prediction, Nucleic Acids Research (2003), 31 (13):3406-3415.
Boulet, Biomarkers in cervical screening: quantitative reverse transcriptase PCR analysis of p16INK4a expression, European Journal of Cancer Prevention (2010), 19:35-41.
Muralidhar et al, Global microRNA profiles in cervical squamous cell carcinoma depend on Drosha expression levels, Journal of Pathology (2007), 212: 368-377.

(56) References Cited

OTHER PUBLICATIONS

Muralidhar et al, Erratum: Global microRNA profiles in cervical squamous cell carcinoma depend on Drosha expression levels, Journal of Pathology (2007), 212: i, 1 page.

Jay et al, miRNA Profiling for Diagnosis and Prognosis of Human Cancer, DNA and Cell Biology (2007), 26(5): 293-300.

Lee et al, Altered MicroRNA Expression in Cervical Carcinomas, Clin Cancer Res (2008), 14(9) 2535-2542.

Lim et al, Mustering the micromanagers, Nature Biotechnology (2007), 25(9); 996-997.

Lui et al, Patterns of Known and Novel Small RNAs in Human Cervical Cancer, Cancer Res (2007), 67(13): 6031-6043, with supplementary data, 28 total pages.

Martinez et al, Human Papillomavirus type 16 reduces the expression of microRNA-218 in cervical carcinoma cells, Oncogene (2008), 27(18): 2575-2582.

Pagliarulo et al, Sensitivity and reproducibility of standardized-competitive RT-PCR for transcript quantification and its comparison with real time RT-PCR, Molecular Cancer (2004), 3:5, 11 pages.

Wang et al, Aberrant Expression of Oncogenic and Tumor-Suppressive MicroRNAs in Cervical Cancer is Required for Cancer Cell Growth (2008), PLoS One 3(7): e2557. doi:10.1371/journal.pone. 0002557, 11 pages.

Zhai et al, Gene Expression Analysis of Preinvasive and Invasive Cervical Squamous Cell Carcinomas Identifies HOXC10 as a Key Mediator of Invasion, Cancer Res. (2007), 67(21); 10163-10172.

Zhang et al, MicroRNAs as oncogenes and tumor suppressors, Developmental Biology 302 (2007), 1-12.

International Search Report and the Written Opinion; PCT International Application No. PCT/US2010/021274; dated Mar. 15, 2011, 20 pages.

Brameier et al., "Human box C/D snoRNAs with miRNA like functions: expanding the range of regulatory RNAs," Nucleic Acid Res., 2011, 39(2):675-686.

Burroughs et al., "Deep-sequencing of human argonaute-associated small RNAs provides insight into miRNA sorting and reveals argonaute association with RNA fragments of diverse origin," RNA Biol., 2011, 8:158-177.

Castoldi et al., "miChip: a microarray platform for expression profiling of microRNAs based on locked nucleic acid (LNA) oligonucleotide capture probes," Methods, 2007, 43(2):146-52.

Haussecker et al., "Human tRNA-derived small RNAs in the global regulation of RNA silencing," RNA, 2010, 16:673-695.

Lee et al., "A novel class of small RNAs: tRNA-derived RNA fragments (tRFs)," Genes Devel., 2009, 23:2639-2649.

Liu et al., "An oligonucleotide microchip for genome-wide microRNA profiling in human and mouse tissues," PNAS, 2004, 101(26):9740-4.

Miyoshi et al., "Many ways to generate microRNA-like small RNAs: non-canonical pathways for microRNA production," Mol Genet Genomics, 2010, 284(2):95-103.

NEB Catalog (1998/1999), pp. 121, 284 (3 pages).

NCBI GEO record describing Platform GPL7766, including full miRNA_LIST table accessed from http://www.ncbi.nlm.nih.gov/geo on Jul. 10, 2013 (14 pages).

Pederson, "Regulatory RNAs derived from transfer RNA?," RNA, 2010, 16:1865-1869.

Reese et al., "Identification of Novel MicroRNA-Like Molecules Generated from Herpesvirus and Host tRNA Transcripts," J Virol., 2010, 84(19):10344-10353.

Rothstein et al., "Chronic inhibition of superoxide dismutase produces apoptotic death of spinal neurons," PNAS, 1994, 91(10):4155-9.

Speicher et al., "Karyotyping human chromosomes by combinatorial multi-fluor Fish," Nat Gen., 1996, 12(4):368-75.

Yang & Lai, "Dicer-independent, Ago2-mediated microRNA biogenesis in vertebrates," Cell Cycle, 2010, 9:4455-4460.

* cited by examiner

SEQUENCE LISTING

```
<160> NUMBER OF SEQ ID NOS: 409

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tttcctttcc tccctccac acccatgac tccccacact tgag                    44

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ggaaagtcag cccccagcgc cccccggagt tcttgg                           36

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ctcctcctcc ccgtctttgg ataccaaaca ctggac                           36

<210> SEQ ID NO 4
<211> LENGTH: 34
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 4
ctcagcccca gctggagaat ttttcccctc atta                                   34

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ttcttgccct ccaatccccg ggctccacca gcc                                    33

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gctccctctc tggttggacc tcacccaaag at                                     32

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
aatcatccat ttcatccgca tctccctctt ggcccttgc                              40

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
aaagtctcgc tctctgcccc tca                                               23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tcggccctgc ctcctcctcc t                                                 21

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 10
taaagagact tcctccactg ccagagatct                                        30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tcagcgcaac aagccccgca gtcacccctc t                                      31

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
aaatggctcc tttccccttt ccctccaccg                                        30

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cgtctccctc cctcatgtgc                                                   20

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
acaggctact ttcagcaaat atgtccatcc t                                      31

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cccagaagac atcagacaga gttgtttctt ctccctcta                              39

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 16
gccctctggc ccctgcctaa ttggctgc                                          28

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
catttttccc cttccttcct ctatatcagc aa                                     32

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gattccagcc ccttccccc                                                    19

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
cattaacccc cattatcaca gcacgcccca ttc                                    33

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
gattccactt ttcttaatga ctttcccctc ct                                     32

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
gccccgcccc acctttcggg gctcacctgg c                                      31

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 22
gggttgcctc taatgtggta atagatgtca tt                                   32

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ccctcctttc cccacctcag t                                               21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
ctcagctgtt cccggtgcca g                                               21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
attaatcctt ctctcccctc tg                                              22

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gcccctgcca gaatcctcta acagctctaa ttgg                                 34

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
accgcgacat agcctcgccc cc                                              22

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
```
ctcgcaaagg atctccttca tccctcccca                                30

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ccctctctgc ctctctcatc accaataaca gac                            33

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cccagctaca cctccacgca                                           20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
atcagggtat cctctcccca                                           20

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aaataatcat tccaaatggt tctccctgct atgattcac                      39

<210> SEQ ID NO 33
<211> LENGTH: 55
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
cccgagcccg gcgccctgtg ttgtgctccg ctctccggga aatgccatca ctaat    55

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34

```
gccaagcttg aacctctcc ctgccagcat cac                                    33
```

```
<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
tctggagtac cacctgtttt tcccccact                                        29

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
gtgatgcaga ggacttcctg ctccaggtct c                                     31

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
aaggctgtcc ctcaccagac ttccccaccc ct                                    32

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
gcggtcccgc ggcgccccgc ct                                               22

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
catcaccttc cttctcctcc a                                                21

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cactgcaccg cgtcccgtcc ct                                               22
```

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
ctgcgattcc tccctctact gt                                              22

<210> SEQ ID NO 42
<211> LENGTH: 94
<212> TYPE: DNA
<213> ORGANISM: Homo sapiens

<400> SEQUENCE: 42
ctcaagtgtg gggagtcatg gggtgtggag gggaggaaag gaaaggtatt ttgtttcttt     60
gtctatacat ttcctagatt tctatgcagt tggg                                 94

<210> SEQ ID NO 43
<211> LENGTH: 69
<212> TYPE: DNA
<213> ORGANISM: Homo sapiens

<400> SEQUENCE: 43
ggggacgtgg cccctccccc ccggagcggg actccaagaa ctccgggggg cgctggggc      60 tgactttcc                                                             69

<210> SEQ ID NO 44
<211> LENGTH: 73
<212> TYPE: DNA
<213> ORGANISM: Homo sapiens

<400> SEQUENCE: 44
cttttctctc tgctgggaa accttgcttg acttcatgtc cagtgtttgg tatccaaaga      60
cggggaggag gag                                                        73

<210> SEQ ID NO 45
<211> LENGTH: 73
<212> TYPE: DNA
<213> ORGANISM: Homo sapiens

<400> SEQUENCE: 45
ctcagtatct tcagcttggg aaactgacct cgttaatttt aatgagggga aaattctcc      60 agctggggct gag                                                        73

<210> SEQ ID NO 46
<211> LENGTH: 87
<212> TYPE: DNA
<213> ORGANISM: Homo sapiens

<400> SEQUENCE: 46
ggaagggcac tgtctctctg attcccaggg cctgtcattt cccgagggct ggtggagccc     60
ggggattgga gggcaagaag cccagcc                                         87

<210> SEQ ID NO 47
<211> LENGTH: 74
<212> TYPE: DNA
<213> ORGANISM: Homo sapiens

```
<400> SEQUENCE: 47
gccacctttc atggtgagga tgcctgccac cttcaggatc acatctttgg gtgaggtcca      60
accagagagg gagc                                                       74

<210> SEQ ID NO 48
<211> LENGTH: 84
<212> TYPE: DNA
<213> ORGANISM: Homo sapiens

<400> SEQUENCE: 48
gcaaggggcc aagagggaga tgcggatgaa atggatgatt taatgggtca tctctcctgt      60
agttaatttc tctagatctc ttgt                                            84

<210> SEQ ID NO 49
<211> LENGTH: 94
<212> TYPE: DNA
<213> ORGANISM: Homo sapiens

<400> SEQUENCE: 49
ataaaggaag ttaggctgag gggcagagag cgagactttt ctattttcca aaagctcggt      60
ctgaggcccc tcagtcttgc ttcctaaccc gcgc                                 94

<210> SEQ ID NO 50
<211> LENGTH: 84
<212> TYPE: DNA
<213> ORGANISM: Homo sapiens

<400> SEQUENCE: 50
gcttggtgag aggaggagga ggcagggccg accgccaccc gcctgtctgc catctggtcc      60
ccttcccctc cctcctctca ttgc                                            84

<210> SEQ ID NO 51
<211> LENGTH: 70
<212> TYPE: DNA
<213> ORGANISM: Homo sapiens

<400> SEQUENCE: 51
tgaagaattt cttctggatg actgaccaag aggctattca agatctctgg cagtggagga      60
agtctcttta                                                            70

<210> SEQ ID NO 52
<211> LENGTH: 75
<212> TYPE: DNA
<213> ORGANISM: Homo sapiens

<400> SEQUENCE: 52 agagggggtga ctgcggggct tgttgcgctg aagatttaca atgtacttct tgcaggcggc     60
tcagcaaccc cctct                                                      75

<210> SEQ ID NO 53
<211> LENGTH: 75
<212> TYPE: DNA
<213> ORGANISM: Homo sapiens

<400> SEQUENCE: 53
cggtggaggg aaaggggaaa ggagccattt tctgctgcac atcagtcagt gcctgcgccc      60
tccctccctc cgccg                                                      75
```

<210> SEQ ID NO 54
<211> LENGTH: 78
<212> TYPE: DNA
<213> ORGANISM: Homo sapiens

<400> SEQUENCE: 54
tgctggaggt aagggttttc tgaagcctgg tgccatggcc acatgtgcac atgagggagg      60
gagacgctga ggctagca                                                   78

<210> SEQ ID NO 55
<211> LENGTH: 71
<212> TYPE: DNA
<213> ORGANISM: Homo sapiens

<400> SEQUENCE: 55
aggatggaca tatttgctga aagtagcctg tgcattaatt ggttatggaa gtttaaaaat      60
ggtgtcctcc t                                                          71

<210> SEQ ID NO 56
<211> LENGTH: 78
<212> TYPE: DNA
<213> ORGANISM: Homo sapiens

<400> SEQUENCE: 56
tagagggaga agaaacaact ctgtctgatg tcttctggga tggccttaat acagatagca      60
ttgtctcttc catttctg                                                   78

<210> SEQ ID NO 57
<211> LENGTH: 70
<212> TYPE: DNA
<213> ORGANISM: Homo sapiens

<400> SEQUENCE: 57
gcccagttaa ttggtctctc aacctacatt agctgttgca ttgcagccaa ttaggcaggg      60
gccagagggc                                                            70

<210> SEQ ID NO 58
<211> LENGTH: 80
<212> TYPE: DNA
<213> ORGANISM: Homo sapiens

<400> SEQUENCE: 58
gtctttgctg atatagagga aggaagggga aaaatgagcg cattagttct cttttattaa      60
aagagttatt tcagcatgac                                                 80

<210> SEQ ID NO 59
<211> LENGTH: 75
<212> TYPE: DNA
<213> ORGANISM: Homo sapiens

<400> SEQUENCE: 59
gggggaaggg gctggaatca tcgtgggttg gaacagttaa aggaacctct gttcagcccc      60
agccccaagg ctccc                                                      75

<210> SEQ ID NO 60
<211> LENGTH: 89
<212> TYPE: DNA
<213> ORGANISM: Homo sapiens

<400> SEQUENCE: 60

```
gccatgggcc tccatagttt cctgtagccc ccttggttcc caagaatagt tttggaatgg    60
ggcgtgctgt gataatgggg gttaatggt                                      89

<210> SEQ ID NO 61
<211> LENGTH: 83
<212> TYPE: DNA
<213> ORGANISM: Homo sapiens

<400> SEQUENCE: 61
gattcatcta ttcttttcct ccttcttcaa agataactct gtaagcactt aaggagggga    60
aagtcattaa gaaaagtgga atc                                            83

<210> SEQ ID NO 62
<211> LENGTH: 74
<212> TYPE: DNA
<213> ORGANISM: Homo sapiens

<400> SEQUENCE: 62
agcagccagg tgagccccga aaggtggggc ggggcagggg cgctcccagc cccaccccgg    60
gatctggtga cgct                                                      74

<210> SEQ ID NO 63
<211> LENGTH: 84
<212> TYPE: DNA
<213> ORGANISM: Homo sapiens

<400> SEQUENCE: 63
aatgacatct attaccacat tagaggcaac ccataacaat cccttataga atgtttgtct    60
caattttggt tatttaatgt catt                                           84

<210> SEQ ID NO 64
<211> LENGTH: 87
<212> TYPE: DNA
<213> ORGANISM: Homo sapiens

<400> SEQUENCE: 64
ccctcccagt tccatagca actgggctgt agcagccaga acttgattga gcccagcagt    60
ggcccgactg aggtggggaa aggaggg                                        87

<210> SEQ ID NO 65
<211> LENGTH: 71
<212> TYPE: DNA
<213> ORGANISM: Homo sapiens

<400> SEQUENCE: 65
caaattacat ctgtttatgc ttctatttgt tagacaatct ggcaccggga acagctgagc    60
agaaggattt g                                                         71

<210> SEQ ID NO 66
<211> LENGTH: 73
<212> TYPE: DNA
<213> ORGANISM: Homo sapiens

<400> SEQUENCE: 66
tgtcatttgt ccattttctc ttctgaccca gtggtattct gcaagatcag aggggagaga    60
aggattaatg tca                                                       73

<210> SEQ ID NO 67
```

```
<211> LENGTH: 90
<212> TYPE: DNA
<213> ORGANISM: Homo sapiens

<400> SEQUENCE: 67
gcctctgtgc gcatggatat aatcagcttt gataggcaga ggctgaggct gttttttccaa      60 ttagagctgt tagaggattc tggcaggggc                                         90

<210> SEQ ID NO 68
<211> LENGTH: 85
<212> TYPE: DNA
<213> ORGANISM: Homo sapiens

<400> SEQUENCE: 68
gggggcgagg ctatgtcgcg gtggcagccc ggatgggccg gcagggccgg gagtaacggg       60
acgtcgccgc ggagcttctt ccccc                                             85

<210> SEQ ID NO 69
<211> LENGTH: 73
<212> TYPE: DNA
<213> ORGANISM: Homo sapiens

<400> SEQUENCE: 69
ggcatttctt cttgtgtttc ctcttctcct cttctgggga gggatgaagg agatcctttg       60
cgagaggcat gtt                                                          73

<210> SEQ ID NO 70
<211> LENGTH: 88
<212> TYPE: DNA
<213> ORGANISM: Homo sapiens

<400> SEQUENCE: 70
tgctatctcg cctcacacat caacacacgt gccagacaga ttctgactgc aaagtctgtt       60
attggtgatg agagaggcag agagggca                                          88

<210> SEQ ID NO 71
<211> LENGTH: 86
<212> TYPE: DNA
<213> ORGANISM: Homo sapiens

<400> SEQUENCE: 71
cagctggcct ggtgccctgg tgcgtggagg tgtagctggg ctctgaccca gctcctcaaa       60
caggttccat atggccctcc cggctg                                            86

<210> SEQ ID NO 72
<211> LENGTH: 73
<212> TYPE: DNA
<213> ORGANISM: Homo sapiens

<400> SEQUENCE: 72
gtcaggctgc tgtattctct tacacagatg ccagtaagaa caaaggcatc acgtggggag       60 aggatacct gat                                                           73

<210> SEQ ID NO 73
<211> LENGTH: 98
<212> TYPE: DNA
<213> ORGANISM: Homo sapiens

<400> SEQUENCE: 73
aaataagcca ttccaaacca ttctctgatt tgctgtgagt ggcagaatca ttcaccgtgg       60
```
tgaatcatag cagggagaac catttggaat gattattt                                  98

<210> SEQ ID NO 74
<211> LENGTH: 107
<212> TYPE: DNA
<213> ORGANISM: Homo sapiens

<400> SEQUENCE: 74
cccggctcgg ccccgcgtct ctccagctcc tccggctcct tttagtgcat aaattagtga         60
tggcatttcc cggagagcgg agcacaacac agggcgccgg gctcggg                      107

<210> SEQ ID NO 75
<211> LENGTH: 85
<212> TYPE: DNA
<213> ORGANISM: Homo sapiens

<400> SEQUENCE: 75
ggcccagaag atgaaaagct gaagtcctttt cccttccagc tgaagccagg tgtgatgctg        60
gcagggagag gttccaagct tggcc                                               85

<210> SEQ ID NO 76
<211> LENGTH: 66
<212> TYPE: DNA
<213> ORGANISM: Homo sapiens

<400> SEQUENCE: 76
ttctgagata tgatctgttg gattctctac taccaaagtg ggggaaaaac aggtggtact         60
ccagaa                                                                    66

<210> SEQ ID NO 77
<211> LENGTH: 85
<212> TYPE: DNA
<213> ORGANISM: Homo sapiens

<400> SEQUENCE: 77
ggacactctg aaccccaagt ggaattccaa ctgccagttc ttcatccgag acctggagca         60
ggaagtcctc tgcatcactg tgttc                                               85

<210> SEQ ID NO 78
<211> LENGTH: 75
<212> TYPE: DNA
<213> ORGANISM: Homo sapiens

<400> SEQUENCE: 78
aggggtgggg aagtctggtg agggacagcc ttgagtcaaa ggatggtcac cgctccatgt         60
ggctgcccca cccct                                                          75

<210> SEQ ID NO 79
<211> LENGTH: 93
<212> TYPE: DNA
<213> ORGANISM: Homo sapiens

<400> SEQUENCE: 79
ccttccggcg tccaggcgg ggcgccgcgg gaccgccctc gtgtctgtgg cggtgggatc          60
ccgcggccgt gttttcctgg tggcccggcc atg                                      93

<210> SEQ ID NO 80
<211> LENGTH: 114
<212> TYPE: DNA

```
<213> ORGANISM: Homo sapiens

<400> SEQUENCE: 80
tttaggcgct gatgaaagtg gagttcagta gacagccctt ttcaagccct acgagaaact    60
ggggtttctg gaggagaagg aaggtgatga aggatctgtt ctcgtgagcc tgaa          114

<210> SEQ ID NO 81
<211> LENGTH: 96
<212> TYPE: DNA
<213> ORGANISM: Homo sapiens

<400> SEQUENCE: 81
cgggccccgg gcgggcggga gggacgggac gcggtgcagt gttgttttt cccccgccaa     60 tattgcactc gtcccggcct ccggcccccc cggccc                              96

<210> SEQ ID NO 82
<211> LENGTH: 98
<212> TYPE: DNA
<213> ORGANISM: Homo sapiens

<400> SEQUENCE: 82
tcaaggccac tgggacagta gagggaggaa tcgcagaaat cactccagga gcaactgaga    60
gaccttgctt ctactttacc aggtcctgct ggcccaga                            98

<210> SEQ ID NO 83
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cgcgcgucgc uuuaucuacu gu                                             22

<210> SEQ ID NO 84
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
uuaucguucg auaagucgcg uu                                             22

<210> SEQ ID NO 85
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gaaguuacua uguaggcaac cu                                             22

<210> SEQ ID NO 86
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 86
cgcgggacua auuguuaccg gg                                              22

<210> SEQ ID NO 87
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ucgcgucgaa cuccgcaacc ga                                              22

<210> SEQ ID NO 88
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
accgaacgcc guacccaucg gg                                              22

<210> SEQ ID NO 89
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89 cgagggruaac gacucucgug uc                                             22

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
ttgtaatacg actca                                                      15

<210> SEQ ID NO 91
<211> LENGTH: 23
<212> TYPE: RNA
<213> ORGANISM: Homo sapiens

<400> SEQUENCE: 91 ugagggcag agagcgagac uuu                                              23

<210> SEQ ID NO 92
<211> LENGTH: 22
<212> TYPE: RNA
<213> ORGANISM: Homo sapiens

<400> SEQUENCE: 92
aggcggggcg ccgcgggacc gc                                              22

<210> SEQ ID NO 93
```

```
<211> LENGTH: 21
<212> TYPE: RNA
<213> ORGANISM: Homo sapiens

<400> SEQUENCE: 93
uggaggagaa ggaaggugau g                                              21

<210> SEQ ID NO 94
<211> LENGTH: 22
<212> TYPE: RNA
<213> ORGANISM: Homo sapiens

<400> SEQUENCE: 94
agggacggga cgcggugcag ug                                             22

<210> SEQ ID NO 95
<211> LENGTH: 22
<212> TYPE: RNA
<213> ORGANISM: Homo sapiens

<400> SEQUENCE: 95
acaguagagg gaggaaucgc ag                                             22

<210> SEQ ID NO 96
<211> LENGTH: 23
<212> TYPE: RNA
<213> ORGANISM: Homo sapiens

<400> SEQUENCE: 96
ucuuugguua ucuagcugua uga                                            23

<210> SEQ ID NO 97
<211> LENGTH: 22
<212> TYPE: RNA
<213> ORGANISM: Homo sapiens

<400> SEQUENCE: 97
acaguagucu gcacauuggu ua                                             22

<210> SEQ ID NO 98
<211> LENGTH: 23
<212> TYPE: RNA
<213> ORGANISM: Homo sapiens

<400> SEQUENCE: 98
cccaguguuc agacuaccug uuc                                            23

<210> SEQ ID NO 99
<211> LENGTH: 23
<212> TYPE: RNA
<213> ORGANISM: Homo sapiens

<400> SEQUENCE: 99
cccaguguuu agacuaucug uuc                                            23

<210> SEQ ID NO 100
<211> LENGTH: 23
<212> TYPE: RNA
<213> ORGANISM: Homo sapiens

<400> SEQUENCE: 100
guccaguuuu cccaggaauc ccu                                            23
```

```
<210> SEQ ID NO 101
<211> LENGTH: 22
<212> TYPE: RNA
<213> ORGANISM: Homo sapiens

<400> SEQUENCE: 101
uuuggucccc uucaaccagc ug                                              22

<210> SEQ ID NO 102
<211> LENGTH: 22
<212> TYPE: RNA
<213> ORGANISM: Homo sapiens

<400> SEQUENCE: 102
uuuggucccc uucaaccagc ua                                              22

<210> SEQ ID NO 103
<211> LENGTH: 22
<212> TYPE: RNA
<213> ORGANISM: Homo sapiens

<400> SEQUENCE: 103
acagcaggca cagacaggca gu                                              22

<210> SEQ ID NO 104
<211> LENGTH: 22
<212> TYPE: RNA
<213> ORGANISM: Homo sapiens

<400> SEQUENCE: 104
cugaagcuca gagggcucug au                                              22

<210> SEQ ID NO 105
<211> LENGTH: 22
<212> TYPE: RNA
<213> ORGANISM: Homo sapiens

<400> SEQUENCE: 105 cugugcugu gacagcggcu ga                                               22

<210> SEQ ID NO 106
<211> LENGTH: 24
<212> TYPE: RNA
<213> ORGANISM: Homo sapiens

<400> SEQUENCE: 106
uuuggcaaug guagaacuca cacu                                            24

<210> SEQ ID NO 107
<211> LENGTH: 22
<212> TYPE: RNA
<213> ORGANISM: Homo sapiens

<400> SEQUENCE: 107
uauggcacug guagaauuca cu                                              22

<210> SEQ ID NO 108
<211> LENGTH: 22
<212> TYPE: RNA
<213> ORGANISM: Homo sapiens

<400> SEQUENCE: 108
ugagaacuga auuccauggg uu                                              22
```

```
<210> SEQ ID NO 109
<211> LENGTH: 22
<212> TYPE: RNA
<213> ORGANISM: Homo sapiens

<400> SEQUENCE: 109
uagcuuauca gacugauguu ga                                                  22

<210> SEQ ID NO 110
<211> LENGTH: 23
<212> TYPE: RNA
<213> ORGANISM: Homo sapiens

<400> SEQUENCE: 110
cagugcaaua guauugucaa agc                                                 23

<210> SEQ ID NO 111
<211> LENGTH: 23
<212> TYPE: RNA
<213> ORGANISM: Homo sapiens

<400> SEQUENCE: 111
uguaguguuu ccuacuuuau gga                                                 23

<210> SEQ ID NO 112
<211> LENGTH: 21
<212> TYPE: RNA
<213> ORGANISM: Homo sapiens

<400> SEQUENCE: 112
cauaaaguag aaagcacuac u                                                   21

<210> SEQ ID NO 113
<211> LENGTH: 22
<212> TYPE: RNA
<213> ORGANISM: Homo sapiens

<400> SEQUENCE: 113
uguaacagca acuccaugug ga                                                  22

<210> SEQ ID NO 114
<211> LENGTH: 21
<212> TYPE: RNA
<213> ORGANISM: Homo sapiens

<400> SEQUENCE: 114
augaccuaug aauugacaga c                                                   21

<210> SEQ ID NO 115
<211> LENGTH: 22
<212> TYPE: RNA
<213> ORGANISM: Homo sapiens

<400> SEQUENCE: 115
uauugcacau uacuaaguug ca                                                  22

<210> SEQ ID NO 116
<211> LENGTH: 22
<212> TYPE: RNA
<213> ORGANISM: Homo sapiens

<400> SEQUENCE: 116
auauaauaca accugcuaag ug                                                  22
```

```
<210> SEQ ID NO 117
<211> LENGTH: 22
<212> TYPE: RNA
<213> ORGANISM: Homo sapiens

<400> SEQUENCE: 117
ugugcgcagg gagaccucuc cc                                              22

<210> SEQ ID NO 118
<211> LENGTH: 23
<212> TYPE: RNA
<213> ORGANISM: Homo sapiens

<400> SEQUENCE: 118
cugggaucuc cggggucuug guu                                             23

<210> SEQ ID NO 119
<211> LENGTH: 23
<212> TYPE: RNA
<213> ORGANISM: Homo sapiens

<400> SEQUENCE: 119
aggaagcccu ggaggggcug gag                                             23

<210> SEQ ID NO 120
<211> LENGTH: 22
<212> TYPE: RNA
<213> ORGANISM: Homo sapiens

<400> SEQUENCE: 120
ugucuacuac uggagacacu gg                                              22

<210> SEQ ID NO 121
<211> LENGTH: 23
<212> TYPE: RNA
<213> ORGANISM: Homo sapiens

<400> SEQUENCE: 121
ccaguuaccg cuuccgcuac cgc                                             23

<210> SEQ ID NO 122
<211> LENGTH: 22
<212> TYPE: RNA
<213> ORGANISM: Homo sapiens

<400> SEQUENCE: 122
auccgcgcuc ugacucucug cc                                              22

<210> SEQ ID NO 123
<211> LENGTH: 22
<212> TYPE: RNA
<213> ORGANISM: Homo sapiens

<400> SEQUENCE: 123
ugcccuuaaa ggugaaccca gu                                              22

<210> SEQ ID NO 124
<211> LENGTH: 24
<212> TYPE: RNA
<213> ORGANISM: Homo sapiens

<400> SEQUENCE: 124
``` ugggagcug aggcucuggg ggug                                              24

<210> SEQ ID NO 125
<211> LENGTH: 21
<212> TYPE: RNA
<213> ORGANISM: Homo sapiens

<400> SEQUENCE: 125
aaggcagggc ccccgcuccc c                                                21

<210> SEQ ID NO 126
<211> LENGTH: 23
<212> TYPE: RNA
<213> ORGANISM: Homo sapiens

<400> SEQUENCE: 126
cacccggcug ugugcacaug ugc                                              23

<210> SEQ ID NO 127
<211> LENGTH: 22
<212> TYPE: RNA
<213> ORGANISM: Homo sapiens

<400> SEQUENCE: 127
ucuucucugu uuuggccaug ug                                               22

<210> SEQ ID NO 128
<211> LENGTH: 21
<212> TYPE: RNA
<213> ORGANISM: Homo sapiens

<400> SEQUENCE: 128
cugacuguug ccguccucca g                                                21

<210> SEQ ID NO 129
<211> LENGTH: 22
<212> TYPE: RNA
<213> ORGANISM: Homo sapiens

<400> SEQUENCE: 129
aaauuauugu acaucggaug ag                                               22

<210> SEQ ID NO 130
<211> LENGTH: 23
<212> TYPE: RNA
<213> ORGANISM: Homo sapiens

<400> SEQUENCE: 130
aaggagcuua caaucuagcu ggg                                              23

<210> SEQ ID NO 131
<211> LENGTH: 22
<212> TYPE: RNA
<213> ORGANISM: Homo sapiens

<400> SEQUENCE: 131
cggccccacg caccagggua ag                                               22

<210> SEQ ID NO 132
<211> LENGTH: 22
<212> TYPE: RNA
<213> ORGANISM: Homo sapiens

<400> SEQUENCE: 132
cugcccuggc ccgagggacc ga                                                22

<210> SEQ ID NO 133
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
ttctgctttc ccagagcctc accccctctt tt                                     32

<210> SEQ ID NO 134
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
acacctgtct ctccccagtg cttccgcccc tca                                    33

<210> SEQ ID NO 135
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
tccaacactg cctggcgctg ggctcttccc ca                                     32

<210> SEQ ID NO 136
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
ccacacttct aattggacaa agtgcctttc aaact                                  35

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
cagcctgcca ccgccgcttt tgaaagaagc acttca                                 36

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
cttctccttc ctccctgctc ccctcccact aatgccaaat                            40

<210> SEQ ID NO 139
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
ggctccctag tgaaaaaatg caaaatttgt ataat                                 35

<210> SEQ ID NO 140
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
ccactgccct cctgccgcat cctatgctcc tct                                   33

<210> SEQ ID NO 141
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
actcggcgct catcaaaaag ttccctgtcc g                                     31

<210> SEQ ID NO 142
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
tttgacattc agagcactgg gcagaaatca ca                                    32

<210> SEQ ID NO 143
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
gtcatagtta ctcccgccgt ttacccgcat ttc                                   33

<210> SEQ ID NO 144
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
gagatccaga cggccgtgcg cctgctgctg cct                                   33

<210> SEQ ID NO 145
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
acagcatcac atggattctg tgtccagtgg ccttagca                              38

<210> SEQ ID NO 146
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
acatgctcct gacactttct cttagtttct cgggctcc                              38

<210> SEQ ID NO 147
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
tccctttgtg ctgcccgagt gccttccccc tg                                    32

<210> SEQ ID NO 148
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
cgggtctccc gcttccccct cctgctccaa gg                                    32

<210> SEQ ID NO 149
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
ctcctcctcc ccgtctttgg ataccaaaca c                                     31

<210> SEQ ID NO 150
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
gactgagggt ttaaagaaga tggtgtccgc cgc                                   33

<210> SEQ ID NO 151
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
gacattcaga gcactgggca gaaatcacat g                                    31

<210> SEQ ID NO 152
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
catagttact cccgccgttt acccgtgctt c                                    31

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
tctgctccaa aaatccattt aatatattgt                                      30

<210> SEQ ID NO 154
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
gctccctctc tggttggacc tcacccaaa                                       29

<210> SEQ ID NO 155
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
ggagatccag acggccgagc gcctgctgct gccc                                 34

<210> SEQ ID NO 156
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
gcacacccgc tctccggccc gcgcccctg                                       29

```
<210> SEQ ID NO 157
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
aactagccgt ttccgtcacc ttcccctgcc ccc                                    33

<210> SEQ ID NO 158
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
acaatattta tccagggatg ggagtcagat gca                                    33

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
cgcagtgcac accctgagct acagcccctc                                        30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
agcctgtgcc tgccgctgtc tagtactggt                                        30

<210> SEQ ID NO 161
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
caagagccag cctgcactac cagtcccatg cca                                    33

<210> SEQ ID NO 162
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
ggaactgctt ctccttgctc cagtcattga ag                                     32

<210> SEQ ID NO 163
```

```
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 163
gatgctggcg tccgccgcag cctctcgccc catcccgg                                 38

<210> SEQ ID NO 164
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
aaaagccaat acattttcac tgtaccggcc ac                                       32

<210> SEQ ID NO 165
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
agactgctgt aaatgcggac aaagcgtccc tgc                                      33

<210> SEQ ID NO 166
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
tgcttccatc ccgccagttt ggtttcattg tactgacaac c                             41

<210> SEQ ID NO 167
<211> LENGTH: 40
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
ctgggtgagg tcccaccgtg gtgcgcttgg ctgtgccagc                               40

<210> SEQ ID NO 168
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
acctcagcct ccactgccct cctgccgcat cctat                                    35

<210> SEQ ID NO 169
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
ccctttaaga gcctctccgc gcgctgccg                                           29

<210> SEQ ID NO 170
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
ccgtggatgt caactcagct gccttccgcc                                          30

<210> SEQ ID NO 171
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
gcatgctaat tgtgccctgt tgtctttctt aaact                                    35

<210> SEQ ID NO 172
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
tgctctaccg gctatgacat taggtgtgac cg                                       32

<210> SEQ ID NO 173
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
gggaggagtc aggtgtgtgc tgtgggttgg gggaagac                                 38

<210> SEQ ID NO 174
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
gcgccctgtg ttgtgctccg ctctccggga aatgc                                    35

<210> SEQ ID NO 175
<211> LENGTH: 32
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 175
gggcccttcc cttcccccaa cattgagcct tg                                  32

<210> SEQ ID NO 176
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
ggacctatgg gcccttccct tcccccaaca ttg                                 33

<210> SEQ ID NO 177
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
tgaaagctga agtccagccc agccctct                                       28

<210> SEQ ID NO 178
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
ctgctgcctt ccttggttga ggggcctgag cacg                                34

<210> SEQ ID NO 179
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
tctccgccgg gccttcaccc tgccctgctc ttct                                34

<210> SEQ ID NO 180
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
ttaggaaatt ccatctcacc tgctccagtc c                                   31

<210> SEQ ID NO 181
<211> LENGTH: 35
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 181
gctccatgtc tcctcccctc cgcgaaagcc taaac                            35

<210> SEQ ID NO 182
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
agccttcctg tccctggcc cccgacctgc tcca                              34

<210> SEQ ID NO 183
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
cgcttcctta accatttttt tttttttaa ccac                              34

<210> SEQ ID NO 184
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 184
tggacgtctg aacagtcact gcctgcccca acct                             34

<210> SEQ ID NO 185
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
atgaccattt gtattagtat ctttttttt ttt                               33

<210> SEQ ID NO 186
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
ctgcggcaag tgcttctaca tccctgctcc aacaa                            35

<210> SEQ ID NO 187
<211> LENGTH: 34
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 187
taactcgcct gctgccccgg cggcctgccc gccg                                34

<210> SEQ ID NO 188
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
ctctgactcc ctcactcagt ctctctgctc cagc                                34

<210> SEQ ID NO 189
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
gggcccagtc ctcctcgtcc cccttcccac ctcgg                               35

<210> SEQ ID NO 190
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 190
gcagctccgc cagtctctgt gggcagggag aag                                 33

<210> SEQ ID NO 191
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
ggcccacccg ggggccgctc cccagcaccg acgcc                               35

<210> SEQ ID NO 192
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
tcctgagccg ccttcccctc ccgacctcag agccct                              36

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 193
acgtgccttc ctgactgtga gctccttgag agc                                    33

<210> SEQ ID NO 194
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
caatgaacca ctgaaccact catgcactga acc                                    33

<210> SEQ ID NO 195
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
ctgtagaccc cacactcagt ctctatagct a                                      31

<210> SEQ ID NO 196
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 196
cactccctgc tggcccccac ctcacctatg gtg                                    33

<210> SEQ ID NO 197
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
ccttctcttc tcccgtgctc ccaccctccc tcaggg                                 36

<210> SEQ ID NO 198
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
ggacccctgc cttccttgct gccacccttt gcaca                                  35

<210> SEQ ID NO 199
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
cccaagcgcc ccttcctccc tccttccctc ccg                                    33

<210> SEQ ID NO 200
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
cagtcacctc agattcctgt gccctctgcc ctgg                                   34

<210> SEQ ID NO 201
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
ccacccctcc cccacagccc agccccactc ac                                     32

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
ctcccttctt tcctcccgtc tt                                                22

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
tccatcatta cccggcagta tta                                               23

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
aactcagtaa tggtaacggt tt                                                22

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 205
gtagaaggga atcttgcata ag                                            22

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
gaggtttccc gtgtatgttt ca                                            22

<210> SEQ ID NO 207
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
tggaggcccc agcgaga                                                  17

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 208
cctgctccaa aaatccatt                                                19

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
tccctgatcc aaaaatcca                                                19

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
ccactgaacc acccatgc                                                 18

<210> SEQ ID NO 211
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
```
attgcgttcg aagtgtcgat gatcaat                                                27

<210> SEQ ID NO 212
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
ttgtaatacg actcatcggt tgcggagttc gacgcga                                     37

<210> SEQ ID NO 213
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
ttgtaatacg actcacccga tgggtacggc gttcggt                                     37

<210> SEQ ID NO 214
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 214
ttgtaatacg actcagacac gagagtcgtt accctcg                                     37

<210> SEQ ID NO 215
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
ttgtaatacg actcagtccg tctacgcgtc ggtacgc                                     37

<210> SEQ ID NO 216
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
ttgtaatacg actcaggccg tctacgcgtc ggtacgc                                     37

<210> SEQ ID NO 217
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
ttgtaatacg actcacccgg taacaattag acccgcg    37

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
gagctacagt gcttcatctc a    21

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
agggattcct gggaaaactg gac    23

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 220
cagactccgg tggaatgaag ga    22

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
tcaacatcag tctgataagc ta    22

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
agctatgcca gcatcttgcc t    21

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
tccataaagt aggaaacact aca    23

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
gccaatattt ctgtgctgct a                                          21

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
aacaatacaa cttactacct ca                                         22

<210> SEQ ID NO 226
<211> LENGTH: 87
<212> TYPE: DNA
<213> ORGANISM: Homo sapiens

<400> SEQUENCE: 226
tcccgcagcc ggtgactgga gcccacctct gcagagacaa aggttagaaa aagagggggt   60
gaggctctgg gaaagcagaa tgcgggg                                      87

<210> SEQ ID NO 227
<211> LENGTH: 95
<212> TYPE: DNA
<213> ORGANISM: Homo sapiens

<400> SEQUENCE: 227 tgagggcgg aagcactggg gagagacagg tgtgagcttc ccacgtggtg atcagctcac    60
acctgtcttg tgttcttggt attcacagac tctca                             95

<210> SEQ ID NO 228
<211> LENGTH: 110
<212> TYPE: DNA
<213> ORGANISM: Homo sapiens

<400> SEQUENCE: 228
aatgccagtg agtttgaaag gcactttgtc caattagaag tgtggagaaa tattcatcct   60
gtccatgaca aagatgaagt gcttctttca aaagcggcgg tggcaggctg             110

<210> SEQ ID NO 229
<211> LENGTH: 110
<212> TYPE: DNA
<213> ORGANISM: Homo sapiens

<400> SEQUENCE: 229
aatgccagtg agtttgaaag gcactttgtc caattagaag tgtggagaaa tattcatcct   60
gtccatgaca aagatgaagt gcttctttca aaagcggcgg tggcaggctg             110

<210> SEQ ID NO 230
<211> LENGTH: 83
<212> TYPE: DNA

```
<213> ORGANISM: Homo sapiens

<400> SEQUENCE: 230
cttctcttat tctccctgtt ttcatcctac ttttaagtaa taaatttggc attagtggga      60
ggggagcagg gaggaaggag aag                                              83

<210> SEQ ID NO 231
<211> LENGTH: 83
<212> TYPE: DNA
<213> ORGANISM: Homo sapiens

<400> SEQUENCE: 231
ggcccttagg aaattagagt gtgtttgaat ttcacaagta taatttaat tatacaaatt      60 ttgcattttt tcactaggga gcc                                              83

<210> SEQ ID NO 232
<211> LENGTH: 78
<212> TYPE: DNA
<213> ORGANISM: Homo sapiens

<400> SEQUENCE: 232
tggcctgacg tgaggaggag ggacttttcg aagttttata ggaaagtttc cgctttccag      60 tcccctccc ccgtccca                                                     78

<210> SEQ ID NO 233
<211> LENGTH: 77
<212> TYPE: DNA
<213> ORGANISM: Homo sapiens

<400> SEQUENCE: 233
gctggggttc atcggagaaa ctccctgcga tgagccacta gggtcacgga cagggaactt      60
tttgatgagc gccgagt                                                     77

<210> SEQ ID NO 234
<211> LENGTH: 84
<212> TYPE: DNA
<213> ORGANISM: Homo sapiens

<400> SEQUENCE: 234
gtgatgtgat ttctgcccag tgctctgaat gtcaaactga agaaattcag tgaaatgcgg      60
gtaaacggcg ggagtaacta tgac                                             84

<210> SEQ ID NO 235
<211> LENGTH: 84
<212> TYPE: DNA
<213> ORGANISM: Homo sapiens

<400> SEQUENCE: 235
gtgatgtgat ttctgcccag tgctctgaat gtcaaactga agaaattcag tgaaatgcgg      60
gtaaacggcg ggagtaacta tgac                                             84

<210> SEQ ID NO 236
<211> LENGTH: 84
<212> TYPE: DNA
<213> ORGANISM: Homo sapiens

<400> SEQUENCE: 236
ttccccaggc agcagcaggc gcacggccgt ctggatctcc ctggaggtga tggtcgagcg      60
cttgtcataa tgcgccaggc ggga                                             84
```

<210> SEQ ID NO 237
<211> LENGTH: 78
<212> TYPE: DNA
<213> ORGANISM: Homo sapiens

<400> SEQUENCE: 237
acagcggcat ggttcatgcc aaattccgaa gcaatcttcc tgctaaggcc actggacaca     60
gaatccatgt gatgctgt                                                   78

<210> SEQ ID NO 238
<211> LENGTH: 85
<212> TYPE: DNA
<213> ORGANISM: Homo sapiens

<400> SEQUENCE: 238
ggagcccgag aaactaagag aaagtgtcag gagcatgtta atcagactcg ttacactgta     60
acaataacgt ctctctcggg tctcc                                           85

<210> SEQ ID NO 239
<211> LENGTH: 85
<212> TYPE: DNA
<213> ORGANISM: Homo sapiens

<400> SEQUENCE: 239
ggtgtgtctg cctctctttc tgcccccta taccccttga ccccaggggg aaggcactcg      60
ggcagcacaa agggagcaga tgccc                                           85

<210> SEQ ID NO 240
<211> LENGTH: 75
<212> TYPE: DNA
<213> ORGANISM: Homo sapiens

<400> SEQUENCE: 240
gggtccgggt ctctaccgcg ccctcatgca ggaggccctt ggagcaggag ggggaagcgg     60
gagacccggc agccc                                                      75

<210> SEQ ID NO 241
<211> LENGTH: 73
<212> TYPE: DNA
<213> ORGANISM: Homo sapiens

<400> SEQUENCE: 241 cttttctct ctgctgggaa accttgcttg acttcatgtc cagtgtttgg tatccaaaga      60
cggggaggag gag                                                        73

<210> SEQ ID NO 242
<211> LENGTH: 80
<212> TYPE: DNA
<213> ORGANISM: Homo sapiens

<400> SEQUENCE: 242
catgtgattt ctgcccagtg ctctgaatgt caaagtgaag aaattcaatg aagcacgggt     60
aaacggcggg agtaactatg                                                 80

<210> SEQ ID NO 243
<211> LENGTH: 80
<212> TYPE: DNA
<213> ORGANISM: Homo sapiens -continued

```
<400> SEQUENCE: 243
catgtgattt ctgcccagtg ctctgaatgt caaagtgaag aaattcaatg aagcacgggt     60
aaacggcggg agtaactatg                                                 80

<210> SEQ ID NO 244
<211> LENGTH: 80
<212> TYPE: DNA
<213> ORGANISM: Homo sapiens

<400> SEQUENCE: 244
catgtgattt ctgcccagtg ctctgaatgt caaagtgaag aaattcaatg aagcacgggt     60
aaacggcggg agtaactatg                                                 80

<210> SEQ ID NO 245
<211> LENGTH: 74
<212> TYPE: DNA
<213> ORGANISM: Homo sapiens

<400> SEQUENCE: 245
tctgttttta tcagtttaat atatgataca tcttctatcc aaggacaata tattaaatgg     60 attttttggag caga                                                      74

<210> SEQ ID NO 246
<211> LENGTH: 74
<212> TYPE: DNA
<213> ORGANISM: Homo sapiens

<400> SEQUENCE: 246
gccacctttc atggtgagga tgcctgccac cttcaggatc acatctttgg gtgaggtcca     60
accagagagg gagc                                                       74

<210> SEQ ID NO 247
<211> LENGTH: 70
<212> TYPE: DNA
<213> ORGANISM: Homo sapiens

<400> SEQUENCE: 247
gggcagcagc aggcgctcgg ccgtctggat ctccctggag gtgatggtcg agcgcttgtt     60
gtaatgcgcc                                                            70

<210> SEQ ID NO 248
<211> LENGTH: 84
<212> TYPE: DNA
<213> ORGANISM: Homo sapiens

<400> SEQUENCE: 248
caggggcgcg ggccggagag cgggtgtgca aagtgggcgc agggccctgg ggccgcgccc     60
cttgctctgc cggctcgact cttg                                            84

<210> SEQ ID NO 249
<211> LENGTH: 84
<212> TYPE: DNA
<213> ORGANISM: Homo sapiens

<400> SEQUENCE: 249
gggggcaggg gaaggtgacg gaaacggcta gttacccaga attctctggg ggaaccagaa     60
aaatcggtta tctagaattc tccc                                            84
```

```
<210> SEQ ID NO 250
<211> LENGTH: 90
<212> TYPE: DNA
<213> ORGANISM: Homo sapiens

<400> SEQUENCE: 250
gcaattagaa tgcagggagg ttcagaagct atttaactgg gtgacccctg aggtcgctgc      60
atctgactcc catccctgga taaatattgt                                      90

<210> SEQ ID NO 251
<211> LENGTH: 81
<212> TYPE: DNA
<213> ORGANISM: Homo sapiens

<400> SEQUENCE: 251
gaggggctgt agctcagggt gtgcactgcg aggctggacc tgttgagtct gcagtggaca      60
tccatttagc ttcaggttgt c                                               81

<210> SEQ ID NO 252
<211> LENGTH: 79
<212> TYPE: DNA
<213> ORGANISM: Homo sapiens

<400> SEQUENCE: 252
agcctgttcc gtgctcgcta actataaact atctgattta tattcattaa ccagtactag      60
acagcggcag gcacaggct                                                  79

<210> SEQ ID NO 253
<211> LENGTH: 83
<212> TYPE: DNA
<213> ORGANISM: Homo sapiens

<400> SEQUENCE: 253
acagtaggta tagctggcat gggactggta gtgcaggctg gctcttggaa aggagtatgt      60
attccaggct ggttggctgc tgt                                             83

<210> SEQ ID NO 254
<211> LENGTH: 79
<212> TYPE: DNA
<213> ORGANISM: Homo sapiens

<400> SEQUENCE: 254
ggggctgcca tcctgctgtc cgtcatctgt gtggtgctgg tcacggcctt caatgactgg      60
agcaaggaga agcagttcc                                                  79

<210> SEQ ID NO 255
<211> LENGTH: 75
<212> TYPE: DNA
<213> ORGANISM: Homo sapiens

<400> SEQUENCE: 255
gatgccgggc gcccgccgca gccgctgccg ccggagcccg ggatggggcg agaggctgcg      60
gcggacgcca gcatc                                                      75

<210> SEQ ID NO 256
<211> LENGTH: 70
<212> TYPE: DNA
<213> ORGANISM: Homo sapiens

<400> SEQUENCE: 256
```

```
aagagcacaa acctttcatt ttgccgttta tttgtcttgt ggccggtaca gtgaaaatgt    60
attggctttt                                                          70

<210> SEQ ID NO 257
<211> LENGTH: 83
<212> TYPE: DNA
<213> ORGANISM: Homo sapiens

<400> SEQUENCE: 257
acagtaggta tagctggcat gggactggta gtgcaggctg gctcttggaa aggagtatgt    60
attccaggct ggttggctgc tgt                                           83

<210> SEQ ID NO 258
<211> LENGTH: 82
<212> TYPE: DNA
<213> ORGANISM: Homo sapiens

<400> SEQUENCE: 258
tgttttcatc ttgcttcttc atggtccatg atgccagctg aggttgtcag tacaatgaaa    60
ccaaactggc gggatggaag ca                                            82

<210> SEQ ID NO 259
<211> LENGTH: 85
<212> TYPE: DNA
<213> ORGANISM: Homo sapiens

<400> SEQUENCE: 259
ctgggaacaa tggggccatt gtgggaggat ggagtgcagc agactgctgg cacagccaag    60
cgcaccacgg tgggacctca cccag                                         85

<210> SEQ ID NO 260
<211> LENGTH: 87
<212> TYPE: DNA
<213> ORGANISM: Homo sapiens

<400> SEQUENCE: 260
gcttgtccta aaagatcttc cttctgtttc cctgggttta tccacttggt tggcctgatg    60
ggagcaggag gcggtgaggg ggcgggc                                       87

<210> SEQ ID NO 261
<211> LENGTH: 88
<212> TYPE: DNA
<213> ORGANISM: Homo sapiens

<400> SEQUENCE: 261
ctggcccatt ttcattctgc ataaaatttt aatggtctct ctggctgatc cgggacggca    60
gcgcgcggag aggctcttaa agggccag                                      88

<210> SEQ ID NO 262
<211> LENGTH: 78
<212> TYPE: DNA
<213> ORGANISM: Homo sapiens

<400> SEQUENCE: 262
ggatgcaacc gtggaagccg gtgccgttga ggatctgcca caggcggaag gcagctgagt    60
tgacatccac gggcatcc                                                 78

<210> SEQ ID NO 263
<211> LENGTH: 91
```

```
<212> TYPE: DNA
<213> ORGANISM: Homo sapiens

<400> SEQUENCE: 263
gaggctgctt aatgaggtgc cctttcaaa atgtcatctt aatctttat tagtttaaga    60 aagacaacag ggcacaatta gcatgcaact c                                 91

<210> SEQ ID NO 264
<211> LENGTH: 69
<212> TYPE: DNA
<213> ORGANISM: Homo sapiens

<400> SEQUENCE: 264
ggggacgtgg ccctccccc ccggagcggg actccaagaa ctccgggggg cgctggggc    60 tgactttcc                                                          69

<210> SEQ ID NO 265
<211> LENGTH: 87
<212> TYPE: DNA
<213> ORGANISM: Homo sapiens

<400> SEQUENCE: 265
gtcttccccc aacccacagc acacacctga ctcctccctt ccagggaaaa gacctcaggg    60
ctgctggtga gtcagaaata ggaagac                                       87

<210> SEQ ID NO 266
<211> LENGTH: 107
<212> TYPE: DNA
<213> ORGANISM: Homo sapiens

<400> SEQUENCE: 266
cccggctcgg ccccgcgtct ctccagctcc tccggctcct tttagtgcat aaattagtga    60
tggcatttcc cggagagcgg agcacaaacac agggcgccgg gctcggg                107

<210> SEQ ID NO 267
<211> LENGTH: 113
<212> TYPE: DNA
<213> ORGANISM: Homo sapiens

<400> SEQUENCE: 267
ggacctgggg gcttctctga cccttgaaca gcttatacta tgagaccttg ggaacctcct    60
ccatgcagac acacaaggct caatgttggg ggaagggaag ggcccatagg tcc           113

<210> SEQ ID NO 268
<211> LENGTH: 113
<212> TYPE: DNA
<213> ORGANISM: Homo sapiens

<400> SEQUENCE: 268
ggacctgggg gcttctctga cccttgaaca gcttatacta tgagaccttg ggaacctcct    60
ccatgcagac acacaaggct caatgttggg ggaagggaag ggcccatagg tcc           113

<210> SEQ ID NO 269
<211> LENGTH: 55
<212> TYPE: DNA
<213> ORGANISM: Homo sapiens

<400> SEQUENCE: 269
agagggctgg gctggacttc agctttcacc taggaaatga gtcttgctgc cctttt        55
```

<210> SEQ ID NO 270
<211> LENGTH: 89
<212> TYPE: DNA
<213> ORGANISM: Homo sapiens

<400> SEQUENCE: 270
ttcccacacg tgctcaggcc cctcaaccaa ggaaggcagc aggcccactg gcctccttat    60
tcagaggggc tgcactgcac cctagggag                                      89

<210> SEQ ID NO 271
<211> LENGTH: 89
<212> TYPE: DNA
<213> ORGANISM: Homo sapiens

<400> SEQUENCE: 271
agcctgtggg aaagagaaga gcagggcagg gtgaaggccc ggcggagaca ctctgcccac    60
cccacaccct gcctatgggc cacacagct                                      89

<210> SEQ ID NO 272
<211> LENGTH: 81
<212> TYPE: DNA
<213> ORGANISM: Homo sapiens

<400> SEQUENCE: 272
ggactggagc aggtgagatg gaatttccta aaggtccaga tatttaggac cctggaccca    60
tctcacccgc tgcctctgtc c                                              81

<210> SEQ ID NO 273
<211> LENGTH: 91
<212> TYPE: DNA
<213> ORGANISM: Homo sapiens

<400> SEQUENCE: 273
tgaggggtaa gtttaggctt tcgcggaggg gaggagacat ggagcctggg aactccttgt    60
tctcccctct gctgcctctc cccacccctt a                                   91

<210> SEQ ID NO 274
<211> LENGTH: 105
<212> TYPE: DNA
<213> ORGANISM: Homo sapiens

<400> SEQUENCE: 274
ccagactctg ggtggatgga gcaggtcggg ggccagggga caggaaggct agggcccag     60 agacctgtcc tgggccccat gtccagctct gcccttagtg cttgg                   105

<210> SEQ ID NO 275
<211> LENGTH: 104
<212> TYPE: DNA
<213> ORGANISM: Homo sapiens

<400> SEQUENCE: 275
gtggttaaaa aaaaaaaaaa tggttaagga agcggaccat ggagcagaaa gttgcagtga    60
ctggattctg gctccaggct gcaaatttaa ccattgaata tcac                    104

<210> SEQ ID NO 276
<211> LENGTH: 95
<212> TYPE: DNA
<213> ORGANISM: Homo sapiens

<400> SEQUENCE: 276

```
tcctgaaaga ggttggggca ggcagtgact gttcagacgt ccaatctctt tgggacgcct    60
cttcagcgct gtcttccctg cctctgcctt tagga                               95

<210> SEQ ID NO 277
<211> LENGTH: 100
<212> TYPE: DNA
<213> ORGANISM: Homo sapiens

<400> SEQUENCE: 277
aaaaaaaaaa aagatactaa tacaaatggt catggagggg gaatatagag aagatcaatt    60
ttgtacagaa aaaccattgg ttagtatttt tttttctttt                         100

<210> SEQ ID NO 278
<211> LENGTH: 121
<212> TYPE: DNA
<213> ORGANISM: Homo sapiens

<400> SEQUENCE: 278
gccccccaaa atgcttctgt acccctgccc caacaaggaa ggacaagagg tgtgagccac    60
acacacgcct ggcctcctgt ctttccttgt tggagcaggg atgtagaagc acttgccgca   120
g                                                                  121

<210> SEQ ID NO 279
<211> LENGTH: 121
<212> TYPE: DNA
<213> ORGANISM: Homo sapiens

<400> SEQUENCE: 279
gggagccgcc ggcgggcagg ccgccggggc agcaggcgag ttacctcaac tcccggccgc    60
tccggaggtt gccgggcacc gaggagccgc cgtgcccttc aggcgcctgc ggcggcgacc   120
a                                                                  121

<210> SEQ ID NO 280
<211> LENGTH: 121
<212> TYPE: DNA
<213> ORGANISM: Homo sapiens

<400> SEQUENCE: 280
gctggagcag agagactgag tgagggagtc agagagttaa gagaattagt acaggtgaga    60
ttgtactgat tatcttaact ctctgacccc ctcactcagt aaagatcaga ttgtgccagg   120
c                                                                  121

<210> SEQ ID NO 281
<211> LENGTH: 116
<212> TYPE: DNA
<213> ORGANISM: Homo sapiens

<400> SEQUENCE: 281
aagcaagaca ccgaggtggg aaggggacg aggaggactg ggccctattt ctcccatcta    60
tgtaaaggga gggatatcag ggaagtctct gtctgtgtac tcaagtttgg gatgct       116

<210> SEQ ID NO 282
<211> LENGTH: 99
<212> TYPE: DNA
<213> ORGANISM: Homo sapiens

<400> SEQUENCE: 282
```

```
tgctggccca aggggtaaag gggcagggac gggtggcccc aggaagaagg gcctggtgga      60
gccgctcttc tccctgccca cagagactgg cggagctgc                            99

<210> SEQ ID NO 283
<211> LENGTH: 110
<212> TYPE: DNA
<213> ORGANISM: Homo sapiens

<400> SEQUENCE: 283
aggaacagga cgatgatgct ggcgtcggtg ctggggagcg gcccccgggt gggcctctgc     60
tctggcccct cctggggccc gcactctcgc tctgggcccg ctcctcttcc                110

<210> SEQ ID NO 284
<211> LENGTH: 109
<212> TYPE: DNA
<213> ORGANISM: Homo sapiens

<400> SEQUENCE: 284
atctcacaga ggaagaacag ggctctgagg tcgggagggg aaggcggctc aggacttctg     60
gctccagagc ctcctctcct tccaccatag tgcctgctcc agaggagac                109

<210> SEQ ID NO 285
<211> LENGTH: 121
<212> TYPE: DNA
<213> ORGANISM: Homo sapiens

<400> SEQUENCE: 285
ctttggcaca gtccgtgctc tcaaggagct cacagtcagg aaggcacgtg gaatttcagc    60
ctggagttcc aagtgctgcc ctcagggagt gctgggcctg agctggggtg aggctgcagg    120
g                                                                    121

<210> SEQ ID NO 286
<211> LENGTH: 118
<212> TYPE: DNA
<213> ORGANISM: Homo sapiens

<400> SEQUENCE: 286
ctcacacatg gtacgttttc aatgagctga ttttgtttct ccactcaatg cagtaattga    60
gcttctttgg ttcagtgcat gagtggttca gtggttcatt gggcatcctg gttgaggg     118

<210> SEQ ID NO 287
<211> LENGTH: 87
<212> TYPE: DNA
<213> ORGANISM: Homo sapiens

<400> SEQUENCE: 287
gtgctatagc tatagagact gagtgtgggg tctacagaaa atgtggccat gccctccacc    60
ccagtggctg ggcagccttt ggcacag                                        87

<210> SEQ ID NO 288
<211> LENGTH: 99
<212> TYPE: DNA
<213> ORGANISM: Homo sapiens

<400> SEQUENCE: 288
caccataggt gaggtggggg ccagcaggga gtgggctggg ctgggctggg ccaaggtaca    60
aggcctcacc ctgcatcccg cacccaggct tcaacgtgg                           99
```

```
<210> SEQ ID NO 289
<211> LENGTH: 121
<212> TYPE: DNA
<213> ORGANISM: Homo sapiens

<400> SEQUENCE: 289
aggtggtggt ggggaggacc ctgagggagg gtgggagcac gggagaagag aaggcatacc    60
caacctgacc tacttacctg tccctaccc cacagagggc ttccctggag gccgccattg   120
c                                                                  121

<210> SEQ ID NO 290
<211> LENGTH: 106
<212> TYPE: DNA
<213> ORGANISM: Homo sapiens

<400> SEQUENCE: 290
gggcacgggg gttgggtgtg caaagggtgg cagcaaggaa ggcagggtc ctaaggtgtg     60 tcctcctgcc ctccttgctg tagactttgg cctgagcaaa gaggcc                 106

<210> SEQ ID NO 291
<211> LENGTH: 108
<212> TYPE: DNA
<213> ORGANISM: Homo sapiens

<400> SEQUENCE: 291
cgggagggaa ggagggagga aggggcgctt gggcagaacc aagggtggca gattatccta    60
gggactcttg gggcagaacc agacgcctct gcgtcctccc ctctcccc              108

<210> SEQ ID NO 292
<211> LENGTH: 99
<212> TYPE: DNA
<213> ORGANISM: Homo sapiens

<400> SEQUENCE: 292
caggaattcc actggcagcc agggcagagg gcacaggaat ctgaggtgac tggcacagaa    60
gactcaggcc tgtggctcct ccctcaggac tgcttccta                          99

<210> SEQ ID NO 293
<211> LENGTH: 91
<212> TYPE: DNA
<213> ORGANISM: Homo sapiens

<400> SEQUENCE: 293
gtgagtgggg ctgggctgtg ggggaggggt ggggtggcag ggaacaggca gaccatccct    60
tctacccaca ggatcctgct gctgcagaca g                                  91

<210> SEQ ID NO 294
<211> LENGTH: 79
<212> TYPE: DNA
<213> ORGANISM: Homo sapiens

<400> SEQUENCE: 294
actcaggcac tgcctctgac gatgctctcc cagatctggt acgctcatgg ggaagagccc    60
agcgccaggc agtgttgga                                                79

<210> SEQ ID NO 295
<211> LENGTH: 105
<212> TYPE: DNA
<213> ORGANISM: Homo sapiens
```

```
<400> SEQUENCE: 295
tggctgggag aggagcatag gatgcggcag gagggcagtg gaggctgagg tacggatttc    60
taggcccgcc ctaccctcct ctctgcccct agtgcccgtg gccaa                    105

<210> SEQ ID NO 296
<211> LENGTH: 105
<212> TYPE: DNA
<213> ORGANISM: Homo sapiens

<400> SEQUENCE: 296
tggctgggag aggagcatag gatgcggcag gagggcagtg gaggctgagg tacggatttc    60
taggcccgcc ctaccctcct ctctgcccct agtgcccgtg gccaa                    105

<210> SEQ ID NO 297
<211> LENGTH: 113
<212> TYPE: DNA
<213> ORGANISM: Homo sapiens

<400> SEQUENCE: 297
gcggcggaca ccatcttctt taaaccctca gtccgtattg gtctctatgg catccataga    60
ggccattcgg ctctgaggtc ctcagtaaag aaacttagat ggtattactg tgt           113

<210> SEQ ID NO 298
<211> LENGTH: 118
<212> TYPE: DNA
<213> ORGANISM: Homo sapiens

<400> SEQUENCE: 298
tcacatgtcc tcagctgttg tctgggtgag gcatccctgt cgtgggagca gccacagctc    60
tgcctggtct cccagagcag ggacgctttg tccgcattta cagcagtcta cacagatg     118

<210> SEQ ID NO 299
<211> LENGTH: 72
<212> TYPE: DNA
<213> ORGANISM: Homo sapiens

<400> SEQUENCE: 299
agccacacgg tcacacctaa tgtcatagcc ggtagagcag ggagccctct ggatggaagc    60
actgtgaggc tc                                                        72

<210> SEQ ID NO 300
<211> LENGTH: 73
<212> TYPE: DNA
<213> ORGANISM: Homo sapiens

<400> SEQUENCE: 300
tgtatccttg aatggatttt tggagcagga gtggacacct gacccaaagg aaatcaatcc    60
ataggctagc aat                                                       73

<210> SEQ ID NO 301
<211> LENGTH: 78
<212> TYPE: DNA
<213> ORGANISM: Homo sapiens

<400> SEQUENCE: 301
gagcgtcacg ttgacactca aaaagtttca gattttggaa catttcggat tttggatttt    60
tggatcaggg atgctcaa                                                  78
```

```
<210> SEQ ID NO 302
<211> LENGTH: 54
<212> TYPE: DNA
<213> ORGANISM: Homo sapiens

<400> SEQUENCE: 302
ccccgcatgg gtggttcagt ggcagaattc tcaaattgta atccccataa tccc            54

<210> SEQ ID NO 303
<211> LENGTH: 87
<212> TYPE: DNA
<213> ORGANISM: Homo sapiens

<400> SEQUENCE: 303
gacagtgcag tcacccataa agtagaaagc actactaaca gcactggagg gtgtagtgtt      60
tcctacttta tggatgagtg tactgtg                                          87

<210> SEQ ID NO 304
<211> LENGTH: 85
<212> TYPE: DNA
<213> ORGANISM: Homo sapiens

<400> SEQUENCE: 304
attgatcatc gacacttcga acgcaattgc agcccgggtt cctcccaggg ctttgcctgt      60
ctgagcgtcg cttgccgatc agtag                                            85

<210> SEQ ID NO 305
<211> LENGTH: 87
<212> TYPE: DNA
<213> ORGANISM: Homo sapiens

<400> SEQUENCE: 305
agcttccctg gctctagcag cacagaaata ttggcacagg aagcgagtc tgccaatatt       60 ggctgtgctg ctccaggcag ggtggtg                                          87

<210> SEQ ID NO 306
<211> LENGTH: 68
<212> TYPE: DNA
<213> ORGANISM: Homo sapiens

<400> SEQUENCE: 306
ccctcgtctt acccagcagt gtttgggtgc ggttgggagt ctctaatact gccgggtaat      60
gatggagg                                                               68

<210> SEQ ID NO 307
<211> LENGTH: 72
<212> TYPE: DNA
<213> ORGANISM: Homo sapiens

<400> SEQUENCE: 307
cttgggaatg gcaaggaaac cgttaccatt actgagttta gtaatggtaa tggttctctt      60
gctataccca ga                                                          72

<210> SEQ ID NO 308
<211> LENGTH: 76
<212> TYPE: DNA
<213> ORGANISM: Homo sapiens

<400> SEQUENCE: 308 gaggggaag acgggaggaa agaagggagt ggttccatca cgcctcctca ctcctctcct       60
```

```
cccgtcttct cctctc                                                    76
```

<210> SEQ ID NO 309
<211> LENGTH: 84
<212> TYPE: DNA
<213> ORGANISM: Homo sapiens

<400> SEQUENCE: 309

```
ttgacttagc tgggtagtgg ggaacccttc catgaggagt agaacactcc ttatgcaaga    60
ttcccttcta cctggctggg ttgg                                           84
```

<210> SEQ ID NO 310
<211> LENGTH: 81
<212> TYPE: DNA
<213> ORGANISM: Homo sapiens

<400> SEQUENCE: 310

```
gatactcgaa ggagaggttg tccgtgttgt cttctcttta tttatgatga aacatacacg    60
ggaaacctct tttttagtat c                                              81
```

<210> SEQ ID NO 311
<211> LENGTH: 110
<212> TYPE: DNA
<213> ORGANISM: Homo sapiens

<400> SEQUENCE: 311

```
ccggatctca cacggtggtg ttaatatctc gctgggcct ccaaaatgtt gtgcccaggg     60
gtgttagaga aaacaccaca ctttgagatg aattaagagt cctttattag               110
```

<210> SEQ ID NO 312
<211> LENGTH: 119
<212> TYPE: DNA
<213> ORGANISM: Homo sapiens

<400> SEQUENCE: 312

```
aggattctgc tcatgccagg gtgaggtagt aagttgtatt gttgtggggt agggatatta    60
ggccccaatt agaagataac tatacaactt actactttcc ctggtgtgtg gcatattca    119
```

<210> SEQ ID NO 313
<211> LENGTH: 106
<212> TYPE: DNA
<213> ORGANISM: Homo sapiens

<400> SEQUENCE: 313

```
gcgcagcgcc ctgtctccca gcctgaggtg cagtgctgca tctctggtca gttgggagtc    60
tgagatgaag cactgtagct caggaagaga gaagttgttc tgcagc                   106
```

<210> SEQ ID NO 314
<211> LENGTH: 88
<212> TYPE: DNA
<213> ORGANISM: Homo sapiens

<400> SEQUENCE: 314

```
caccttgtcc tcacggtcca gttttcccag gaatccctta gatgctaaga tgggattcc     60 tggaaatact gttcttgagg tcatggtt                                       88
```

<210> SEQ ID NO 315
<211> LENGTH: 110
<212> TYPE: DNA
<213> ORGANISM: Homo sapiens -continued

<400> SEQUENCE: 315
aaagatcctc agacaatcca tgtgcttctc ttgtccttca ttccaccgga gtctgtctca    60
tacccaacca gatttcagtg gagtgaagtt caggaggcat ggagctgaca             110

<210> SEQ ID NO 316
<211> LENGTH: 72
<212> TYPE: DNA
<213> ORGANISM: Homo sapiens

<400> SEQUENCE: 316
tgtcgggtag cttatcagac tgatgttgac tgttgaatct catggcaaca ccagtcgatg    60
ggctgtctga ca                                                       72

<210> SEQ ID NO 317
<211> LENGTH: 71
<212> TYPE: DNA
<213> ORGANISM: Homo sapiens

<400> SEQUENCE: 317
ggagaggagg caagatgctg gcatagctgt tgaactggga acctgctatg ccaacatatt    60
gccatctttc c                                                        71

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
catagatgcc gcggaaggt                                                19

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
cccgaggttt ctcagagcct                                               20

<210> SEQ ID NO 320
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 320
cctcagacat ccccgattga aagaacc                                       27

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 321
ctttctcaag gaccaccgca                                                    20

<210> SEQ ID NO 322
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
gcctcggcca tccgct                                                        16

<210> SEQ ID NO 323
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 323
cattcaagaa ctggcccttc ttggagg                                            27

<210> SEQ ID NO 324
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
agatcgacaa tgcccgt                                                       17

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
agagcctgtt ccgtctcaaa                                                    20

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 326
tggctgcaga tgacttccga acca                                               24

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
```
tcatttgctc aaagctggct g                                    21

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
aaacttggga gaagagcaaa acc                                  23

<210> SEQ ID NO 329
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 329
aaatgtttgg tgatgaaggc agaaatgaat gg                        32

<210> SEQ ID NO 330
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
ttcattccat tattagacgt tccct                                25

<210> SEQ ID NO 331
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
gattattcca catgtaattg gtggg                                25

<210> SEQ ID NO 332
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 332
ccagcaacac taccacagtg tcaggca                              27

<210> SEQ ID NO 333
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
ttaaattgtc acagacaagt aatgtcg                                    27

<210> SEQ ID NO 334
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
tggcttttgt aaagaagttc aggtac                                     26

<210> SEQ ID NO 335
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 335
tggttcattc atctctatgg taacagcttc ctcct                           35

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
ccctggagac ctgagaacca                                            20

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
aaccatagcg gtacaggtat tcct                                       24

<210> SEQ ID NO 338
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 338
tctcaccgac aggcagctgg ca                                         22

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
cctgagatct gcaaacagga cat                                        23

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
ccaaatgaac cggtccttga                                             20

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 341
ttgatggcat cgctcagatc cgtg                                        24

<210> SEQ ID NO 342
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
gctaaagtga ggatggtgat tatcact                                     27

<210> SEQ ID NO 343
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
actaacaaag ttttcttctt taatttttcc at                               32

<210> SEQ ID NO 344
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 344
accagaggct cagttcaagg ctcagggaa                                   29

<210> SEQ ID NO 345
<211> LENGTH: 22
<212> TYPE: DNA
<213> ORGANISM: Homo sapiens

<400> SEQUENCE: 345
tcccccaacc cacagcacac ac                                          22

<210> SEQ ID NO 346
<211> LENGTH: 23

<212> TYPE: DNA
<213> ORGANISM: Homo sapiens

<400> SEQUENCE: 346
cccggagagc ggagcacaac aca                                              23

<210> SEQ ID NO 347
<211> LENGTH: 19
<212> TYPE: DNA
<213> ORGANISM: Homo sapiens

<400> SEQUENCE: 347
ccggagagcg gagcacaac                                                   19

<210> SEQ ID NO 348
<211> LENGTH: 18
<212> TYPE: DNA
<213> ORGANISM: Homo sapiens

<400> SEQUENCE: 348
ccaaggaagg cagcaggc                                                    18

<210> SEQ ID NO 349
<211> LENGTH: 18
<212> TYPE: DNA
<213> ORGANISM: Homo sapiens

<400> SEQUENCE: 349
gatggaattt cctaaagg                                                    18

<210> SEQ ID NO 350
<211> LENGTH: 17
<212> TYPE: DNA
<213> ORGANISM: Homo sapiens

<400> SEQUENCE: 350
ggaggggagg agacatg                                                     17

<210> SEQ ID NO 351
<211> LENGTH: 22
<212> TYPE: DNA
<213> ORGANISM: Homo sapiens

<400> SEQUENCE: 351
gcagtgactg ttcagacgtc ca                                               22

<210> SEQ ID NO 352
<211> LENGTH: 22
<212> TYPE: DNA
<213> ORGANISM: Homo sapiens

<400> SEQUENCE: 352
tgtctttcct tgttggagca gg                                               22

<210> SEQ ID NO 353
<211> LENGTH: 20
<212> TYPE: DNA
<213> ORGANISM: Homo sapiens

<400> SEQUENCE: 353
cagcaggcga gttacctcaa                                                  20

<210> SEQ ID NO 354

```
<211> LENGTH: 18
<212> TYPE: DNA
<213> ORGANISM: Homo sapiens

<400> SEQUENCE: 354
gaggaggact gggcccta                                                    18

<210> SEQ ID NO 355
<211> LENGTH: 23
<212> TYPE: DNA
<213> ORGANISM: Homo sapiens

<400> SEQUENCE: 355
agccgctctt ctccctgccc aca                                              23

<210> SEQ ID NO 356
<211> LENGTH: 24
<212> TYPE: DNA
<213> ORGANISM: Homo sapiens

<400> SEQUENCE: 356
agccgctctt ctccctgccc acag                                             24

<210> SEQ ID NO 357
<211> LENGTH: 18
<212> TYPE: DNA
<213> ORGANISM: Homo sapiens

<400> SEQUENCE: 357
tggggagcgg cccccggg                                                    18

<210> SEQ ID NO 358
<211> LENGTH: 23
<212> TYPE: DNA
<213> ORGANISM: Homo sapiens

<400> SEQUENCE: 358
gaggtcggga ggggaaggcg gct                                              23

<210> SEQ ID NO 359
<211> LENGTH: 17
<212> TYPE: DNA
<213> ORGANISM: Homo sapiens

<400> SEQUENCE: 359
tcaaggagct cacagtc                                                     17

<210> SEQ ID NO 360
<211> LENGTH: 19
<212> TYPE: DNA
<213> ORGANISM: Homo sapiens

<400> SEQUENCE: 360
gcatgagtgg ttcagtggt                                                   19

<210> SEQ ID NO 361
<211> LENGTH: 21
<212> TYPE: DNA
<213> ORGANISM: Homo sapiens

<400> SEQUENCE: 361
gtgggctggg ctgggctggg c                                                21
```

```
<210> SEQ ID NO 362
<211> LENGTH: 23
<212> TYPE: DNA
<213> ORGANISM: Homo sapiens

<400> SEQUENCE: 362
ggaggaccct gagggagggt ggg                                              23

<210> SEQ ID NO 363
<211> LENGTH: 17
<212> TYPE: DNA
<213> ORGANISM: Homo sapiens

<400> SEQUENCE: 363
tgagggaggg tgggagc                                                     17

<210> SEQ ID NO 364
<211> LENGTH: 23
<212> TYPE: DNA
<213> ORGANISM: Homo sapiens

<400> SEQUENCE: 364
tggcagcaag gaaggcaggg gtc                                              23

<210> SEQ ID NO 365
<211> LENGTH: 18
<212> TYPE: DNA
<213> ORGANISM: Homo sapiens

<400> SEQUENCE: 365
gagggaagga gggaggaa                                                    18

<210> SEQ ID NO 366
<211> LENGTH: 25
<212> TYPE: DNA
<213> ORGANISM: Homo sapiens

<400> SEQUENCE: 366
cagggcagag ggcacaggaa tctga                                            25

<210> SEQ ID NO 367
<211> LENGTH: 17
<212> TYPE: DNA
<213> ORGANISM: Homo sapiens

<400> SEQUENCE: 367
gggaagagcc cagcgcc                                                     17

<210> SEQ ID NO 368
<211> LENGTH: 23
<212> TYPE: DNA
<213> ORGANISM: Homo sapiens

<400> SEQUENCE: 368
accctcagtc cgtattggtc tct                                              23

<210> SEQ ID NO 369
<211> LENGTH: 23
<212> TYPE: DNA
<213> ORGANISM: Homo sapiens

<400> SEQUENCE: 369
gtctcccaga gcagggacgc ttt                                              23
```

```
<210> SEQ ID NO 370
<211> LENGTH: 21
<212> TYPE: DNA
<213> ORGANISM: Homo sapiens

<400> SEQUENCE: 370
ttagaaaaag aggggtgag g                                          21

<210> SEQ ID NO 371
<211> LENGTH: 18
<212> TYPE: DNA
<213> ORGANISM: Homo sapiens

<400> SEQUENCE: 371
tggggtgtgg aggggagg                                             18

<210> SEQ ID NO 372
<211> LENGTH: 17
<212> TYPE: DNA
<213> ORGANISM: Homo sapiens

<400> SEQUENCE: 372
aggggagcag ggaggaa                                              17

<210> SEQ ID NO 373
<211> LENGTH: 21
<212> TYPE: DNA
<213> ORGANISM: Homo sapiens

<400> SEQUENCE: 373
tggcctgacg tgaggaggag g                                         21

<210> SEQ ID NO 374
<211> LENGTH: 21
<212> TYPE: DNA
<213> ORGANISM: Homo sapiens

<400> SEQUENCE: 374
acggacaggg aacttttga t                                          21

<210> SEQ ID NO 375
<211> LENGTH: 22
<212> TYPE: DNA
<213> ORGANISM: Homo sapiens

<400> SEQUENCE: 375
gcccagtgct ctgaatgtca aa                                        22

<210> SEQ ID NO 376
<211> LENGTH: 23
<212> TYPE: DNA
<213> ORGANISM: Homo sapiens

<400> SEQUENCE: 376
tctgcccagt gctctgaatg tca                                       23

<210> SEQ ID NO 377
<211> LENGTH: 18
<212> TYPE: DNA
<213> ORGANISM: Homo sapiens

<400> SEQUENCE: 377
ggcgggagta actatgac                                             18
```

<210> SEQ ID NO 378
<211> LENGTH: 22
<212> TYPE: DNA
<213> ORGANISM: Homo sapiens

<400> SEQUENCE: 378
cgggtaaacg gcgggagtaa ct                                            22

<210> SEQ ID NO 379
<211> LENGTH: 24
<212> TYPE: DNA
<213> ORGANISM: Homo sapiens

<400> SEQUENCE: 379
agcaggcgca cggccgtctg gatc                                          24

<210> SEQ ID NO 380
<211> LENGTH: 20
<212> TYPE: DNA
<213> ORGANISM: Homo sapiens

<400> SEQUENCE: 380
gcacggccgt ctggatctcc                                               20

<210> SEQ ID NO 381
<211> LENGTH: 17
<212> TYPE: DNA
<213> ORGANISM: Homo sapiens

<400> SEQUENCE: 381
gaggaaggaa ggggaaa                                                  17

<210> SEQ ID NO 382
<211> LENGTH: 26
<212> TYPE: DNA
<213> ORGANISM: Homo sapiens

<400> SEQUENCE: 382
cagtgctctg aatgtcaaag tgaaga                                        26

<210> SEQ ID NO 383
<211> LENGTH: 18
<212> TYPE: DNA
<213> ORGANISM: Homo sapiens

<400> SEQUENCE: 383
gggtaaacgg cgggagta                                                 18

<210> SEQ ID NO 384
<211> LENGTH: 19
<212> TYPE: DNA
<213> ORGANISM: Homo sapiens

<400> SEQUENCE: 384
aaatggattt ttggagcag                                                19

<210> SEQ ID NO 385
<211> LENGTH: 19
<212> TYPE: DNA
<213> ORGANISM: Homo sapiens

<400> SEQUENCE: 385
tgcaagatca gagggga                                                    19

<210> SEQ ID NO 386
<211> LENGTH: 17
<212> TYPE: DNA
<213> ORGANISM: Homo sapiens

<400> SEQUENCE: 386
ggggctgtag ctcaggg                                                    17

<210> SEQ ID NO 387
<211> LENGTH: 17
<212> TYPE: DNA
<213> ORGANISM: Homo sapiens

<400> SEQUENCE: 387
gccggtacag tgaaaat                                                    17

<210> SEQ ID NO 388
<211> LENGTH: 18
<212> TYPE: DNA
<213> ORGANISM: Homo sapiens

<400> SEQUENCE: 388
gccggtacag tgaaaatg                                                   18

<210> SEQ ID NO 389
<211> LENGTH: 19
<212> TYPE: RNA
<213> ORGANISM: Homo sapiens

<400> SEQUENCE: 389
aauggauuuu uggagcagg                                                  19

<210> SEQ ID NO 390
<211> LENGTH: 19
<212> TYPE: RNA
<213> ORGANISM: Homo sapiens

<400> SEQUENCE: 390
uggauuuuug gaucaggga                                                  19

<210> SEQ ID NO 391
<211> LENGTH: 18
<212> TYPE: RNA
<213> ORGANISM: Homo sapiens

<400> SEQUENCE: 391
gcaugggugg uucagugg                                                   18

<210> SEQ ID NO 392
<211> LENGTH: 27
<212> TYPE: RNA
<213> ORGANISM: Homo sapiens

<400> SEQUENCE: 392
auugaucauc gacacuucga acgcaau                                         27

<210> SEQ ID NO 393
<211> LENGTH: 21
<212> TYPE: RNA
<213> ORGANISM: Homo sapiens

<400> SEQUENCE: 393

```
uagcagcaca gaaauauugg c                                              21

<210> SEQ ID NO 394
<211> LENGTH: 23
<212> TYPE: RNA
<213> ORGANISM: Homo sapiens

<400> SEQUENCE: 394
uaauacugcc ggguaaugau gga                                            23

<210> SEQ ID NO 395
<211> LENGTH: 22
<212> TYPE: RNA
<213> ORGANISM: Homo sapiens

<400> SEQUENCE: 395
aaaccguuac cauuacugag uu                                             22

<210> SEQ ID NO 396
<211> LENGTH: 22
<212> TYPE: RNA
<213> ORGANISM: Homo sapiens

<400> SEQUENCE: 396
aagacgggag gaaagaaggg ag                                             22

<210> SEQ ID NO 397
<211> LENGTH: 22
<212> TYPE: RNA
<213> ORGANISM: Homo sapiens

<400> SEQUENCE: 397
cuuaugcaag auucccuucu ac                                             22

<210> SEQ ID NO 398
<211> LENGTH: 22
<212> TYPE: RNA
<213> ORGANISM: Homo sapiens

<400> SEQUENCE: 398
ugaaacauac acgggaaacc uc                                             22

<210> SEQ ID NO 399
<211> LENGTH: 17
<212> TYPE: RNA
<213> ORGANISM: Homo sapiens

<400> SEQUENCE: 399
ucucgcuggg gccucca                                                   17

<210> SEQ ID NO 400
<211> LENGTH: 22
<212> TYPE: RNA
<213> ORGANISM: Homo sapiens

<400> SEQUENCE: 400
ugagguagua aguuguauug uu                                             22

<210> SEQ ID NO 401
<211> LENGTH: 21
<212> TYPE: RNA
<213> ORGANISM: Homo sapiens
```

```
<400> SEQUENCE: 401
ugagaugaag cacuguagcu c                                              21

<210> SEQ ID NO 402
<211> LENGTH: 22
<212> TYPE: RNA
<213> ORGANISM: Homo sapiens

<400> SEQUENCE: 402
uccuucauuc caccggaguc ug                                             22

<210> SEQ ID NO 403
<211> LENGTH: 21
<212> TYPE: RNA
<213> ORGANISM: Homo sapiens

<400> SEQUENCE: 403
aggcaagaug cuggcauagc u                                              21

<210> SEQ ID NO 404
<211> LENGTH: 23
<212> TYPE: RNA
<213> ORGANISM: Homo sapiens

<400> SEQUENCE: 404
uuaaugcuaa ucgugauagg ggu                                            23

<210> SEQ ID NO 405
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
gcguaccgac gcguagacgg ac                                             22

<210> SEQ ID NO 406
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 406
ttgtaatacg actcaacagt agataaagcg acgcgcg                             37

<210> SEQ ID NO 407
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 407
ttgtaatacg actcaaacgc gacttatcga acgataa                             37

<210> SEQ ID NO 408
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 408
ttgtaatacg actcaaggtt gcctacatag taacttc                            37

<210> SEQ ID NO 409
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 409
ttgtaatacg actcacccgg taacaattag tcccgcg                            37
```

METHODS OF DETECTING CERVICAL CANCER

This application is a continuation of U.S. patent application Ser. No. 13/658,276, filed Oct. 23, 2012, which is a continuation of U.S. patent application Ser. No. 12/715,179, filed Mar. 1, 2010, which is a continuation-in-part of U.S. patent application Ser. No. 12/688,784, filed Jan. 15, 2010, which claims priority to U.S. Provisional Application No. 61/145,439, filed Jan. 16, 2009, and U.S. Provisional Application No. 61/165,835, filed Apr. 1, 2009. U.S. patent application Ser. Nos. 12/715,179 and 12/688,784 and U.S. Provisional Application Nos. 61/145,439 and 61/165,835 are incorporated by reference herein in their entireties for any purpose.

1. BACKGROUND

Cervical cancer is the second most common cause of cancer-related mortality in women worldwide. Epidemiological and laboratory studies suggest a key role for human papillomavirus (HPV) in cervical carcinogenesis (Walboomers, J. M. et al. (1999) *J. Pathol.* 189:12-19; Zur, H. H. (2002) *Nat. Rev. Cancer* 2:342-350). Importantly, however, HPV infection alone is not sufficient for cervical carcinogenesis, and additional steps occur over years or decades following initial infection. Most HPV infections resolve spontaneously, but if an oncogenic (high risk) HPV infection persists, there may be progression to a high grade cervical dysplasia or cervical cancer. (Nobbenhuis, M. A. et al. (2001) *Lancet* 358:1782-1783). High risk HPVs include HPV-16, 18, 31, 33, 35, 39, 45, 51, 52, 56, 58, 59, 66, and 68, with HPV-16 and 18 accounting for up to 70% of cervical cancers worldwide.

The Papanicolaou (Pap) smear has become the most commonly used method to screen for cervical dysplasia. It has been a success and the incidence of cervical cancer has been dramatically reduced. However, cytology screening programs have limitations, especially limited sensitivity, estimated at only 51% (Nanda K. et al. (2000) *Ann. Intern. Med.* 132:810-819), and repeated tests are therefore necessary. In addition, a high-quality cytology screening program requires highly-trained personnel. Furthermore, although cytological screening programs have reduced the incidence of squamous cervical cancer (SCC), the incidence of cervical adenocarcinoma (AC) has continued to increase. The reason for this is unclear, but it may, in part, be due to difficulties detecting the precursor form of AC using conventional screening methods. (Bray, F. B. et al. (2005) *Cancer Epidemiol. Biomarkers Prev.* 14:2191-2199).

HPV DNA testing can be more sensitive than cytologic testing in detecting high-grade cervical dysplasia. However, HPV testing often has lower specificity than cytologic testing since most HPV infections are transient in nature. (Koliopoulous, G. M. et al. (2007) *Gynecol. Oncol.* 104: 232-246). In order to improve the clinical specificity of the molecular HPV tests, a number of molecular markers associated with cervical cancer precursor lesions (i.e. Cervical Intra-epithelial Neoplasia ("CIN") grades 1, 2 and 3) have been evaluated. (See e.g., Altieri D. C. (2003) *Nat Rev. Cancer* 3:46-54; Li C. et al. (2007) *Mod. Pathol.* 20:242-247; Andersson, S. et al. (2006) *Br. J. Cancer* 95:331-338; Martin, C. M. et al. (2006) *Expert Rev. Mol. Diagn.* 6:217-229; Branca, M. et al. (2006) *Int. J. Gynecol. Pathol.* 25:383-392; Harris C. P. et al. (2003) *Genes Chromosomes Cancer* 36:233-241). However, there remains a need for molecular markers in cervical dysplasia which indicate a high risk of progression to cancer.

2. SUMMARY

Methods for detecting the presence of cervical dysplasia in a subject are provided. In some embodiments, a method comprises detecting a level of at least one target RNA in a cervical sample from the subject. In some embodiments, the at least one target RNA (i) is capable of specifically hybridizing to a nucleic acid having a sequence selected from SEQ ID NOs: 1 to 41 and 133 to 211; or (ii) comprises a sequence that is complementary to at least 15 contiguous nucleotides of a sequence selected from SEQ ID NOs: 1 to 41 and 133 to 211; or (iii) comprises at least 15 contiguous nucleotides of a sequence selected from SEQ ID NOs: 345 to 388. In some embodiments, a method comprises comparing the level of the at least one target RNA in the cervical sample to a normal level of the at least one target RNA. In some embodiments, a level of at least one target RNA in the sample that is greater than a normal level of the at least one target RNA indicates the presence of cervical dysplasia in the sample.

Methods for facilitating the detection of cervical dysplasia in a subject are also provided. In some embodiments, the method comprises detecting a level of at least one target RNA in a cervical sample from the subject. In some embodiments, the at least one target RNA (i) is capable of specifically hybridizing to a nucleic acid having a sequence selected from SEQ ID NOs: 1 to 41 and 133 to 211; or (ii) comprises a sequence that is complementary to at least 15 contiguous nucleotides of a sequence selected from SEQ ID NOs: 1 to 41 and 133 to 211; or (iii) comprises at least 15 contiguous nucleotides of a sequence selected from SEQ ID NOs: 345 to 388. In some embodiments, a method comprises communicating the results of the detection to a medical practitioner for the purpose of determining whether the subject has cervical dysplasia.

In some embodiments, detecting a level of at least one target RNA in a cervical sample comprises hybridizing nucleic acids of the sample with at least one polynucleotide that is complementary to a target RNA in the sample or to a complement thereof. In some embodiments, a method further comprises detecting at least one complex comprising a polynucleotide hybridized to at least one nucleic acid selected from the target RNA, a DNA amplicon of the target RNA, and a complement of the target RNA.

In some embodiments, a method for detecting the presence of cervical dysplasia in a subject comprises obtaining a cervical sample from the subject and providing the sample to a laboratory for detection of the level of at least one target RNA in the sample. In some embodiments, the at least one target RNA: (i) is capable of specifically hybridizing to a nucleic acid having a sequence selected from SEQ ID NOs: 1 to 41 and 133 to 211; or (ii) comprises a sequence that is complementary to at least 15 contiguous nucleotides of a sequence selected from SEQ ID NOs: 1 to 41 and 133 to 211; or (iii) comprises at least 15 contiguous nucleotides of a sequence selected from SEQ ID NOs: 345 to 388. In some embodiments, the method comprises receiving from the laboratory a communication indicating the level of at least one target RNA in the sample. In some embodiments, a level of at least one target RNA that is greater than a normal level of the at least one target RNA indicates the presence of cervical dysplasia.

In some embodiments, a method comprises detecting levels of at least two, at least three, at least five, or at least ten target RNAs. In some embodiments, detection of a level of at least one target RNA that is greater than a normal level of the at least one target RNA indicates the presence of cervical dysplasia. In some embodiments, detection of levels of at least two target RNAs that are greater than normal levels of the at least two target RNAs indicates the presence of cervical dysplasia. In some embodiments, detection of levels of at least three target RNAs that are greater than normal levels of the at least two target RNAs indicates the presence of cervical dysplasia. In some embodiments, detection of levels of at least five target RNAs that are greater than normal levels of the at least two target RNAs indicates the presence of cervical dysplasia.

In some embodiments, a method comprises detecting a level of at least one target RNA that (i) does not specifically hybridize to a nucleic acid having a sequence selected from SEQ ID NOs: 1 to 41 and 133 to 211; and (ii) does not comprise a sequence that is complementary to at least 15 contiguous nucleotides of a sequence selected from SEQ ID NOs: 1 to 41 and 133 to 211; and (iii) does not comprise at least 15 contiguous nucleotides of a sequence selected from SEQ ID NOs: 345 to 388.

In some embodiments, a method further comprises detection of a level of at least one target RNA that is an mRNA. In some embodiments, the mRNA is selected from CDKN2A, MKI67, TOP2A, MCM5, BIRC5, MMP9, and MCM2.

In some embodiments, a synthetic polynucleotide is provided. In some embodiments, a synthetic polynucleotide comprises a first region, wherein the first region comprises a sequence of at least 8, at least 9, at least 10, at least 11, at least 12, at least 13, at least 14, at least 15, at least 16, at least 17, or at least 18 contiguous nucleotides that is identical or complementary to a sequence of at least 8 contiguous nucleotides of one of SEQ ID NOs: 1 to 7, 9 to 37, 133 to 201, and 345 to 388. In some embodiments, the first region is identical or complementary to a region of a target RNA. In some embodiments, a synthetic polynucleotide comprises a second region that is not identical or complementary to a region of the target RNA. In some embodiments, a synthetic polynucleotide comprises a detectable label. In some embodiments, a synthetic polynucleotide comprises a FRET label. In some embodiments, the synthetic polynucleotide comprises a second region that is not identical or complementary to a region of the target RNA.

In some embodiments, a composition is provided. In some embodiments, a composition comprises a plurality of synthetic polynucleotides. In some embodiments, a kit is provided. In some embodiments, a kit comprises a synthetic polynucleotide. In some embodiments, a kit comprises a composition. In some embodiments, a kit comprises at least one polymerase and/or dNTPs.

Further embodiments and details of the inventions are described below.

3. BRIEF DESCRIPTION OF THE FIGURES

FIG. 1 shows an exemplary electropherogram obtained on an Agilent Bioanalyser 2100 to assess the quality of total RNA purified as described in Example 1. Total RNA from cell line CaSki is shown.

FIG. 2 provides analysis by agarose gel electrophoresis under denaturing conditions of the quality of total RNA purified as described in Example 1 from cell lines CaSki, SW756, ME180, SiHA, C-4I, and C-4II.

4. DETAILED DESCRIPTION

4.1. Detecting Cervical Dysplasia

4.1.1. General Methods

Figure 1:
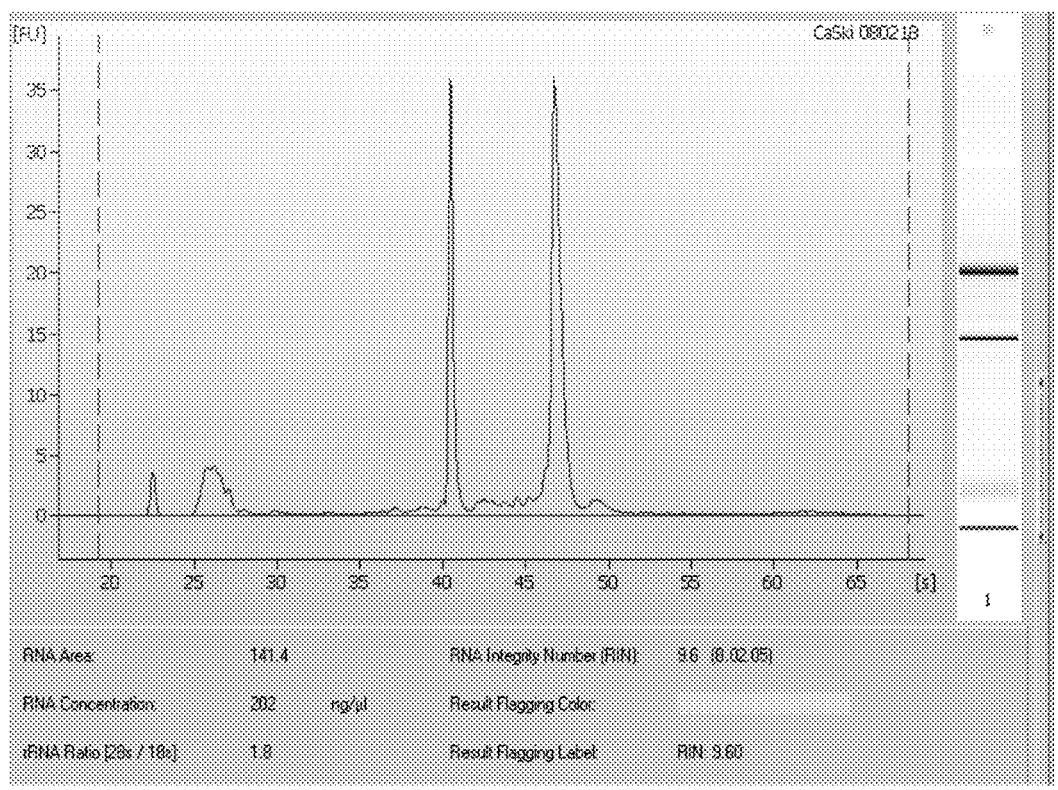

Methods of measuring levels of microRNA species disclosed herein are provided, wherein elevated levels of the microRNA species is indicative of cervical dysplasia. In some embodiments, methods are presented for detecting human cervical dysplasia, such as cervical dysplasia likely to progress to carcinoma. In some embodiments, the method comprises detecting an above-normal level of at least one target RNA that is capable of specifically hybridizing to a sequence selected from SEQ ID NOs: 1 to 41 and 133 to 211. In some embodiments, the method comprises detecting an above-normal level of at least one target RNA, wherein at least one target RNA comprises at least 15, at least 16, at least 17, at least 18, at least 19, at least 20, at least 21, at least 22, at least 23, or at least 24 contiguous nucleotides of a sequence selected from SEQ ID NOs: 345 to 388. In some embodiments, the method comprises detecting an above-normal level of at least one target RNA that comprises a sequence that is complementary to at least 15, at least 16, at least 17, at least 18, at least 19, at least 20, at least 21, at least 22, at least 23, or at least 24 contiguous nucleotides of a sequence selected from SEQ ID NO.:1 to 41 and 133 to 211. In some embodiments, the target RNA, in its mature form, comprises fewer than 30 nucleotides. The target RNA, in some embodiments, is a microRNA.

In the present disclosure, "a sequence selected from" encompasses both "one sequence selected from" and "one or more sequences selected from." Thus, when "a sequence selected from" is used, it is to be understood that one, or more than one, of the listed sequences may be chosen.

Detection of a level of target RNA that is greater than a normal level of target RNA indicates the presence of cervical dysplasia in the sample. In some embodiments, the detecting is done quantitatively. In other embodiments, the detecting is done qualitatively. In some embodiments, detecting a target RNA comprises forming a complex comprising a polynucleotide and a nucleic acid selected from a target RNA, a DNA amplicon of a target RNA, and a complement of a target RNA. In some embodiments, the level of the complex is then detected and compared to a normal level of the same complex. The level of the complex, in some embodiments, correlates with the level of the target RNA in the sample.

"Cervical dysplasia," which is also known as cervical intraepithelial neoplasia ("CIN"), corresponds to precancerous changes of the cervix that are evidenced by an abnormal growth on the surface of the cervix. Cervical dysplasia is divided into three categories: CIN 1, which is mild dysplasia in which only a few cells are abnormal; CIN 2, which is moderate to marked dysplasia in which the abnormal cells involve about one-half of the thickness of the surface lining of the cervix; and CIN 3, which includes severe dysplasia to carcinoma-in-situ (i.e., precancerous cells limited to the top epithelial layer of the cervix). CIN 3 is unlikely to regress spontaneously, and if left untreated, can penetrate the basement membrane and become an invasive carcinoma.

Table 1, below, lists 41 hybridization probes that have been found to be complementary to, and hybridize with, target RNAs in cancer cells. These target RNAs were detected at elevated levels in certain human cervical cell lines that were assayed using microarrays (Example 1). Thirty-six of the probes are believed to be complementary to, and hybridize with, target RNA species that are expressed in human cells. The other five probes are complementary to, and hybridize with, publicly known microRNAs that have been deposited by others into miRBase (http://microrna.sanger.ac.uk/; see Griffiths-Jones S. et al. (2007) Nucl. Acids Res. 36:154-158): hsa-miR-423-5p, hsa-miR-765, hsa-miR-92b*, hsa-miR-663, and hsa-miR-936). However, to the knowledge of the inventors, these five known microRNAs have not been disclosed to have utility for detecting cervical dysplasia.

Table 11, below, lists hybridization probes that have been found to be complementary to, and hybridize with, target RNAs in cancer cells. These target RNAs were detected at elevated levels in certain human clinical cervix samples that were assayed using microarrays (Example 3). Seventy-three of the probes are believed to be complementary to, and hybridize with, target RNA species that are expressed in human cells. Four of those 73 probes were also detected at elevated levels in certain human cervical cell lines that were assayed using microarrays (Example 1), and are also in Table 1 (836-R4-1, 3371-L4-1, 9053-R3-1, and 9691-L4-1). The remaining 19 probes are complementary to, and hybridize with, publicly known microRNAs that have been deposited by others into miRBase (http://microrna.sanger.ac.uk/; see Griffiths-Jones S. et al. (2007) Nucl. Acids Res. 36:154-158). One of those 19 probes was also detected at elevated levels in certain human cervical cell lines that were assayed using microarrays (Example 1), and is also in Table 1 (miR-765). To the knowledge of the inventors, at least 11 of those microRNAs, miR-1246, miR-1290, miR-1308, miR-1826, miR-200c, miR-451, miR-483-5p, miR-491-3p, miR-494, miR-720, and miR-765 have not been disclosed to have utility for detecting cervical dysplasia.

Table 28, below, lists 44 microRNAs that may be present at elevated levels in certain human cervical cancer cells lines and/or human clinical cervix samples. Some microRNAs in Table 28 are isomirs of one another. In some embodiments, two isomirs have a common core sequence with one or both ends varying by one to three nucleotides. For example, AGCCGCTCTTCTCCCTGCCCACA (SEQ ID NO: 355) and AGCCGCTCTTCTCCCTGCCCACA (SEQ ID NO: 356) are isomirs. Similarly, CCCGGAGAGCGGAGCACAACACA (SEQ ID NO: 346) and CCGGAGAGCGGAGCACACAAC (SEQ ID NO: 347) are isomirs. When multiple isomirs are listed in Table 28, one or more than one of the isomirs may be present at elevated levels in a cervical dysplasia. In some embodiments, a method comprises detecting multiple isomirs with a single probe. Detection of an elevated level of one or multiple isomirs is considered to be indicative of cervical dysplasia.

For convenience of reference herein, and not by way of limitation, some "target RNA" species are denominated "microRNAs" in the tables set forth herein and Example 1. In some embodiments, the target RNA is a single mature microRNA capable of specifically hybridizing to a hybridization probe set forth in Table 1 or Table 11. In some embodiments, a target RNA is a single mature microRNA that comprises a sequence that is complementary to at least 15 contiguous nucleotides of a sequence selected from SEQ ID NO.:1 to 41 and 133 to 211. In some embodiments, a target RNA is a single mature microRNA that comprises at least 15 contiguous nucleotides of a sequence selected from SEQ ID NOs: 345 to 388. In some embodiments, target RNA may include a plurality of target RNAs, all of which are capable of specifically hybridizing to a single complementary probe sequence (for example, when two or more target microRNAs are isomirs). In some embodiments, the so-denominated "microRNA" is one or more RNA species capable of specifically hybridizing to the respective hybridization probe, such that one or more target RNAs do not meet canonical definitions for mature microRNAs. In some embodiments, a target RNA is an mRNA.

Mature human microRNAs are typically composed of 17-27 contiguous ribonucleotides, and often are 21 or 22 nucleotides in length. The sequences of some target microRNAs that can be detected in accordance with the present disclosure can be found within the pre-microRNA sequences shown in Table 2 (SEQ ID NOs: 42 to 82) and Table 12 (SEQ ID NOs: 226 to 314). The sequences of some microRNAs are shown in Table 28. Further, in some embodiments, a microRNA comprises at least 10, at least 11, at least 12, at least 13, at least 14, at least 15, at least 16, at least 17, at least 18, at least 19, at least 20, at least 21, at least 22, at least 23, at least 24, at least 25, or at least 26 contiguous nucleotides of a sequence in Table 28 (SEQ ID NOs: 345 to 388). The sequences of the 23 publicly known mature microRNAs, obtained by query of miRBase, are also shown below in Table 3, along with the sequences of other previously known microRNAs that, in some embodiments, can be detected in the methods described herein.

While not intending to be bound by theory, mammalian microRNAs mature as described herein. A gene coding for a microRNA is transcribed, leading to production of a microRNA precursor known as the "pri-microRNA" or "pri-miRNA." The pri-miRNA can be part of a polycistronic RNA comprising multiple pri-miRNAs. In some circumstances, the pri-miRNA forms a hairpin with a stem and loop, which may comprise mismatched bases. The hairpin structure of the pri-miRNA is recognized by Drosha, which is an RNase III endonuclease protein. Drosha can recognize terminal loops in the pri-miRNA and cleave approximately two helical turns into the stem to produce a 60-70 nucleotide precursor known as the "pre-microRNA" or "pre-miRNA." Drosha can cleave the pri-miRNA with a staggered cut typical of RNase III endonucleases yielding a pre-miRNA stem loop with a 5' phosphate and an approximately 2-nucleotide 3' overhang. Approximately one helical turn of the stem (about 10 nucleotides) extending beyond the Drosha cleavage site can be essential for efficient processing. The pre-miRNA is subsequently actively transported from the nucleus to the cytoplasm by Ran-GTP and the export receptor Exportin-5.

The pre-miRNA can be recognized by Dicer, another RNase III endonuclease. In some circumstances, Dicer recognizes the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and an approximately 2-nucleotide 3' overhang. The resulting siRNA-like duplex, which may comprise mismatches, comprises the mature microRNA and a similar-sized fragment known as the microRNA*. The microRNA and microRNA* may be derived from opposing arms of the pri-miRNA and pre-miRNA. The mature microRNA is then loaded into the RNA-induced silencing complex ("RISC"), a ribonucleoprotein complex. In some cases, the microRNA* also has gene silencing or other activity.

TABLE 1

| Array probe | Array probe sequence (5' to 3', without linker) | SEQ ID NO: | fold-changes vs. normal Cervix | | | | | | |
|---|---|---|---|---|---|---|---|---|---|
| | | | CaSki HPV16 | SiHa HPV16 | sw756 HPV18 | C4-I HPV18 | C4-II HPV18 | ME180 HPV68 metastasis | C33A HPV neg |
| 3371-L4-1 | TTTCCTTTCCTCCCCTCCACACCCCATGACTCCCCACACTTGAG | 1 | 6.14 | 8.9 | 6.9 | 5.43 | 12.37 | 4.94 | 12.18 |
| 4315_D-R4-1 | GGAAAGTCAGCCCCCAGCGCCCCCCGGAGTTCTTGG | 2 | 6.91 | 4.11 | 3.25 | 7.01 | 12.19 | 8.37 | 14.35 |
| 4988-R4-1 | CTCCTCCTCCCCGTCTTTGGATACCAAACACTGGAC | 3 | 3.46 | 2.72 | 2.89 | 4.59 | 6.32 | 4.15 | 10.48 |
| 6647-R2-1 | CTCAGCCCCAGCTGGAGAATTTTTCCCCTCATTA | 4 | 4.49 | 5.48 | 4.91 | 3.05 | 8.35 | 2.42 | 4.16 |
| 9053-R3-1 | TTCTTGCCCTCCAATCCCCGGGCTCCACCAGCC | 5 | 5.40 | 2.51 | 3.69 | 5.76 | 10.31 | 5.55 | 24.91 |
| 6803-R3-1 | GCTCCCTCTCTGGTTGGACCTCACCCAAAGAT | 6 | 2.68 | 2.00 | 2.14 | 3.86 | 5.38 | 4.19 | 19.50 |
| 9691-L4-1 | AATCATCCATTTCATCCGCATCTCCCTCTTGGCCCCTTGC | 7 | 2.83 | 2.74 | 2.49 | 3.82 | 4.69 | 5.30 | 11.57 |
| miR-423-5p | AAAGTCTCGCTCTCTGCCCCTCA | 8 | 4.53 | 3.01 | 2.89 | 5.15 | 7.27 | 5.86 | 11.22 |
| 6584-L1-1 | TCGGCCCTGCCTCCTCCTCCT | 9 | 2.16 | 1.9 | 1.9 | 2.69 | 5.23 | 2.36 | 4.03 |
| 7421-R2-1 | TAAAGAGACTTCCTCCACTGCCAGAGATCT | 10 | 2.46 | 3.01 | 2.99 | 1.5 | 3.32 | 2.41 | 3.5 |
| 8016-L3-1 | TCAGCGCAACAAGCCCCGCAGTCACCCCTCT | 11 | 3.31 | 1.8 | 1.8 | 3.41 | 5.71 | 3.74 | 9.14 |
| 8433-L3-1 | AAATGGCTCCTTTCCCCTTTCCCTCCACCG | 12 | 2.40 | 2.60 | 1.6 | 2.68 | 4.59 | 2.61 | 5.71 |
| 4361-R3-1 | CGTCTCCCTCCCTCATGTGC | 13 | 2.21 | 2.84 | 2.67 | — | 4.72 | 3.52 | 10.04 |
| 10010_H-L4-1 | ACAGGCTACTTTCAGCAAATATGTCCATCCT | 14 | 3.67 | 3.56 | 1.6 | 2.92 | 4.44 | — | 3.1 |
| 12223-L4-1 | CCCAGAAGACATCAGACAGAGTTGTTTCTTCTCCCTCTA | 15 | — | 2.62 | 2.56 | 3.73 | — | — | 24.42 |
| 4610-R3-1 | GCCCTCTGGCCCCTGCCTAATTGGCTGC | 16 | 1.8 | — | 1.6 | 2.2 | 3.56 | 2.99 | 6.81 |
| 5192-L3-2 | CATTTTTCCCCTTCCTTCCTCTATATCAGCAA | 17 | 5.45 | 5.05 | 7.11 | — | 7.21 | 2.99 | 6.59 |
| 5782-L3-1 | GATTCCAGCCCCTTCCCCC | 18 | — | 2.20 | 1.5 | 2.57 | — | 2.84 | 5.04 |
| 5836-R3-2 | CATTAACCCCCATTATCACAGCACGCCCCATTC | 19 | 2.05 | 7.58 | — | — | — | 2.61 | 2.97 |
| 6183-R3-1 | GATTCCACTTTTCTTAATGACTTTCCCCTCCT | 20 | 2.68 | 2.12 | 2.72 | — | — | — | 2.74 |
| 6287-L3-2 | GCCCCGCCCCACCTTTCGGGGCTCACCTGGC | 21 | 2.20 | — | 1.5 | 2.70 | 4.43 | 4.42 | 5.90 |
| 6522-L3-1 | GGGTTGCCTCTAATGTGGTAATAGATGTCATT | 22 | — | 2.58 | 0.9 | — | 4.69 | 2.78 | 3.76 |
| 6752-R1-1 | CCCTCCTTTCCCCACCTCAGT | 23 | — | 3.58 | 2.99 | 2.66 | 5.44 | 2.26 | 5.13 |
| 6825-R3-1 | CTCAGCTGTTCCCGGTGCCAG | 24 | — | — | — | 2.13 | 5.17 | 2.68 | 2.94 |
| 6930-R3-1 | ATTAATCCTTCTCTCCCCTCTG | 25 | — | 3.12 | 2.52 | 5.01 | 5.16 | 5.17 | 20.54 |
| 7352-R3-2 | GCCCCTGCCAGAATCCTCTAACAGCTCTAATTGG | 26 | — | — | 1.6 | 4.29 | 5.18 | 14.54 | 8.13 |
| 7356-L2-1 | ACCGCGACATAGCCTCGCCCCC | 27 | 2.14 | 1.9 | — | 2.46 | 4.60 | 2.76 | 5.57 |
| 7384-R3-1 | CTCGCAAAGGATCTCCTTCATCCCTCCCCA | 28 | — | 2.26 | 0.7 | 1.7 | 3.27 | 2.18 | 3.96 |
| 7764-R3-2 | CCCTCTCTGCCTCTCTCATCACCAATAACAGAC | 29 | — | 2.15 | 2.12 | 2.41 | 4.33 | 3.00 | 7.07 |
| 8075-L3-1 | CCCAGCTACACCTCCACGCA | 30 | 2.90 | — | 2.67 | 4.02 | 5.12 | — | 2.8 |
| 8316-R3-1 | ATCAGGGTATCCTCTCCCCA | 31 | — | — | 1.5 | 2.59 | 2.84 | 2.46 | 9.39 |
| 836-R4-1 | AAATAATCATTCCAAATGGTTCTCCCTGCTATGATTCAC | 32 | 2.56 | 3.24 | 2.25 | — | — | 3.60 | 15.95 |

TABLE 1-continued

| Array probe | Array probe sequence (5' to 3', without linker) | probe SEQ ID NO: | fold-changes vs. normal Cervix | | | | | | |
|---|---|---|---|---|---|---|---|---|---|
| | | | CaSki HPV16 | SiHa HPV16 | sw756 HPV18 | C4-I HPV18 | C4-II HPV18 | ME180 HPV68 metastasis | C33A HPV neg |
| 8433_D-R4-1 | CCCGAGCCCGGCGCCCTGTGTTGTGCTCCGCTCTCC-GGGAAATGCCATCACTAAT | 33 | 2.89 | 2.08 | — | 3.53 | 6.19 | 3.10 | 8.85 |
| 8724-R3-1 | GCCAAGCTTGGAACCTCTCCCTGCCAGCATCAC | 34 | — | 1.6 | 1.7 | 3.31 | 3.92 | 3.60 | 11.08 |
| 8832-R4-1 | TCTGGAGTACCACCTGTTTTTCCCCCACT | 35 | — | 6.56 | 2.25 | — | 4.55 | 2.21 | 2.7 |
| 9349-R3-1 | GTGATGCAGAGGACTTCCTGCTCCAGGTCTC | 36 | 2.10 | 3.02 | 1.5 | 1.9 | — | 2.80 | 9.84 |
| 9733-L3-1 | AAGGCTGTCCCTCACCAGACTTCCCCACCCCT | 37 | — | 2.50 | 1.5 | 2.23 | 4.46 | 4.20 | 4.09 |
| miR-663 | GCGGTCCCGCGGCGCCCCGCCT | 38 | 2.59 | — | — | 3.09 | 4.55 | 3.99 | 6.49 |
| miR-765 | CATCACCTTCCTTCTCCTCCA | 39 | 2.48 | — | 3.16 | 3.42 | 5.46 | 2.96 | 21.76 |
| miR-92b* | CACTGCACCGCGTCCCGTCCCT | 40 | 2.06 | 2.17 | 1.8 | — | 4.64 | 3.35 | 7.45 |
| miR-936 | CTGCGATTCCTCCCTCTACTGT | 41 | — | 2.87 | 2.27 | — | 3.82 | 3.03 | 6.42 |

TABLE 2

| Pre-micro-RNA Candidate | chrom. Location | Pre-microRNA sequences | pre-micro RNA SEQ ID NO: |
|---|---|---|---|
| 03371-L | 18q21.33 | CTCAAGTGTGGGGAGTCATGGGGTGTGGAGGGGAGGAAAGGAAAGGTATTTTGTTTCTTTGTCTATACATTTCCTAGATTTCTATGCAGTTGGG | 42 |
| 12694-R | 1q22 | GGGGACGTGGCCCCTCCCCCCCGGAGCGGGACTCCAAGAACTCCGGGGGGCGCTGGGGGCTGACTTTCC | 43 |
| 04988-R | 14q24.3 | CTTTTTCTCTCTGCTGGGAAACCTTGCTTGACTTCATGTCCAGTGTTTGGTATCCAAAGACGGGGAGGAGGAG | 44 |
| 06647-R | 1q23.3 | CTCAGTATCTTCAGCTTGGGAAACTGACCTCGTTAATTTTAATGAGGGGAAAAATTCTCCAGCTGGGGCTGAG | 45 |
| 09053-R | Xq27.3 | GGAAGGGCACTGTCTCTCTGATTCCCAGGGCCTGTCATTTCCCGAGGGCTGGTGGAGCCCGGGGATTGGAGGGCAAGAAGCCCAGCC | 46 |
| 06803-R | 22q12.3 | GCCACCTTTCATGGTGAGGATGCCTGCCACCTTCAGGATCACATCTTTGGGTGAGGTCCAACCAGAGAGGGAGC | 47 |
| 09691-L | 14q24.3 | GCAAGGGGCCAAGAGGGAGATGCGGATGAAATGGATGATTTAATGGGTCATCTCTCCTGTAGTTAATTTCTCTAGATCTCTTGT | 48 |
| miR-423-5p | 17q11.22 | ATAAAGGAAGTTAGGCTGAGGGGCAGAGAGCGAGACTTTTCTATTTTCCAAAAGCTCGGTCTGAGGCCCCTCAGTCTTTGCTCCTAACCCGCGC | 49 |
| 06584-L | 12q24.23 | GCTTGGTGAGAGGAGGAGGAGGCAGGGCCGACCGCCACCCGCCTGTCTGCCATCTGGTCCCCTTCCCCTCCCTCCTCTCATTGC | 50 |
| 07421-R | 12p13.31 | TGAAGAATTTCTTCTGGATGACTGACCAAGAGGCTATTCAAGATCTCTGGCAGTGGAGGAAGTCTCTTTA | 51 |
| 08016-L | 12q21.1 | AGAGGGGTGACTGCGGGGCTTGTTGCGCTGAAGATTTACAATGTACTTCTTGCAGGCGGCTCAGCAACCCCCTCT | 52 |
| 08433-L | 17q25.3 | CGGTGGAGGGAAAGGGAAAGGAGCCATTTTCTGCTGCACATCAGTCAGTGCCTGCGCCCTCCCTCCCTCCGCCG | 53 |
| 04361-R | Xp11.22 | TGCTGGAGGTAAGGGTTTTCTGAAGCCTGGTGCCATGGCCACATGTGCACATGAGGGAGGGAGAGCGCTGAGGCTAGCA | 54 |
| 12709-L | 7q32.1 | AGGATGGACATATTTGCTGAAAGTAGCCTGTGCATTAATTGGTTATGGAAGTTTAAAAATGGTGTCCTCCT | 55 |
| 12223-L | 4q27 | TAGAGGGAGAAGAAACAACTCTGTCTGATGTCTTCTGGGATGGCCTTAATACAGATAGCATTGTCTCTTCCATTTCTG | 56 |
| 04610-R | 8p12 | GCCCAGTTAATTGGTCTCTCAACCTACATTAGCTGTTGCATTGCAGCCAATTAGGCAGGGGCCAGAGGGC | 57 |
| 05192-L | 5q34 | GTCTTTGCTGATATAGAGGAAGGAAGGGGAAAAATGAGCGCATTAGTTCTCTTTTATTAAAAGAGTTATTTCAGCATGAC | 58 |
| 05782-L | 5q35.1 | GGGGGAAGGGGCTGGAATCATCGTGGGTTGGAACAGTTAAAGGAACCTCTGTTCAGCCCCAGCCCCAAGGCTCCC | 59 |
| 05836-R | 11q23.3 | GCCATGGGCCTCCATAGTTTCCTGTAGCCCCCTTGGTTCCCAAGAATAGTTTTGGAATGGGCGTGCTGTGATAATGGGGGTTAATGGT | 60 |

TABLE 2-continued

| Pre-microRNA Candidate | chrom. Location | Pre-microRNA sequences | pre-microRNA SEQ ID NO: |
|---|---|---|---|
| 06183-R | 12q21.33 | GATTCATCTATTCTTTTTCTCCTTCTTCAAAGATAACTCTGTAAGCACTTAAGGAGGGGAAAGTCATTAAGAAAAGTGGAATC | 61 |
| 06287-L | 1p34.1 | AGCAGCCAGGTGAGCCCCGAAAGGTGGGGCGGGGCAGGGGCGCTCCCAGCCCCACCCCGGGATCTGGTGACGCT | 62 |
| 06522-L | 5q23.2 | AATGACATCTATTACCACATTAGAGGCAACCCATAACAATCCCTTATAGAATGTTTGTCTCAATTTTGGTTATTTAATGTCATT | 63 |
| 06752-R | Xq13.1 | CCCTCCCAGTTCCCATAGCAACTGGGCTGTAGCAGCCAGAACTTGATTGAGCCCAGCAGTGGCCCGACTGAGGTGGGGAAAGGAGGG | 64 |
| 06825-R | 9q31.1 | CAAATTACATCTGTTTATGCTTCTATTTGTTAGACAATCTGGCACCGGGAACAGCTGAGCAGAAGGATTTG | 65 |
| 06930-R | 9p21.3 | TGTCATTTGTCCATTTTCTCTTCTGACCCAGTGGTATTCTGCAAGATCAGAGGGGAGAGAAGGATTAATGTCA | 66 |
| 07352-R | 1q25.2 | GCCTCTGTGCGCATGGATATAATCAGCTTTGATAGGCAGAGGCTGAGGCTGTTTTTCCAATTAGAGCTGTTAGAGGATTCTGGCAGGGGC | 67 |
| 07356-L | 8q24.3 | GGGGGCGAGGCTATGTCGCGGTGGCAGCCCGGATGGGCCGGCAGGGCCGGGAGTAACGGGACGTCGCCGCGGAGCTTCTTCCCCC | 68 |
| 07384-R | 12g12 | GGCATTTCTTCTTGTGTTTCCTCTTCTCCTCTTCTGGGGAGGGATGAAGGAGATCCTTTGCGAGAGGCATGTT | 69 |
| 07764-R | 5q11.2 | TGCTATCTCGCCTCACACATCAACACACGTGCCAGACAGATTCTGACTGCAAAGTCTGTTATTGGTGATGAGAGAGGCAGAGAGGGCA | 70 |
| 08075-L | 10q22.1 | CAGCTGGCCTGGTGCCCTGGTGCGTGGAGGTGTAGCTGGGCTCTGACCCAGCTCCTCAAACAGGTTCCATATGGCCCTCCCGGCTG | 71 |
| 08316-R | 14q24.3 | GTCAGGCTGCTGTATTCTCTTACACAGATGCCAGTAAGAACAAAGGCATCACGTGGGGAGAGGATACCCTGAT | 72 |
| 00836-R | 3q26.2 | AAATAAGCCATTCCAAACCATTCTCTGATTTGCTGTGAGTGGCAGAATCATTCACCGTGGTGAATCATAGCAGGGAGAACCATTTGGAATGATTATTT | 73 |
| 12730-R | 17q25.3 | CCCGGCTCGGCCCCGCGTCTCTCCAGCTCCTCCGGCTCCTTTTAGTGCATAAATTAGTGATGGCATTTCCCGGAGA-GCGGAGCACAACACAGGGCGCGGGCTCGGG | 74 |
| 08724-R | 15q23 | GGCCCAGAAGATGAAAAGCTGAAGTCCTTTCCCTTCCAGCTGAAGCCAGGTGTGATGCTGGCAGGGAGAGGTTCCAAGCTTGGCC | 75 |
| 08832-R | 9q33.2 | TTCTGAGATATGATCTGTTGGATTCTCTACTACCAAAGTGGGGGAAAAACAGGTGGTACTCCAGAA | 76 |
| 09349-R | 21q22.11 | GGACACTCTGAACCCCAAGTGGAATTCCAACTGCCAGTTCTTCATCCGAGACCTGGAGCAGGAAGTCCTCTGCATCACTGTGTTC | 77 |
| 09733-L | 15q23 | AGGGGTGGGGAAGTCTGGTGAGGGACAGCCTTGAGTCAAAGGATGGTCACCGCTCCATGTGGCTGCCCCACCCCT | 78 |
| miR-663 | 20p11.1 | CCTTCCGGCGTCCCAGGCGGGGCGCCGCGGGACCGCCCTCGTGTCTGTGGCGGTGGGATCCCGCGGCCGTGTTTTCC-TGGTGGCCCGGCCATG | 79 |
| miR-765 | 1q23.1 | TTTAGGCGCTGATGAAAGTGGAGTTCAGTAGACAGCCCTTTTCAAGCCCTACGAGAAACTGGGGTTTCTGGAGG-AGAAGGAAGGTGATGAAGGATCTGTTCTCGTGAGCCTGAA | 80 |
| miR-92b*1 | | CGGGCCCCGGGCGGGCGGGAGGGACGGGACGCGGTGCAGTGTTGTTTTTTCCCCCGCCAATATTGCACTCGTCCCGGCCTCCGGCCCCCCGGCCC | 81 |
| miR-936 | 10q25.1 | TCAAGGCCACTGGGACAGTAGAGGGAGGAATCGCAGAAATCACTCCAGGAGCAACTGAGAGACCTTGCTTCTACTTTACCAGGTCCTGCTGGCCCAGA | 82 |

| TABLE 3 | | |
|---|---|---|
| SEQ ID NO | microRNA | Mature microRNA Sequences (5' to 3') sequence |
| 91 | miR-423-5p (miR-423) | UGAGGGGCAGAGAGCGAGACUUU |
| 92 | miR-663 | AGGCGGGGCGCCGCGGGACCGC |
| 93 | miR-765 | UGGAGGAGAAGGAAGGUGAUG |
| 94 | miR-92b* | AGGGACGGGACGCGGUGCAGUG |
| 95 | miR-936 | ACAGUAGAGGGAGGAAUCGCAG |

TABLE 3-continued

| SEQ ID NO | microRNA | Mature microRNA Sequences (5' to 3') sequence |
|---|---|---|
| 389 | miR-1246 | AAUGGAUUUUUGGAGCAGG |
| 390 | miR-1290 | UGGAUUUUUGGAUCAGGGA |
| 391 | miR-1308 | GCAUGGGUGGUUCAGUGG |
| 111 | miR-142-3p | UGUAGUGUUUCCUACUUUAUGGA |
| 392 | miR-1826 | AUUGAUCAUCGACACUUCGAACGCAAU |
| 393 | miR-195 | UAGCAGCACAGAAAUAUUGGC |
| 394 | miR-200c | UAAUACUGCCGGGUAAUGAUGGA |
| 395 | miR-451 | AAACCGUUACCAUUACUGAGUU |
| 396 | miR-483-5p | AAGACGGGAGGAAAGAAGGGAG |
| 397 | miR-491-3p | CUUAUGCAAGAUUCCCUUCUAC |
| 398 | miR-494 | UGAAACAUACACGGGAAACCUC |
| 399 | miR-720 | UCUCGCUGGGGCCUCCA |
| 400 | miR-98 | UGAGGUAGUAAGUUGUAUUGUU |
| 401 | miR-143 | UGAGAUGAAGCACUGUAGCUC |
| 100 | miR-145 | GUCCAGUUUUCCCAGGAAUCCCU |
| 402 | miR-205 | UCCUUCAUUCCACCGGAGUCUG |
| 109 | miR-21 | UAGCUUAUCAGACUGAUGUUGA |
| 403 | miR-31 | AGGCAAGAUGCUGGCAUAGCU |
| 96 | miR-9 | UCUUUGGUUAUCUAGCUGUAUGA |
| 97 | miR-199a* | ACAGUAGUCUGCACAUUGGUUA |
| 98 | miR-199a | CCCAGUGUUCAGACUACCUGUUC |
| 99 | miR-199b | CCCAGUGUUUAGACUAUCUGUUC |
| 101 | miR-133a | UUUGGUCCCCUUCAACCAGCUG |
| 102 | miR-133b | UUUGGUCCCCUUCAACCAGCUA |
| 103 | miR-214 | ACAGCAGGCACAGACAGGCAGU |
| 104 | miR-127 | CUGAAGCUCAGAGGGCUCUGAU |
| 105 | miR-210 | CUGUGCGUGUGACAGCGGCUGA |
| 106 | miR-182 | UUUGGCAAUGGUAGAACUCACACU |
| 107 | miR-183 | UAUGGCACUGGUAGAAUUCACU |
| 404 | miR-155 | UUAAUGCUAAUCGUGAUAGGGGU |
| 108 | miR-146a | UGAGAACUGAAUUCCAUGGGUU |
| 110 | miR-301 | CAGUGCAAUAGUAUUGUCAAAGC |
| 112 | miR-142-5p | CAUAAAGUAGAAAGCACUACU |
| 113 | miR-194 | UGUAACAGCAACUCCAUGUGGA |
| 114 | miR-215 | AUGACCUAUGAAUUGACAGAC |
| 115 | miR-32 | UAUUGCACAUUACUAAGUUGCA |
| 116 | miR-374b | AUAUAAUACAACCUGCUAAGUG |
| 117 | miR-933 | UGUGCGCAGGGAGACCUCUCCC |
| 118 | miR-769-3p | CUGGGAUCUCCGGGGUCUUGGUU |
| 119 | miR-671 | AGGAAGCCCUGGAGGGGCUGGAG |
| 120 | miR-934 | UGUCUACUACUGGAGACACUGG |
| 121 | miR-935 | CCAGUUACCGCUUCCGCUACCGC |
| 122 | miR-937 | AUCCGCGCUCUGACUCUCUGCC |
| 123 | miR-938 | UGCCCUUAAAGGUGAACCCAGU |
| 124 | miR-939 | UGGGGAGCUGAGGCUCUGGGGUG |
| 125 | miR-940 | AAGGCAGGGCCCCCGCUCCCC |
| 126 | miR-941 | CACCCGGCUGUGUGCACAUGUGC |
| 127 | miR-942 | UCUUCUCUGUUUUGGCCAUGUG |
| 128 | miR-943 | CUGACUGUUGCCGUCCUCCAG |
| 129 | miR-944 | AAAUUAUUGUACAUCGGAUGAG |
| 130 | miR-708 | AAGGAGCUUACAAUCUAGCUGGG |
| 131 | miR-874-5p | CGGCCCCACGCACCAGGGUAAG |
| 132 | miR-874-3p | CUGCCCUGGCCCGAGGGACCGA |

In Table 1, the expression levels of target RNAs measured for each of the identified sample cell lines are expressed as fold-changes in expression relative to expression levels measured in normal human cervix total RNA (see Example 1). The expression levels of the target RNAs detected by the probes in Table 11, expressed as fold-changes for each of the clinical cervix samples, are shown in Table 10 (Example 3).

In some embodiments, target RNAs can be measured in samples collected at one or more times from a patient to monitor the status or progress of cervical dysplasia in the patient.

In some embodiments, a sample to be tested is obtained using one or more techniques commonly used for preparing Pap smears, e.g., (i) endocervical swab, using a cotton applicator stick (or wire brush for endocervical specimens) advanced into the os of the cervix, with the stick gently rolled between the thumb and index finger; (ii) cervical scrape, in which the longer end of a cervical spatula is inserted into the os of the cervix and pressed gently, with turning and scraping. In some embodiments, the sample to be tested is a cervical biopsy, such as a punch biopsy or cone biopsy. In some embodiments, the sample to be tested is from a loop excision, or LEEP, procedure.

The clinical sample to be tested is, in some embodiments, freshly obtained. In other embodiments, the sample is a fresh frozen specimen. In some embodiments, the sample is a tissue sample, such as a formalin-fixed paraffin embedded sample. In some embodiments, the sample is a liquid cytology sample.

Exemplary liquid cytology preservative solutions include, but are not limited to, ThinPrep™ PreservCyt™ solution (Hologic, Bedford, Mass.) and SurePath™ preservative solution (BD Diagnostics, NJ). Additional exemplary preservative solutions include, but are not limited to, RNAlater® (Ambion), formalin (e.g., 10% aqueous formalin), Universal Viral Transport Media (BD Diagnostics, NJ), M4, M4RT, PVA (polyvinyl-alcohol), PolyCyte (American Mastertech Scientific), Spray-Cyte cytological fixative (Becton- Dickinson), formaldehyde (e.g., 10% in phosphate buffer), NuFix Complete Collection Solution (QC Sciences), CarboFix (StatLab Medical Products), Cyto Jar (Surgipath Medical Industries), SED Fix (Surgipath Medical Industries), SprayFix (Surgipath Medical Industries), cytology fixative 50% alcohol solution (U.S. Biotex), Cyto-Prep (Wakefield), Cyto-Fix (Wakefield), PVA with zinc or copper, merthiolate-iodine-formaldehyde (MIF), sodium acetate-acetic acid-formalin (SAF), mercuric chloride-based Schaudinn's, zinc-based Schaudinn's preservative (Meridian Diagnostics, Inc.), EcoFix® (Merdian Bioscience), Parasafe®, Unifix, Proto-Fix™, and STF.

In some embodiments, the clinical sample to be tested is obtained in conjunction with routine cytologic screening (e.g., by Pap smear), currently recommended for all women between the ages of 21 and 65, and women who are under 21 years old who have been sexually active for three years or more. In some embodiments, the sample to be tested is obtained from a woman who has a predisposition to develop cervical cancer, e.g., a woman who has tested positive for HPV infection, and especially positive for a high risk HPV type. In some embodiments, the clinical sample to be tested is obtained from women who have one or more of the following risk factors: multiparous, many sexual partners, first sexual intercourse at a young age, smoke cigarettes, use of oral contraceptives, and a weakened immune system. In some embodiments, the clinical sample is obtained from women who have diagnostic signs or clinical symptoms that may be associated with cervical cancer, such as abnormal Pap tests, abnormal bleeding or visible cervical lesions.

In some embodiments, the methods described herein are used for early detection of cervical dysplasia in a sample of cervical cells, such as those obtained by routine Pap smear. In some embodiments, methods described herein can be used for early detection of cervical dysplasia in a sample of cervical cells, and to determine a likelihood that the detected cervical dysplasia will progress to cervical cancer.

Thus, in some embodiments, methods of the present disclosure can be used for routine screening of healthy women with no risk factors. In some embodiments, methods herein are used to (1) screen women who have a history of abnormal Pap smears and/or of assays showing infection by one or more HPV strains associated with the development of cervical cancer, (2) screen women with one or more of the above-described risk factors, (3) confirm a diagnosis made by cytology, histology or HPV assay, and/or further characterize a diagnosis made by cytology or histology.

In some embodiments, the methods described herein can be used to assess the effectiveness of a treatment for cervical cancer in a patient. In some embodiments, the target RNA expression levels are determined at various times during the treatment, and are compared to target RNA expression levels from an archival sample taken from the patient, e.g., by Pap smear, before the manifestation of any signs of cervical dysplasia or cervical cancer or before beginning treatment. Ideally, target RNA expression levels in the normal Pap smear sample evidence no aberrant changes in target RNA expression levels. Thus, in such embodiments, the progress of treatment of an individual with cervical dysplasia or cervical cancer can be assessed by comparison to a sample of cervical cells from the same individual when she was healthy or prior to beginning treatment.

In some embodiments, a target RNA is capable of specifically hybridizing to a nucleic acid comprising a sequence selected from SEQ ID NOs: 1, 2, 3, 4, 5, 6, 7 and 8. In some embodiments, a target RNA is capable of specifically hybridizing to a nucleic acid comprising a sequence selected from SEQ ID NOs: 1, 2, 3, 4, 5, 6, 7, 8, 9, 10, 11 and 12. In some embodiments, a target RNA is selected from miR-1246, miR-1308, miR-491-3p, miR-1826, and miR-1290 (SEQ ID NOs: 208, 210, 205, 211, and 209), and target RNAs that are capable of specifically hybridizing to probes 13254-R5-1, 13252-L5-3, 13532-L5-2, 4440-L3-2, 6216-L1-1, and 6235-R5-2 (SEQ ID NOs: 194, 193, 172, 142, 151, and 153). In some embodiments, a target RNA is capable of specifically hybridizing to a nucleic acid comprising a sequence selected from SEQ ID NOs: 1, 5, 7, and 32. In some embodiments, a target RNA is capable of specifically hybridizing to a nucleic acid comprising a sequence selected from SEQ ID NOs: 1 to 41 set forth in Table 1 and SEQ ID NOs: 133 to 211 in Table 11. In some embodiments, a target RNA comprises at least 15 contiguous nucleotides of a sequence selected from SEQ ID NOs: 345 to 388. In some embodiments, a target RNA comprises a sequence that is complementary to at least 15 contiguous nucleotides of a sequence selected from SEQ ID NOs: 1 to 41 and 133 to 211. In some embodiments, a target RNA, in its mature form, comprises fewer than 30 nucleotides. In some embodiments, a target RNA is a microRNA.

In embodiments in which the method comprises detecting expression of more than one target RNA, the expression levels of the plurality of target RNAs may be detected concurrently or simultaneously in the same assay reaction. In some embodiments, expression levels are detected concurrently or simultaneously in separate assay reactions. In some embodiments, expression levels are detected at different times, e.g., in serial assay reactions.

In some embodiments, a method comprises detecting the level of at least one target RNA in a sample from a subject, wherein detection of a level of at least one target RNA that is greater than a normal level of the at least one target RNA indicates the presence of cervical dysplasia in the sample and/or in the subject. In some embodiments, a method comprises detecting the level of at least one target RNA in a sample from a subject and comparing the level of the at least one target RNA in the sample to a normal level of the at least one target RNA, wherein a level of at least one target RNA in the sample that is greater than a normal level of the at least one target RNA indicates the presence of cervical dysplasia in the sample and/or in the subject.

In some embodiments, a method of facilitating diagnosis of cervical dysplasia in a subject is provided. Such methods comprise detecting the level of at least one target RNA in a sample from the subject. In some embodiments, information concerning the level of at least one target RNA in the sample from the subject is communicated to a medical practitioner. A "medical practitioner," as used herein, refers to an individual or entity that diagnoses and/or treats patients, such as a hospital, a clinic, a physician's office, a physician, a nurse, or an agent of any of the aforementioned entities and individuals. In some embodiments, detecting the level of at least one target RNA is carried out at a laboratory that has received the subject's sample from the medical practitioner or agent of the medical practitioner. The laboratory carries out the detection by any method, including those described herein, and then communicates the results to the medical practitioner. A result is "communicated," as used herein, when it is provided by any means to the medical practitioner. In some embodiments, such communication may be oral or written, may be by telephone, in person, by e-mail, by mail or other courier, or may be made by directly depositing the information into, e.g., a database accessible by the medical practitioner, including databases not controlled by the medical practitioner. In some embodiments, the information is maintained in electronic form. In some embodiments, the information can be stored in a memory or other computer readable medium, such as RAM, ROM, EEPROM, flash memory, computer chips, digital video discs (DVD), compact discs (CDs), hard disk drives (HDD), magnetic tape, etc.

In some embodiments, methods of detecting the presence cervical dysplasia are provided. In some embodiments, methods of diagnosing cervical dysplasia are provided. In some embodiments, the method comprises obtaining a sample from a subject and providing the sample to a laboratory for detection of at least one target RNA level in the sample. In some embodiments, the method further comprises receiving a communication from the laboratory that indicates the at least one target RNA level in the sample. In some embodiments, cervical dysplasia is present if the level of at least one target RNA in the sample is greater than a normal level of the at least one target RNA. A "laboratory," as used herein, is any facility that detects the level of at least one target RNA in a sample by any method, including the methods described herein, and communicates the level to a medical practitioner. In some embodiments, a laboratory is under the control of a medical practitioner. In some embodiments, a laboratory is not under the control of the medical practitioner.

When a laboratory communicates the level of at least one target RNA to a medical practitioner, in some embodiments, the laboratory communicates a numerical value representing the level of at least one target RNA in the sample, with or without providing a numerical value for a normal level. In some embodiments, the laboratory communicates the level of at least one target RNA by providing a qualitative value, such as "high," "elevated," etc.

As used herein, when a method relates to detecting cervical dysplasia, determining the presence of cervical dysplasia, and/or diagnosing cervical dysplasia, the method includes activities in which the steps of the method are carried out, but the result is negative for the presence of cervical dysplasia. That is, detecting, determining, and diagnosing cervical dysplasia include instances of carrying out the methods that result in either positive or negative results (e.g., whether target RNA levels are normal or greater than normal).

As used herein, the term "subject" means a human. In some embodiments, the methods described herein may be used on samples from non-human animals.

The common, or coordinate, expression of target RNAs that are physically proximal to one another in the genome permits the informative use of such chromosome-proximal target RNAs in methods herein.

Table 2 identifies the chromosomal location of each of the 41 target RNAs capable of specifically hybridizing to a nucleic acid comprising a sequence selected from SEQ ID NOs: 1 to 41 in Table 1. Table 12 identifies the chromosomal location of each of the target RNAs capable of specifically hybridizing to a nucleic acid comprising a sequence selected from SEQ ID NOs: 133 to 211 in Table 11. Thus, in some embodiments, the level of expression of one or more target RNAs located within about 1 kilobase (kb), within about 2 kb, within about 5 kb, within about 10 kb, within about 20 kb, within about 30 kb, within about 40 kb, and even within about 50 kb of the chromosomal locations in Table 2 and Table 12 is detected in lieu of, or in addition to, measurement of expression of the respective tabulated target RNA in the methods described herein. See Baskerville, S. and Bartel D. P. (2005) RNA 11:241-247.

In some embodiments, in combination with detecting one or more target RNAs capable of specifically hybridizing to a nucleic acid comprising a sequence selected from SEQ ID NOs:1 to 41 and 133 to 211 and/or detecting one or more target RNAs comprising at least 15 contiguous nucleotides of a sequence selected from SEQ ID NOs: 345 to 388 and/or detecting one or more target RNAs that comprise a sequence that is complementary to at least 15 contiguous nucleotides of a sequence selected from SEQ ID NOs:1 to 41 and 133 to 211, methods herein further comprise detecting the level(s) of expression of at least one microRNA selected from miR-21, miR-31, miR-182, miR-183, miR-155, miR-9, miR-199a*, miR-199a, miR-199b, miR-205, miR-145, miR-133a, miR-133b, miR-214, miR-127, miR-210, miR-146a, miR-301, miR-142-5p, miR-194, miR-215, miR-32, miR-374b, miR-933, miR-769-3p, miR-671, miR-934, miR-935, miR-937, miR-938, miR-939, miR-940, miR-941, miR-942, miR-943, miR-944, miR-708, miR-874-5p, and miR-874-3p. In some embodiments, an increase in expression of one or more of these microRNAs, in combination with an elevated level of one or more target RNAs capable of specifically hybridizing to a nucleic acid comprising a sequence selected from SEQ ID NOs:1 to 41 and 133 to 211 and/or an elevated level of one or more target RNAs comprising at least 15 contiguous nucleotides of a sequence selected from SEQ ID NOs: 345 to 388 and/or an elevated level of one or more target RNAs that comprise a sequence that is complementary to at least 15 contiguous nucleotides of a sequence selected from SEQ ID NOs:1 to 41 and 133 to 211, is indicative of the presence of cervical dysplasia in a sample of human cervical cells.

In some embodiments, in combination with detecting one or more target RNAs capable of specifically hybridizing to a nucleic acid comprising a sequence selected from SEQ ID NOs:1 to 41 and 133 to 211 and/or detecting one or more target RNAs comprising at least 15 contiguous nucleotides of a sequence selected from SEQ ID NOs: 345 to 388 and/or detecting one or more target RNAs that comprise a sequence that is complementary to at least 15 contiguous nucleotides of a sequence selected from SEQ ID NOs:1 to 41 and 133 to 211, methods herein further comprise detecting in a sample of human cervical cells the expression of at least one microRNA selected from miR-9, miR-199a*, miR-199a, miR-199b, miR-145, miR-133a, miR-133b, miR-214 and miR-127 where invasive squamous cell cervical carcinoma is implicated. In some embodiments, an increase in expression of one or more microRNAs selected from miR-9, miR-199a*, miR-199a, miR-199b, miR-145, miR-133a, miR-133b, miR-214 and miR-127, in combination with an elevated level of one or more target RNAs capable of specifically hybridizing to a nucleic acid comprising a sequence selected from SEQ ID NOs:1 to 41 and 133 to 211 and/or an elevated level of one or more target RNAs comprising at least 15 contiguous nucleotides of a sequence selected from SEQ ID NOs: 345 to 388 and/or an elevated level of one or more target RNAs that comprise a sequence that is complementary to at least 15 contiguous nucleotides of a sequence selected from SEQ ID NOs:1 to 41 and 133 to 211, is indicative of the presence of cervical carcinoma in a sample of human cervical cells.

In some embodiments, in combination with detecting one or more target RNAs capable of specifically hybridizing to a nucleic acid comprising a sequence selected from SEQ ID NOs:1 to 41 and 133 to 211 and/or detecting one or more target RNAs comprising at least 15 contiguous nucleotides of a sequence selected from SEQ ID NOs: 345 to 388 and/or detecting one or more target RNAs that comprise a sequence that is complementary to at least 15 contiguous nucleotides of a sequence selected from SEQ ID NOs:1 to 41 and 133 to 211, methods herein further comprise detecting in a sample of human cervical cells the expression of at least one microRNA selected from miR-210, miR-182 and miR-183 where human papilloma virus 16 ("HPV-16") is implicated. In some embodiments, an increase in expression of one or more of miR-210, miR-182 and miR-183, in combination with an elevated level of one or more target RNAs capable of specifically hybridizing to a nucleic acid comprising a sequence selected from SEQ ID NOs:1 to 41 and 133 to 211 and/or an elevated level of one or more target RNAs comprising at least 15 contiguous nucleotides of a sequence selected from SEQ ID NOs: 345 to 388 and/or an elevated level of one or more target RNAs that comprise a sequence that is complementary to at least 15 contiguous nucleotides of a sequence selected from SEQ ID NOs:1 to 41 and 133 to 211, is indicative of HPV16 infection in a sample of cervical cells.

In some embodiments, in combination with detecting one or more target RNAs capable of specifically hybridizing to a nucleic acid comprising a sequence selected from SEQ ID NO.:1 to 41 and 133 to 211 and/or detecting one or more target RNAs comprising at least 15 contiguous nucleotides of a sequence selected from SEQ ID NOs: 345 to 388 and/or detecting one or more target RNAs that comprise a sequence that is complementary to at least 15 contiguous nucleotides of a sequence selected from SEQ ID NOs:1 to 41 and 133 to 211, methods herein further comprise detecting in a sample of human cervical cells the expression of miR-146a in order to distinguish cervical cancer from pre-neoplastic lesions, e.g., HPV-infected cervical cells.

In some embodiments, a target RNA, in its mature form, comprises fewer than 30 nucleotides. In some embodiments, a target RNA is a microRNA.

In some embodiments, the methods further comprise detecting in a sample of human cervical cells the expression of at least one target RNA gene located in close proximity to chromosomal features, such as cancer-associated genomic regions, fragile sites, and human papilloma virus integration sites.

In some embodiments, in combination with detecting one or more target RNAs capable of specifically hybridizing to a nucleic acid comprising a sequence selected from SEQ ID NOs:1 to 41 and 133 to 211 and/or detecting one or more target RNAs comprising at least 15 contiguous nucleotides of a sequence selected from SEQ ID NOs: 345 to 388 and/or detecting one or more target RNAs that comprise a sequence that is complementary to at least 15 contiguous nucleotides of a sequence selected from SEQ ID NOs:1 to 41 and 133 to 211, methods herein further comprise detecting in a sample of human cervical cells the expression of at least one mRNA species. In some embodiments, the at least one mRNA is selected from the mRNAs for the genes set forth in Table 4, below. In some embodiments, at least one mRNA is selected from mRNAs for CDKN2A, MKI67, TOP2A, and MCM5. In some embodiments, at least one mRNA is selected from mRNAs for CDKN2A, MKI67, TOP2A, MCM5, BIRC5, MMP9, and MCM2.

TABLE 4

| gene | name | alias |
|---|---|---|
| BIRC5 | survivin | survivin |
| IGF2BP3 | insulin-like growth factor 2 mRNA binding protein 3 | L523S, IMP-3, KOC1 |

TABLE 4-continued

| gene | name | alias |
|---|---|---|
| TERC | telomerase RNA component | hTR |
| CDKN2A | cyclin-dependent kinase inhibitor 2A | P16$^{ink4}$ |
| MCM5 | minichromosome maintenance complex component 5 | — |
| TOP2A | topoisomerase II-α | |
| MYBL2 | v-myb myeloblastosis viral oncogene homolog (avian)-like 2 | B-myb |
| PIK3CA | phosphoinositide-3-kinase, catalytic, alpha polypeptide | PI3K |
| DROSHA | class 2 RNase III enzyme that initiates processing of microRNA | Drosha, Rnasen |
| MKI67 | antigen identified by monoclonal antibody Ki-67 | Ki-67 |
| MMP9 | matrix metallopeptidase 9 | gelatinase B, 92 kDa gelatinase, 92 kDa type IV collagenase |
| MCM2 | minichromosome maintenance complex component 2 | |

In some embodiments, an increase in expression of one or more mRNAs listed in the table above is indicative of the presence of cervical dysplasia or cervical cancer in a sample of human cervical cells.

In some embodiments, more than one target RNA is detected simultaneously in a single reaction. In some embodiments, at least 2, at least 3, at least 5, or at least 10 target RNAs are detected simultaneously in a single reaction. In some embodiments, all target RNAs are detected simultaneously in a single reaction.

4.1.2. Exemplary Controls

In some embodiments, a normal level (a "control") for each target RNA can be determined as an average level or range that is characteristic of normal cervical cells or other reference material, against which the level measured in the sample can be compared. The determined average or range of target RNA in normal subjects can be used as a benchmark for detecting above-normal levels of target RNA indicative of cervical dysplasia. In some embodiments, normal levels of target RNA can be determined using individual or pooled RNA-containing samples from one or more individuals, such as from patients undergoing hysterectomy for benign gynecologic disease.

In some embodiments, determining a normal level of expression of a target RNA comprises detecting a complex comprising a probe hybridized to a nucleic acid selected from a target RNA, a DNA amplicon of the target RNA, and a complement of the target RNA. That is, in some embodiments, a normal level of expression can be determined by detecting a DNA amplicon of the target RNA, or a complement of the target RNA rather than the target RNA itself. In some embodiments, a normal level of such a complex is determined and used as a control. The normal level of the complex, in some embodiments, correlates to the normal level of the target RNA. Thus, when a normal level of a target is discussed herein, that level can, in some embodiments, be determined by detecting such a complex.

In some embodiments, a control comprises RNA from cells of a single individual, e.g., a patient undergoing hysterectomy for benign gynecologic disease. In some embodiments, a control comprises RNA from a pool of cells from multiple individuals. In some embodiments, a control is drawn from anatomically and/or cytologically normal areas of the cervix of the individual from whom the test sample was obtained. In some embodiments, a control comprises commercially-available human RNA, such as, for example, human cervix total RNA (Ambion; AM6992). In some embodiments, a normal level or normal range has already been predetermined prior to testing a sample for an elevated level.

In some embodiments, the normal level of target RNA can be determined from one or more continuous cell lines, typically cell lines previously shown to have expression levels of the at least one target RNA that approximate the level of expression in normal cervical cells.

In some embodiments, a method comprises detecting the level of expression of at least one target RNA. In some embodiments, a method further comprises comparing the level of expression of at least one target RNA to a normal level of expression of the at least one target RNA. In some embodiments, a method further comprises comparing the level of expression of at least one target RNA to a control level of expression of the at least one target RNA. A control level of expression of the at least one target RNA is, in some embodiments, the level of expression of the at least one target RNA in a normal cell. In some such embodiments, a control level may be referred to as a normal level. In some embodiments, a greater level of expression of the at least one target RNA relative to the level of expression of the at least one target RNA in a normal cell indicates cervical dysplasia.

In some embodiments, the level of expression of the at least one target RNA is compared to a reference level of expression, e.g., from a confirmed cervical dysplasia. In some such embodiments, a similar level of expression of the at least one target RNA relative to the reference sample indicates cervical dysplasia.

In some embodiments, a level of expression of at least one target RNA that is at least about two-fold greater than a normal level of expression of the respective at least one target RNA indicates the presence of cervical dysplasia. In some embodiments, a level of expression of at least one target RNA that is at least about two-fold greater than the level of the respective at least one target RNA in a control sample comprised of normal cells indicates the presence of a cervical dysplasia. In various embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than the level of expression of the respective at least one target RNA in a control sample comprised of normal cells indicates the presence of cervical dysplasia. In various embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than a normal level of expression of the at least one target RNA indicates the presence of cervical dysplasia.

In some embodiments, an increase in expression of one or more target RNAs capable of specifically hybridizing to a nucleic acid comprising a sequence selected from SEQ ID NOs: 1 to 41 in Table 1 and SEQ ID NOs: 133 to 211 in Table 11 is indicative of the presence of cervical dysplasia or cervical cancer in a sample of human cervical cells. In some embodiments, an increase in expression of one or more target RNAs comprising at least 15 contiguous nucleotides of a sequence selected from SEQ ID NOs: 345 to 388 is indicative of the presence of cervical dysplasia or cervical cancer in a sample of human cervical cells. In some embodiments, an increase in expression of one or more target RNAs comprising a sequence that is complementary to at least 15 contiguous nucleotides of a sequence selected from SEQ ID NOs: 1 to 41 and 133 to 211 is indicative of the presence of cervical dysplasia or cervical cancer in a sample of human cervical cells.

In some embodiments, an increase in expression of one or more target RNAs capable of specifically hybridizing to a nucleic acid comprising a sequence selected from SEQ ID NOs: 1 to 41 in Table 1 and SEQ ID NOs: 133 to 211 in Table 11 is indicative of the presence of cervical dysplasia in a sample of human cervical cells that is likely to proceed to cervical cancer. In some embodiments, an increase in expression of one or more target RNAs comprising at least 15 contiguous nucleotides of a sequence selected from SEQ ID NOs: 345 to 388 is indicative of the presence of cervical dysplasia in a sample of human cervical cells that is likely to proceed to cervical cancer. In some embodiments, an increase in expression of one or more target RNAs comprising a sequence that is complementary to at least 15 contiguous nucleotides of a sequence selected from SEQ ID NOs: 1 to 41 and 133 to 211 is indicative of the presence of cervical dysplasia in a sample of human cervical cells that is likely to proceed to cervical cancer.

In some embodiments, a control level of expression of a target RNA is determined contemporaneously, such as in the same assay or batch of assays, as the level of expression of the target RNA in a sample. In some embodiments, a control level of expression of a target RNA is not determined contemporaneously as the level of expression of the target RNA in a sample. In some such embodiments, the control level of expression has been determined previously.

In some embodiments, the level of expression of a target RNA is not compared to a control level of expression, for example, when it is known that the target RNA is expressed at very low levels, or not at all, in normal cells. In such embodiments, detection of a high level of the target RNA in a sample is indicative of cervical dysplasia.

4.1.3. Exemplary Methods of Preparing RNAs

Target RNA can be prepared by any appropriate method. Total RNA can be isolated by any method, including, but not limited to, the protocols set forth in Wilkinson, M. (1988) *Nucl. Acids Res.* 16(22):10,933; and Wilkinson, M. (1988) *Nucl. Acids Res.* 16(22): 10934, or by using commercially-available kits or reagents, such as the TRIzol® reagent (Invitrogen™), Total RNA Extraction Kit (iNtRON Biotechnology), Total RNA Purification Kit (Norgen Biotek Corp.), RNAqueous™ (Ambion), MagMAX™ (Ambion), RecoverAll™ (Ambion), RNeasy (Qiagen), etc.

In some embodiments, small RNAs are isolated or enriched. In some embodiments "small RNA" refers to RNA molecules smaller than about 200 nucleotides (nt) in length. In some embodiments, "small RNA" refers to RNA molecules smaller than about 100 nt, smaller than about 90 nt, smaller than about 80 nt, smaller than about 70 nt, smaller than about 60 nt, smaller than about 50 nt, or smaller than about 40 nt.

Enrichment of small RNAs can be accomplished by method. Such methods include, but are not limited to, methods involving organic extraction followed by adsorption of nucleic acid molecules on a glass fiber filter using specialized binding and wash solutions, and methods using spin column purification. Enrichment of small RNAs may be accomplished using commercially-available kits, such as mirVana™ Isolation Kit (Applied Biosystems), mirPremier™ microRNA Isolation Kit (Sigma-Aldrich), PureLink™ miRNA Isolation Kit (Invitrogen), miRCURY™ RNA isolation kit (Exiqon), microRNA Purification Kit (Norgen Biotek Corp.), miRNeasy kit (Qiagen), etc. In some embodiments, purification can be accomplished by the TRIzol® (Invitrogen) method, which employs a phenol/isothiocyanate solution to which chloroform is added to separate the RNA-containing aqueous phase. Small RNAs are subsequently recovered from the aqueous by precipitation with isopropyl alcohol. In some embodiments, small RNAs can be purified using chromatographic methods, such as gel electrophoresis using the flashPAGE™ Fractionator available from Applied Biosystems.

In some embodiments, small RNA is isolated from other RNA molecules to enrich for target RNAs, such that the small RNA fraction (e.g., containing RNA molecules that are 200 nucleotides or less in length, such as less than 100 nucleotides in length, such as less than 50 nucleotides in length, such as from about 10 to about 40 nucleotides in length) is substantially pure, meaning it is at least about 80%, 85%, 90%, 95% pure or more, but less than 100% pure, with respect to larger RNA molecules. Alternatively, enrichment of small RNA can be expressed in terms of fold-enrichment. In some embodiments, small RNA is enriched by about, at least about, or at most about 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000×, 1100×, 1200×, 1300×, 1400×, 1500×, 1600×, 1700×, 1800×, 1900×, 2000×, 3000×, 4000×, 5000×, 6000×, 7000×, 8000×, 9000×, 10,000× or more, or any range derivable therein, with respect to the concentration of larger RNAs in an RNA isolate or total RNA in a sample.

In yet other embodiments, expression is measured in a sample in which RNA has not first been purified from the cells.

In some embodiments, RNA is modified before target RNAs are detected. In some embodiments, the modified RNA is total RNA. In other embodiments, the modified RNA is small RNA that has been purified from total RNA or from cell lysates, such as RNA less than 200 nucleotides in length, such as less than 100 nucleotides in length, such as less than 50 nucleotides in length, such as from about 10 to about 40 nucleotides in length. RNA modifications that can be utilized in the methods described herein include, but are not limited to, the addition of a poly-dA or a poly-dT tail, which can be accomplished chemically or enzymatically, and/or the addition of a small molecule, such as biotin.

In some embodiments, one or more target RNAs are reverse transcribed. In some embodiments, where present, RNA is modified when it is reverse transcribed, such as when a poly-dA or a poly-dT tail is added to the cDNA during reverse transcription. In other embodiments, RNA is modified before it is reverse transcribed. In some embodiments, total RNA is reverse transcribed. In other embodiments, small RNAs are isolated or enriched before the RNA is reverse transcribed.

When a target RNA is reverse transcribed, a complement of the target RNA is formed. In some embodiments, the complement of the target RNA is detected rather than the target RNA itself (or a DNA copy thereof). Thus, when the methods discussed herein indicate that a target RNA is detected, or the level of a target RNA is determined, such detection or determination may be carried out on a complement of the target RNA instead of, or in addition to, the target RNA itself. In some embodiments, when the complement of the target RNA is detected rather than the target RNA, a probe is used that is complementary to the complement of the target RNA. In such embodiments, the probe comprises at least a portion that is identical in sequence to the target RNA, although it may contain thymidine in place of uridine, and/or comprise other modified nucleotides.

In some embodiments, the method of detecting one or more target RNAs comprises amplifying cDNA complementary to said target RNA. Such amplification can be accomplished by any method. Exemplary methods include, but are not limited to, real time PCR, endpoint PCR, and amplification using T7 polymerase from a T7 promoter annealed to a cDNA, such as provided by the SenseAmp Plus™ Kit available at Implen, Germany.

When a target RNA or a cDNA complementary to a target RNA is amplified, in some embodiments, a DNA amplicon of a target RNA is formed. A DNA amplicon may be single stranded or double-stranded. In some embodiments, when a DNA amplicon is single-stranded, the sequence of the DNA amplicon is related to the target RNA in either the sense or antisense orientation. In some embodiments, the DNA amplicon of the target RNA is detected rather than the target RNA itself. Thus, when the methods discussed herein indicate that a target RNA is detected, or the level of a target RNA is determined, such detection or determination may be carried out on a DNA amplicon of the target RNA instead of, or in addition to, the target RNA itself. In some embodiments, when the DNA amplicon of the target RNA is detected rather than the target RNA, a probe is used that is complementary to the complement of the target RNA. In some embodiments, when the DNA amplicon of the target RNA is detected rather than the target RNA, a probe is used that is complementary to the target RNA. Further, I some embodiments, multiple probes may be used, and some probes may be complementary to the target RNA and some probes may be complementary to the complement of the target RNA.

In some embodiments, the method of detecting one or more target RNAs comprises RT-PCR, as described below. In some embodiments, detecting one or more target RNAs comprises real-time monitoring of an RT-PCR reaction, which can be accomplished by any method. Such methods include, but are not limited to, the use of TaqMan®, Molecular beacon, or Scorpion probes (i.e., FRET probes) and the use of intercalating dyes, such as SYBR green, EvaGreen, thiazole orange, YO-PRO, TO-PRO, etc.

4.1.4. Exemplary Analytical Methods

As described above, methods are presented for detecting cervical dysplasia, including cervical dysplasia likely to progress to carcinoma, in a sample of human cervical cells. In some embodiments, the method comprises detecting a level of expression of at least one target RNA capable of specifically hybridizing to a nucleic acid comprising a sequence selected from SEQ ID NOs: 1 to 41 set forth in Table 1 and SEQ ID NOs: 133 to 211 set forth in Table 11 that is greater in the sample than a normal level of expression of the at least one target RNA in a control sample, such as a sample derived from normal cervical cells. In some embodiments, a method comprises detecting a level of one or more target RNAs comprising at least 15 contiguous nucleotides of a sequence selected from SEQ ID NOs: 345 to 388 that is greater in the sample than a normal level of expression of the at least one target RNA in a control sample. In some embodiments, a method comprises detecting a level of one or more target RNAs that comprise a sequence that is complementary to at least 15 contiguous nucleotides of a sequence selected from SEQ ID NOs: 1 to 41 and 133 to 211 that is greater in the sample than a normal level of expression of the at least one target RNA in a control sample. In some embodiments, a target RNA, in its mature form, comprises fewer than 30 nucleotides. In some embodiments, a target RNA is a microRNA.

In some embodiments, such as those described above, the method further comprises detecting a level of expression of at least one target RNA of the human miRNome that does not specifically hybridize to a nucleic acid comprising a sequence selected from SEQ ID NOs: 1 to 41 set forth in Table 1 and SEQ ID NOs: 133 to 211 set forth in Table 11 that is greater in the sample than a normal level of expression of the at least one target RNA in a control sample. As used herein, the term "human miRNome" refers to all microRNA genes in a human cell and the mature microRNAs produced therefrom.

Any analytical procedure capable of permitting specific and quantifiable (or semi-quantifiable) detection of the desired at least one target RNA may be used in the methods herein presented. Such analytical procedures include, but are not limited to, the microarray methods set forth in Example 1 and the RT-PCR methods set forth in Example 6, and methods known to those skilled in the art.

In some embodiments, detection of a target RNA comprises forming a complex comprising a polynucleotide that is complementary to a target RNA or to a complement thereof, and a nucleic acid selected from the target RNA, a DNA amplicon of the target RNA, and a complement of the target RNA. Thus, in some embodiments, the polynucleotide forms a complex with a target RNA. In some embodiments, the polynucleotide forms a complex with a complement of the target RNA, such as a cDNA that has been reverse transcribed from the target RNA. In some embodiments, the polynucleotide forms a complex with a DNA amplicon of the target RNA. When a double-stranded DNA amplicon is part of a complex, as used herein, the complex may comprise one or both strands of the DNA amplicon. Thus, in some embodiments, a complex comprises only one strand of the DNA amplicon. In some embodiments, a complex is a triplex and comprises the polynucleotide and both strands of the DNA amplicon. In some embodiments, the complex is formed by hybridization between the polynucleotide and the target RNA, complement of the target RNA, or DNA amplicon of the target RNA. The polynucleotide, in some embodiments, is a primer or probe.

In some embodiments, a method comprises detecting the complex. In some embodiments, the complex does not have to be associated at the time of detection. That is, in some embodiments, a complex is formed, the complex is then dissociated or destroyed in some manner, and components from the complex are detected. An example of such a system is a TaqMan® assay. In some embodiments, when the polynucleotide is a primer, detection of the complex may comprise amplification of the target RNA, a complement of the target RNA, or a DNA amplicon of a target RNA.

In some embodiments the analytical method used for detecting at least one target RNA in the methods set forth herein includes real-time quantitative RT-PCR. See Chen, C. et al. (2005) *Nucl. Acids Res.* 33:e179 and PCT Publication No. WO 2007/117256, which are incorporated herein by reference in its entirety. In some embodiments, the analytical method used for detecting at least one target RNA includes the method described in U.S. Publication No. US2009/0123912 A1, which is incorporated herein by reference in its entirety. In an exemplary method described in that publication, an extension primer comprising a first portion and second portion, wherein the first portion selectively hybridizes to the 3' end of a particular microRNA and the second portion comprises a sequence for universal primer, is used to reverse transcribe the microRNA to make a cDNA. A reverse primer that selectively hybridizes to the 5' end of the microRNA and a universal primer are then used to amplify the cDNA in a quantitative PCR reaction.

In some embodiments, the analytical method used for detecting at least one target RNA includes the use of a TaqMan® probe. In some embodiments, the analytical method used for detecting at least one target RNA includes a TaqMan® assay, such as the TaqMan® MicroRNA Assays sold by Applied Biosystems, Inc. In an exemplary TaqMan® assay, total RNA is isolated from the sample. In some embodiments, the assay can be used to analyze about 10 ng of total RNA input sample, such as about 9 ng of input sample, such as about 8 ng of input sample, such as about 7 ng of input sample, such as about 6 ng of input sample, such as about 5 ng of input sample, such as about 4 ng of input sample, such as about 3 ng of input sample, such as about 2 ng of input sample, and even as little as about 1 ng of input sample containing microRNAs.

The TaqMan® assay utilizes a stem-loop primer that is specifically complementary to the 3'-end of a target RNA. In an exemplary TaqMan® assay, hybridizing the stem-loop primer to the target RNA is followed by reverse transcription of the target RNA template, resulting in extension of the 3' end of the primer. The result of the reverse transcription is a chimeric (DNA) amplicon with the step-loop primer sequence at the 5' end of the amplicon and the cDNA of the target RNA at the 3' end. Quantitation of the target RNA is achieved by real time RT-PCR using a universal reverse primer having a sequence that is complementary to a sequence at the 5' end of all stem-loop target RNA primers, a target RNA-specific forward primer, and a target RNA sequence-specific TaqMan® probe.

The assay uses fluorescence resonance energy transfer ("FRET") to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that FRET is abolished and a fluorescence signal is generated. Fluorescence increases with each RT-PCR cycle proportionally to the amount of probe that is cleaved.

Additional exemplary methods for RNA detection and/or quantification are described, e.g., in U.S. Publication No. US 2007/0077570 (Lao et al.), PCT Publication No. WO 2007/025281 (Tan et al.), U.S. Publication No. US2007/0054287 (Bloch), PCT Publication No. WO2006/0130761 (Bloch), and PCT Publication No. WO 2007/011903 (Lao et al.), which are incorporated by reference herein in their entireties for any purpose.

In some embodiments, quantitation of the results of real-time RT-PCR assays is done by constructing a standard curve from a nucleic acid of known concentration and then extrapolating quantitative information for target RNAs of unknown concentration. In some embodiments, the nucleic acid used for generating a standard curve is an RNA (e.g., microRNA) of known concentration. In some embodiments, the nucleic acid used for generating a standard curve is a purified double-stranded plasmid DNA or a single-stranded DNA generated in vitro.

In some embodiments, where the amplification efficiencies of the target nucleic acids and the endogenous reference are approximately equal, quantitation is accomplished by the comparative Ct (cycle threshold, e.g., the number of PCR cycles required for the fluorescence signal to rise above background) method. Ct values are inversely proportional to the amount of nucleic acid target in a sample. In some embodiments, Ct values of the target RNA of interest can be compared with a control or calibrator, such as RNA (e.g., microRNA) from normal tissue. In some embodiments, the Ct values of the calibrator and the target RNA samples of interest are normalized to an appropriate endogenous housekeeping gene.

In addition to the TaqMan® assays, other real-time RT-PCR chemistries useful for detecting and quantitating PCR products in the methods presented herein include, but are not limited to, Molecular Beacons, Scorpion probes and intercalating dyes, such as SYBR Green, EvaGreen, thiazole orange, YO-PRO, TO-PRO, etc., which are discussed below.

In some embodiments, real-time RT-PCR detection is performed specifically to detect and quantify the expression of a single target RNA. The target RNA, in some embodiments, is selected from a target RNA capable of specifically hybridizing to a nucleic acid comprising a sequence selected from SEQ ID NOs: 1 to 41 set forth in Table 1 and SEQ ID NOs: 133 to 211 set forth in Table 11. In some embodiments, the target RNA specifically hybridizes to a nucleic acid comprising a sequence selected from SEQ ID NOs: 1, 2, 3, 4, 5, 6, 7, or 8. In some embodiments, the target RNA specifically hybridizes to a nucleic acid comprising a sequence selected from SEQ ID NOs: 1, 2, 3, 4, 5, 6, 7, 8, 9, 10, 11 or 12. In some embodiments, the target RNA specifically hybridizes to a nucleic acid comprising a sequence selected from SEQ ID NOs: 142, 151, 153, 193, 194, 205, 172, 208, 210, and 211. In some embodiments, the target RNA specifically hybridizes to a nucleic acid comprising a sequence selected from SEQ ID NOs: 1, 5, 7, and 32. In some embodiments, the target RNA comprises at least 15 contiguous nucleotides of a sequence selected from SEQ ID NOs: 345 to 388. In some embodiments, the target RNA comprises a sequence that is complementary to at least 15 contiguous nucleotides of a sequence selected from SEQ ID NOs: 1 to 41 and 133 to 211. In some embodiments, a target RNA, in its mature form, comprises fewer than 30 nucleotides. In some embodiments, a target RNA is a microRNA.

As described above, in some embodiments, in addition to detecting expression of one or more target RNAs capable of specifically hybridizing to a nucleic acid comprising a sequence selected from SEQ ID NOs: 1 to 41 and SEQ ID NOs: 133 to 211, and/or detecting expression of at least one target RNA comprising at least 15 contiguous nucleotides of a sequence selected from SEQ ID NOs: 345 to 388 and/or detecting expression of at least one target RNA comprising a sequence that is complementary to at least 15 contiguous nucleotides of a sequence selected from SEQ ID NOs: 1 to 41 and 133 to 211, the methods comprise detection of expression of one or more microRNAs selected from miR-21, miR-31, miR-182, miR-183, miR-155, miR-9, miR-199a*, miR-199a, miR-199b, miR-145, miR-133a, miR-133b, miR-214, miR-127, miR-205, miR-210, miR-146a, miR-301, miR-142-5p, miR-194, miR-215, miR-32, miR-374b, miR-933, miR-769-3p, miR-671, miR-934, miR-935, miR-937, miR-938, miR-939, miR-940, miR-941, miR-942, miR-943, miR-944, miR-708, miR-874-5p, and miR-874-3p.

In various other embodiments, real-time RT-PCR detection is utilized to detect, in a single multiplex reaction, at least 2, at least 3, at least 4, at least 5, at least 6, at least 7, or at least 8 target RNAs. At least one target RNA, in some embodiments, is capable of specifically hybridizing to a nucleic acid comprising a sequence selected from SEQ ID NOs: 1 to 41 and 133 to 211. In some embodiments, at least one target RNA comprises at least 15 contiguous nucleotides of a sequence selected from SEQ ID NOs: 345 to 388. In some embodiments, at least one target RNA comprises a sequence that is complementary to at least 15 contiguous nucleotides of a sequence selected from SEQ ID NOs: 1 to 41 and 133 to 211. In some embodiments, a target RNA, in its mature form, comprises fewer than 30 nucleotides. In some embodiments, a target RNA is a microRNA.

In some embodiments, the method comprises detecting expression in a multiplex RT-PCR reaction of at least 2, at least 3, at least 4, at least 5, at least 6, at least 7, or at least 8 target RNAs, wherein each target RNA is capable of specifically hybridizing to a nucleic acid comprising a sequence selected from SEQ ID NOs: 1, 2, 3, 4, 5, 6, 7, and 8. In some embodiments, the method comprises detecting greater than normal expression, using a single multiplex RT-PCR reaction, of at least 2, at least 3, at least 4, at least 5, at least 6, at least 7, at least 8, at least 9, at least 10, or at least 12 target RNAs, wherein each target RNA is capable of specifically hybridizing to a nucleic acid comprising a sequence selected from SEQ ID NOs: 1, 2, 3, 4, 5, 6, 7, 8, 9, 10, 11 and 12. In some embodiments, the method comprises detecting greater than normal expression, using a single multiplex RT-PCR reaction, of at least 2, at least 3, at least 4, at least 5, at least 6, at least 7, at least 8, at least 9, at least 10, or at least 12 target RNAs, wherein each target RNA is capable of specifically hybridizing to a nucleic acid comprising a sequence selected from SEQ ID NOs: 142, 151, 153, 193, 194, 205, 172, 208, 210, and 211. In some embodiments, the method comprises detecting expression in a multiplex RT-PCR reaction of at least 2, at least 3, at least 4, at least 5, at least 6, at least 7, at least 8, or at least 9 target RNAs, wherein each target RNA is capable of specifically hybridizing to a nucleic acid comprising a sequence selected from SEQ ID NOs: 1, 4, 5, 7, 12, 17, 25, 26, 32.

In some multiplex embodiments, a plurality of probes, such as TaqMan® probes, each specific for a different RNA target, is used. In some embodiments, each target RNA-specific probe is spectrally distinguishable from the other probes used in the same multiplex reaction.

In some embodiments, quantitation of real-time RT PCR products is accomplished using a dye that binds to double-stranded DNA products, such as SYBR Green, EvaGreen, thiazole orange, YO-PRO, TO-PRO, etc. In some embodiments, the assay is the QuantiTect SYBR Green PCR assay from Qiagen. In this assay, total RNA is first isolated from a sample. Total RNA is subsequently poly-adenylated at the 3'-end and reverse transcribed using a universal primer with poly-dT at the 5'-end. In some embodiments, a single reverse transcription reaction is sufficient to assay multiple target RNAs. Real-time RT-PCR is then accomplished using target RNA-specific primers and an miScript Universal Primer, which comprises a poly-dT sequence at the 5'-end. SYBR Green dye binds non-specifically to double-stranded DNA and upon excitation, emits light. In some embodiments, buffer conditions that promote highly-specific annealing of primers to the PCR template (e.g., available in the Quanti- Tect SYBR Green PCR Kit from Qiagen) can be used to avoid the formation of non-specific DNA duplexes and primer dimers that will bind SYBR Green and negatively affect quantitation. Thus, as PCR product accumulates, the signal from SYBR Green increases, allowing quantitation of specific products.

Real-time RT-PCR is performed using any RT-PCR instrumentation available in the art. Typically, instrumentation used in real-time RT-PCR data collection and analysis comprises a thermal cycler, optics for fluorescence excitation and emission collection, and optionally a computer and data acquisition and analysis software.

In some embodiments, the analytical method used in the methods described herein is a DASL® (cDNA-mediated Annealing, Selection, Extension, and Ligation) Assay, such as the MicroRNA Expression Profiling Assay available from Illumina, Inc. (See http://www.illumina.com/downloads/MicroRNAAssayWorkflow.pdf). In some embodiments, total RNA is isolated from a sample to be analyzed by any method. Additionally, in some embodiments, small RNAs are isolated from a sample to be analyzed by any method. Total RNA or isolated small RNAs may then be polyadenylated (>18 A residues are added to the 3'-ends of the RNAs in the reaction mixture). The RNA is reverse transcribed using a biotin-labeled DNA primer that comprises from the 5' to the 3' end, a sequence that includes a PCR primer site and a poly-dT region that binds to the poly-dA tail of the sample RNA. The resulting biotinylated cDNA transcripts are then hybridized to a solid support via a biotin-streptavidin interaction and contacted with one or more target RNA-specific polynucleotides. The target RNA-specific polynucleotides comprise, from the 5'-end to the 3'-end, a region comprising a PCR primer site, region comprising an address sequence, and a target RNA-specific sequence.

In some DASL® embodiments, the target RNA-specific sequence comprises at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides having a sequence identically present in one of SEQ ID NOs: 1 to 41 and 133 to 211. In some embodiments, the target RNA-specific sequence comprises a probe sequence that is complementary to at least a portion of a microRNA of the human miRNome, such as miR-21, miR-31, miR-182, miR-183, miR-155, miR-9, miR-199a*, miR-199a, miR-199b, miR-145, miR-133a, miR-133b, miR-205, miR-214, miR-127, miR-210, miR-146a, miR-301, miR-142-5p, miR-194, miR-215, miR-32, miR-374b, miR-933, miR-769-3p, miR-671, miR-934, miR-935, miR-937, miR-938, miR-939, miR-940, miR-941, miR-942, miR-943, miR-944, miR-708, miR-874-5p, and miR-874-3p.

After hybridization, the target RNA-specific polynucleotide is extended, and the extended products are then eluted from the immobilized cDNA array. A second PCR reaction using a fluorescently-labeled universal primer generates a fluorescently-labeled DNA comprising the target RNA-specific sequence. The labeled PCR products are then hybridized to a microbead array for detection and quantitation.

In some embodiments, the analytical method used for detecting and quantifying the expression of the at least one target RNA in the methods described herein is a bead-based flow cytometric assay. See Lu J. et al. (2005) Nature 435:834-838, which is incorporated herein by reference in its entirety. An example of a bead-based flow cytometric assay is the xMAP® technology of Luminex, Inc. (See http://www.luminexcorp.com/technology/index.html). In some embodiments, total RNA is isolated from a sample and is then labeled with biotin. The labeled RNA is then hybridized to target RNA-specific capture probes (e.g., FlexmiR™ products sold by Luminex, Inc. at http://www.luminexcorp.com/products/assays/index.html) that are covalently bound to microbeads, each of which is labeled with 2 dyes having different fluorescence intensities. A streptavidin-bound reporter molecule (e.g., streptavidin-phycoerythrin, also known as "SAPE") is attached to the captured target RNA and the unique signal of each bead is read using flow cytometry. In some embodiments, the RNA sample (total RNA or enriched small RNAs) is first polyadenylated, and is subsequently labeled with a biotinylated 3DNA™ dendrimer (i.e., a multiple-arm DNA with numerous biotin molecules bound thereto), such as those sold by Marligen Biosciences as the Vantage™ microRNA Labeling Kit, using a bridging polynucleotide that is complementary to the 3'-end of the poly-dA tail of the sample RNA and to the 5'-end of the polynucleotide attached to the biotinylated dendrimer. The streptavidin-bound reporter molecule is then attached to the biotinylated dendrimer before analysis by flow cytometry. See http://www.marligen.com/vantage-microrna-labeling-kit.html. In some embodiments, biotin-labeled RNA is first exposed to SAPE, and the RNA/SAPE complex is subsequently exposed to an anti-phycoerythrin antibody attached to a DNA dendrimer, which can be bound to as many as 900 biotin molecules. This allows multiple SAPE molecules to bind to the biotinylated dendrimer through the biotin-streptavidin interaction, thus increasing the signal from the assay.

In some embodiments, the analytical method used for detecting and quantifying the expression of the at least one target RNA in the methods described herein is by gel electrophoresis and detection with labeled probes (e.g., probes labeled with a radioactive or chemiluminescent label), such as by Northern blotting. In some embodiments, total RNA is isolated from the sample, and then is size-separated by SDS polyacrylamide gel electrophoresis. The separated RNA is then blotted onto a membrane and hybridized to radiolabeled complementary probes. In some embodiments, exemplary probes contain one or more affinity-enhancing nucleotide analogs as discussed below, such as locked nucleic acid ("LNA") analogs, which contain a bicyclic sugar moiety instead of deoxyribose or ribose sugars. See, e.g., Varallyay, E. et al. (2008) Nature Protocols 3(2):190-196, which is incorporated herein by reference in its entirety. In some embodiments, the total RNA sample can be further purified to enrich for small RNAs. In some embodiments, target RNAs can be amplified by, e.g., rolling circle amplification using a long probe that is complementary to both ends of a target RNA ("padlocked probes"), ligation to circularize the probe followed by rolling circle replication using the target RNA hybridized to the circularized probe as a primer. See, e.g., Jonstrup, S. P. et al. (2006) RNA 12:1-6, which is incorporated herein by reference in its entirety. The amplified product can then be detected and quantified using, e.g., gel electrophoresis and Northern blotting.

In alternative embodiments, labeled probes are hybridized to isolated total RNA in solution, after which the RNA is subjected to rapid ribonuclease digestion of single-stranded RNA, e.g., unhybridized portions of the probes or unhybridized target RNAs. In these embodiments, the ribonuclease treated sample is then analyzed by SDS-PAGE and detection of the radiolabeled probes by, e.g., Northern blotting. See mirVana™ miRNA Detection Kit sold by Applied Biosystems, Inc. product literature at http://www.ambion.com/catalog/CatNum.php?1552.

In some embodiments, the analytical method used for detecting and quantifying the at least one target RNA in the methods described herein is by hybridization to a microarray. See, e.g., Liu, C. G. et al. (2004) Proc. Nat'l Acad. Sci. USA 101:9740-9744; Lim, L. P. et al. (2005) Nature 433: 769-773, each of which is incorporated herein by reference in its entirety, and Example 1.

In some embodiments, detection and quantification of a target RNA using a microarray is accomplished by surface plasmon resonance. See, e.g., Nanotech News (2006), available at http://nano.cancer.gov/news_center/nanotech_news_2006-10-30b.asp. In these embodiments, total RNA is isolated from a sample being tested. Optionally, the RNA sample is further purified to enrich the population of small RNAs. After purification, the RNA sample is bound to an addressable microarray containing probes at defined locations on the microarray. Nonlimiting exemplary probes include probes comprising sequences set forth in SEQ ID NOs: 1 to 41 and 133 to 211. Exemplary probes also include, but are not limited to, probes comprising a region that is complementary to at least 15 contiguous nucleotides of a sequence selected from SEQ ID NOs: 345 to 388. Exemplary probes also include, but are not limited to, probes comprising at least 15 contiguous nucleotides of a sequence selected from SEQ ID NOs: 1 to 41 and 133 to 211. In some embodiments, the probes contain one or more affinity-enhancing nucleotide analogs as discussed below, such as locked nucleic acid ("LNA") nucleotide analogs. After hybridization to the microarray, the RNA that is hybridized to the array is first polyadenylated, and the array is then exposed to gold particles having poly-dT bound to them. The amount of bound target RNA is quantitated using surface plasmon resonance.

In some embodiments, microarrays are utilized in a RNA-primed, Array-based Klenow Enzyme ("RAKE") assay. See Nelson, P. T. et al. (2004) Nature Methods 1(2):1-7; Nelson, P. T. et al. (2006) RNA 12(2):1-5, each of which is incorporated herein by reference in its entirety. In some embodiments, total RNA is isolated from a sample. In some embodiments, small RNAs are isolated from a sample. The RNA sample is then hybridized to DNA probes immobilized at the 5'-end on an addressable array. The DNA probes comprise, in some embodiments, from the 5'-end to the 3'-end, a first region comprising a "spacer" sequence which is the same for all probes, a second region comprising three thymidine-containing nucleosides, and a third region comprising a sequence that is complementary to a target RNA of interest.

Exemplary target RNAs of interest include, but are not limited to, target RNAs capable of specifically hybridizing to a nucleic acid comprising a sequence selected from SEQ ID NOs: 1 to 41 and 133 to 211, and target RNAs comprising at least 15 contiguous nucleotides of a sequence selected from SEQ ID NOs: 345 to 388, and target RNAs comprising a region that is complementary to at least 15 contiguous nucleotides of a sequence selected from SEQ ID NOs: 1 to 41 and 133 to 211. Target RNAs also include target RNAs in the miRNome that do not specifically hybridize to a nucleic acid comprising a sequence selected from SEQ ID NOs: 1 to 41 and 133 to 211. In some embodiments, a target RNA, in its mature form, comprises fewer than 30 nucleotides. In some embodiments, a target RNA is a microRNA.

After the sample is hybridized to the array, it is exposed to exonuclease I to digest any unhybridized probes. The Klenow fragment of DNA polymerase I is then applied along with biotinylated dATP, allowing the hybridized target RNAs to act as primers for the enzyme with the DNA probe as template. The slide is then washed and a streptavidin-conjugated fluorophore is applied to detect and quantitate the spots on the array containing hybridized and Klenow-extended target RNAs from the sample.

In some embodiments, the RNA sample is reverse transcribed. In some embodiments, the RNA sample is reverse transcribed using a biotin/poly-dA random octamer primer. When than primer is used, the RNA template is digested and the biotin-containing cDNA is hybridized to an addressable microarray with bound probes that permit specific detection of target RNAs. In typical embodiments, the microarray includes at least one probe comprising at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides identically present in, or complementary to a region of, a sequence selected from SEQ ID NOs: 1 to 41, 133 to 211, and 345 to 388. After hybridization of the cDNA to the microarray, the microarray is exposed to a streptavidin-bound detectable marker, such as a fluorescent dye, and the bound cDNA is detected. See Liu C. G. et al. (2008) *Methods* 44:22-30, which is incorporated herein by reference in its entirety.

In some embodiments, target RNAs are detected and quantified in an ELISA-like assay using probes bound in the wells of microtiter plates. See Mora J. R. and Getts R. C. (2006) BioTechniques 41:420-424 and supplementary material in BioTechniques 41(4):1-5; U.S. Patent Publication No. 2006/0094025 to Getts et al., each of which is incorporated by reference herein in its entirety. In these embodiments, a sample of RNA that is enriched in small RNAs is either polyadenylated, or is reverse transcribed and the cDNA is polyadenylated. The RNA or cDNA is hybridized to probes immobilized in the wells of a microtiter plates, wherein each of the probes comprises a sequence that is identically present in, or complementary to a region of, one of SEQ ID NOs: 1 to 41, 133 to 211, or 345 to 388, or a sequence such as one or more sequences of target RNAs (or the reverse complement thereof) of the human miRNome, depending on whether RNA or cDNA is hybridized to the array. In some embodiments, the hybridized RNAs are labeled using a capture sequence, such as a DNA dendrimer (such as those available from Genisphere, Inc., http://www.genisphere.comiabout3dna.html) that is labeled with a plurality of biotin molecules or with a plurality of horse-radish peroxidase molecules, and a bridging polynucleotide that contains a poly-dT sequence at the 5'-end that binds to the poly-dA tail of the captured nucleic acid, and a sequence at the 3'-end that is complementary to a region of the capture sequence. If the capture sequence is biotinylated, the microarray is then exposed to streptavidin-bound horseradish peroxidase. Hybridization of target RNAs is detected by the addition of a horseradish peroxidase substrate such as tetramethylbenzidine (TMB) and measurement of the absorbance of the solution at 450 nM.

In still other embodiments, an addressable microarray is used to detect a target RNA using quantum dots. See Liang, R. Q. et al. (2005) *Nucl. Acids Res.* 33(2):e17, available at http://www.pubmedcentral.nih.gov/articlerender.fcgi?artid=548377, which is incorporated herein by reference in its entirety. In some embodiments, total RNA is isolated from a sample. In some embodiments, small RNAs are isolated from the sample. The 3'-ends of the target RNAs are biotinylated using biotin-X-hydrazide. The biotinylated target RNAs are captured on a microarray comprising immobilized probes comprising sequences that are identically present in, or complementary to a region of, one or more of SEQ ID NOs: 1 to 41, 133 to 211, and 345 to 388 and/or probes comprising sequences other than those that are complementary to one or more microRNAs of the human miRNome. The hybridized target RNAs are then labeled with quantum dots via a biotin-streptavidin binding. A confocal laser causes the quantum dots to fluoresce and the signal can be quantified. In alternative embodiments, small RNAs can be detected using a colorimetric assay. In these embodiments, small RNAs are labeled with streptavidin-conjugated gold followed by silver enhancement. The gold nanoparticules bound to the hybridized target RNAs catalyze the reduction of silver ions to metallic silver, which can then be detected colorimetrically with a CCD camera In some embodiments, detection and quantification of one or more target RNAs is accomplished using microfluidic devices and single-molecule detection. In some embodiments, target RNAs in a sample of isolated total RNA are hybridized to two probes, one which is complementary to nucleic acids at the 5'-end of the target RNA and the second which is complementary to the 3'-end of the target RNA. Each probe comprises, in some embodiments, one or more affinity-enhancing nucleotide analogs, such as LNA nucleotide analogs and each is labeled with a different fluorescent dye having different fluorescence emission spectra. The sample is then flowed through a microfluidic capillary in which multiple lasers excite the fluorescent probes, such that a unique coincident burst of photons identifies a particular target RNA, and the number of particular unique coincident bursts of photons can be counted to quantify the amount of the target RNA in the sample. See U.S. Patent Publication No. 2006/0292616 to Neely et al., which is hereby incorporated by reference in its entirety. In some alternative embodiments, a target RNA-specific probe can be labeled with 3 or more distinct labels selected from, e.g., fluorophores, electron spin labels, etc., and then hybridized to an RNA sample, such as total RNA, or a sample that is enriched in small RNAs. Nonlimiting exemplary target RNA-specific probes include probes comprising sequences selected from of SEQ ID NOs: 1 to 41 and 133 to 211. Nonlimiting exemplary target RNA-specific probes include probes comprising sequences that are complementary to sequences selected from of SEQ ID NOs: 1 to 41 and 133 to 211. Nonlimiting exemplary target RNA-specific probes also include probes comprising at least 15 contiguous nucleotides of, or the complement of at least 15 contiguous nucleotides of, a sequence selected from SEQ ID NOs: 1 to 41, 133 to 211, and 345 to 388.

Optionally, the sample RNA is modified before hybridization. The target RNA/probe duplex is then passed through channels in a microfluidic device and that comprise detectors that record the unique signal of the 3 labels. In this way, individual molecules are detected by their unique signal and counted. See U.S. Pat. Nos. 7,402,422 and 7,351,538 to Fuchs et al., U.S. Genomics, Inc., each of which is incorporated herein by reference in its entirety.

In some embodiments, the detection and quantification of one or more target RNAs is accomplished by a solution-based assay, such as a modified Invader assay. See Allawi H. T. et al. (2004) RNA 10:1153-1161, which is incorporated herein by reference in its entirety. In some embodiments, the modified invader assay can be performed on unfractionated detergent lysates of cervical cells. In other embodiments, the modified invader assay can be performed on total RNA isolated from cells or on a sample enriched in small RNAs. The target RNAs in a sample are annealed to two probes which form hairpin structures. A first probe has a hairpin structure at the 5' end and a region at the 3'-end that has a sequence that is complementary to the sequence of a region at the 5'-end of a target RNA. The 3'-end of the first probe is the "invasive polynucleotide". A second probe has, from the 5' end to the 3'-end a first "flap" region that is not complementary to the target RNA, a second region that has a sequence that is complementary to the 3'-end of the target RNA, and a third region that forms a hairpin structure. When the two probes are bound to a target RNA target, they create an overlapping configuration of the probes on the target RNA template, which is recognized by the Cleavase enzyme, which releases the flap of the second probe into solution. The flap region then binds to a complementary region at the 3'-end of a secondary reaction template ("SRT"). A FRET polynucleotide (having a fluorescent dye bound to the 5'-end and a quencher that quenches the dye bound closer to the 3' end) binds to a complementary region at the 5'-end of the SRT, with the result that an overlapping configuration of the 3'-end of the flap and the 5'-end of the FRET polynucleotide is created. Cleavase recognizes the overlapping configuration and cleaves the 5'-end of the FRET polynucleotide, generates a fluorescent signal when the dye is released into solution.

4.1.5. Exemplary Polynucleotides

In some embodiments, polynucleotides are provided. In some embodiments, synthetic polynucleotides are provided. Synthetic polynucleotides, as used herein, refer to polynucleotides that have been synthesized in vitro either chemically or enzymatically. Chemical synthesis of polynucleotides includes, but is not limited to, synthesis using polynucleotide synthesizers, such as OligoPilot (GE Healthcare), ABI 3900 DNA Synthesizer (Applied Biosystems), and the like. Enzymatic synthesis includes, but is not limited, to producing polynucleotides by enzymatic amplification, e.g., PCR.

In some embodiments, a polynucleotide is provided that comprises at least 8, at least 9, at least 10, at least 11, at least 12, at least 13, at least 14, or at least 15 contiguous nucleotides of a sequence selected from SEQ ID NOs: 1 to 41, 133 to 211, and 345 to 388, and sequences complementary to SEQ ID NOs: 1 to 41, 133 to 211, and 345 to 388. In some embodiments, the polynucleotide further comprises a region having a sequence that is not found in, or complementary to, any of SEQ ID NOs: 1 to 41, 133 to 211, and 345 to 388. In some embodiments, a polynucleotide is provided that comprises at least 8, at least 9, at least 10, at least 11, at least 12, at least 13, at least 14, or at least 15 contiguous nucleotides of a sequence selected from SEQ ID NOs: 1 to 7, 9 to 37, 133 to 201, and 345 to 388, and sequences complementary to SEQ ID NOs: 1 to 7, 9 to 37, 133 to 201, and 345 to 388. In some embodiments, the polynucleotide further comprises a region having a sequence that is not found in, or complementary to, any of SEQ ID NOs: 1 to 7, 9 to 37, 133 to 201, and 345 to 388.

In various embodiments, a polynucleotide comprises fewer than 500, fewer than 300, fewer than 200, fewer than 150, fewer than 100, fewer than 75, fewer than 50, fewer than 40, or fewer than 30 nucleotides. In various embodiments, a polynucleotide is between 8 and 200, between 8 and 150, between 8 and 100, between 8 and 75, between 8 and 50, between 8 and 40, or between 8 and 30 nucleotides long.

In some embodiments, the polynucleotide is a primer. In some embodiments, the primer is labeled with a detectable moiety. In some embodiments, a primer is not labeled. A primer, as used herein, is a polynucleotide that is capable of specifically hybridizing to a target RNA or to a cDNA reverse transcribed from the target RNA or to an amplicon that has been amplified from a target RNA or a cDNA (collectively referred to as "template"), and, in the presence of the template, a polymerase and suitable buffers and reagents, can be extended to form a primer extension product.

In some embodiments, the polynucleotide is a probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not extendable, e.g., by a polymerase. In other embodiments, a probe is extendable.

In some embodiments, the polynucleotide is a FRET probe that in some embodiments is labeled at the 5'-end with a fluorescent dye (donor) and at the 3'-end with a quencher (acceptor), a chemical group that absorbs (i.e., suppresses) fluorescence emission from the dye when the groups are in close proximity (i.e., attached to the same probe). In other embodiments, the donor and acceptor are not at the ends of the FRET probe. Thus, in some embodiments, the emission spectrum of the donor moiety should overlap considerably with the absorption spectrum of the acceptor moiety.

4.1.5.1. Exemplary Polynucleotide Modifications

In some embodiments, the methods of detecting at least one target RNA described herein employ one or more polynucleotides that have been modified, such as polynucleotides comprising one or more affinity-enhancing nucleotide analogs. Modified polynucleotides useful in the methods described herein include primers for reverse transcription, PCR amplification primers, and probes. In some embodiments, the incorporation of affinity-enhancing nucleotides increases the binding affinity and specificity of a polynucleotide for its target nucleic acid as compared to polynucleotides that contain only deoxyribonucleotides, and allows for the use of shorter polynucleotides or for shorter regions of complementarity between the polynucleotide and the target nucleic acid.

In some embodiments, affinity-enhancing nucleotide analogs include nucleotides comprising one or more base modifications, sugar modifications and/or backbone modifications.

In some embodiments, modified bases for use in affinity-enhancing nucleotide analogs include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing nucleotide analogs include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing nucleotide analogs include backbone modifications such as the use of peptide nucleic acids (PNA; e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, a polynucleotide includes at least one affinity-enhancing nucleotide analog that has a modified base, at least nucleotide (which may be the same nucleotide) that has a modified sugar, and/or at least one internucleotide linkage that is non-naturally occurring.

In some embodiments, an affinity-enhancing nucleotide analog contains a locked nucleic acid ("LNA") sugar, which is a bicyclic sugar. In some embodiments, a polynucleotide for use in the methods described herein comprises one or more nucleotides having an LNA sugar. In some embodiments, a polynucleotide contains one or more regions consisting of nucleotides with LNA sugars. In other embodiments, a polynucleotide contains nucleotides with LNA sugars interspersed with deoxyribonucleotides. See, e.g., Frieden, M. et al. (2008) Curr. Pharm. Des. 14(11):1138-1142.

4.1.5.2. Exemplary Primers

In some embodiments, a primer is provided. In some embodiments, a primer is identical or complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of a target RNA. In some embodiments, a primer may also comprise portions or regions that are not identical or complementary to the target RNA. In some embodiments, a region of a primer that is identical or complementary to a target RNA is contiguous, such that any region of a primer that is not identical or complementary to the target RNA does not disrupt the identical or complementary region.

In some embodiments, a primer comprises a portion that is identically present in a target RNA. In some such embodiments, a primer that comprises a region that is identically present in the target RNA is capable of selectively hybridizing to a cDNA that has been reverse transcribed from the RNA, or to an amplicon that has been produced by amplification of the target RNA or cDNA. In some embodiments, the primer is complementary to a sufficient portion of the cDNA or amplicon such that it selectively hybridizes to the cDNA or amplicon under the conditions of the particular assay being used.

As used herein, "selectively hybridize" means that a polynucleotide, such as a primer or probe, will hybridize to a particular nucleic acid in a sample with at least 5-fold greater affinity than it will hybridize to another nucleic acid present in the same sample that has a different nucleotide sequence in the hybridizing region. Exemplary hybridization conditions are discussed in Example 1. In some embodiments, a polynucleotide will hybridize to a particular nucleic acid in a sample with at least 10-fold greater affinity than it will hybridize to another nucleic acid present in the same sample that has a different nucleotide sequence in the hybridizing region.

Nonlimiting exemplary primers include primers comprising sequences that are identically present in, or complementary to a region of, sequences selected from SEQ ID NOs: 1 to 41, 133 to 211, and 345 to 388. Exemplary primers also include, but are not limited to, primers comprising regions that are identical or complementary to at least 15 contiguous nucleotides of sequences selected from SEQ ID NOs: 1 to 41, 133 to 211, and 345 to 388.

In some embodiments, a primer is used to reverse transcribe a target RNA, for example, as discussed herein. In some embodiments, a primer is used to amplify a target RNA or a cDNA reverse transcribed therefrom. Such amplification, in some embodiments, is quantitative PCR, for example, as discussed herein. In some embodiments, a primer comprises a detectable moiety.

4.1.5.3. Exemplary Probes

In various embodiments, methods of detecting the presence of a cervical dysplasia comprise hybridizing nucleic acids of a human cervical sample with a probe. In some embodiments, the probe comprises a portion that is complementary to a target RNA. In some embodiments, the probe comprises a portion that is identically present in the target RNA. In some such embodiments, a probe that is complementary to a target RNA is complementary to a sufficient portion of the target RNA such that it selectively hybridizes to the target RNA under the conditions of the particular assay being used. In some embodiments, a probe that is complementary to a target RNA is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the target RNA. In some embodiments, a probe that is complementary to a target RNA comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the target RNA. That is, a probe that is complementary to a target RNA may also comprise portions or regions that are not complementary to the target RNA. In some embodiments, a region of a probe that is complementary to a target RNA is contiguous, such that any region of a probe that is not complementary to the target RNA does not disrupt the complementary region.

In some embodiments, the probe comprises a portion that is identically present in the target RNA. In some such embodiments, a probe that comprises a region that is identically present in the target RNA is capable of selectively hybridizing to a cDNA that has been reverse transcribed from the RNA, or to an amplicon that has been produced by amplification of the target RNA or cDNA. In some embodiments, the probe is complementary to a sufficient portion of the cDNA or amplicon such that it selectively hybridizes to the cDNA or amplicon under the conditions of the particular assay being used. In some embodiments, a probe that is complementary to a cDNA or amplicon is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the cDNA or amplicon. In some embodiments, a probe that is complementary to a target RNA comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the cDNA or amplicon. That is, a probe that is complementary to a cDNA or amplicon may also comprise portions or regions that are not complementary to the cDNA or amplicon. In some embodiments, a region of a probe that is complementary to a cDNA or amplicon is contiguous, such that any region of a probe that is not complementary to the cDNA or amplicon does not disrupt the complementary region.

Nonlimiting exemplary probes include probes comprising sequences set forth in SEQ ID NOs: 1 to 41 and 133 to 211. Nonlimiting exemplary probes include probes comprising sequences that are identically present in, or complementary to a region of, sequences selected from SEQ ID NOs: 1 to 41, 133 to 211, and 345 to 388. Exemplary probes also include, but are not limited to, probes comprising regions that are identical or complementary to at least 15 contiguous nucleotides of sequences selected from SEQ ID NOs: 1 to 41, 133 to 211, and 345 to 388.

In some embodiments, the method of detectably quantifying one or more target RNAs comprises: (a) isolating total RNA; (b) reverse transcribing a target RNA to produce a cDNA that is complementary to the target RNA; (c) amplifying the cDNA from (b); and (d) detecting the amount of a target RNA using real time RT-PCR and a detection probe.

As described above, in some embodiments, the real time RT-PCR detection is performed using a FRET probe, which includes, but is not limited to, a TaqMan® probe, a Molecular beacon probe and a Scorpion probe. In some embodiments, the real time RT-PCR detection and quantification is performed with a TaqMan® probe, i.e., a linear probe that typically has a fluorescent dye covalently bound at one end of the DNA and a quencher molecule covalently bound at the other end of the DNA. The FRET probe comprises a sequence that is complementary to a region of the cDNA such that, when the FRET probe is hybridized to the cDNA, the dye fluorescence is quenched, and when the probe is digested during amplification of the cDNA, the dye is released from the probe and produces a fluorescence signal. In such embodiments, the amount of target RNA in the sample is proportional to the amount of fluorescence measured during cDNA amplification.

The TaqMan® probe typically comprises a region of contiguous nucleotides having a sequence that is complementary to a region of a target RNA or its complementary cDNA that is reverse transcribed from the target RNA template (i.e., the sequence of the probe region is complementary to or identically present in the target RNA to be detected) such that the probe is specifically hybridizable to the resulting PCR amplicon. In some embodiments, the probe comprises a region of at least 6 contiguous nucleotides having a sequence that is fully complementary to or identically present in a region of a cDNA that has been reverse transcribed from a target RNA template, such as comprising a region of at least 8 contiguous nucleotides, at least 10 contiguous nucleotides, at least 12 contiguous nucleotides, at least 14 contiguous nucleotides, or at least 16 contiguous nucleotides having a sequence that is complementary to or identically present in a region of a cDNA reverse transcribed from a target RNA to be detected.

In some embodiments, the region of the cDNA that has a sequence that is complementary to the TaqMan® probe sequence is at or near the center of the cDNA molecule. In some embodiments, there are independently at least 2 nucleotides, such as at least 3 nucleotides, such as at least 4 nucleotides, such as at least 5 nucleotides of the cDNA at the 5'-end and at the 3'-end of the region of complementarity.

In some embodiments, Molecular Beacons can be used to detect and quantitate PCR products. Like TaqMan® probes, Molecular Beacons use FRET to detect and quantitate a PCR product via a probe having a fluorescent dye and a quencher attached at the ends of the probe. Unlike TaqMan® probes, Molecular Beacons remain intact during the PCR cycles. Molecular Beacon probes form a stem-loop structure when free in solution, thereby allowing the dye and quencher to be in close enough proximity to cause fluorescence quenching. When the Molecular Beacon hybridizes to a target, the stem-loop structure is abolished so that the dye and the quencher become separated in space and the dye fluoresces. Molecular Beacons are available, e.g., from Gene Link™ (see http://www.genelink.com/newsite/products/mbintro.asp).

In some embodiments, Scorpion probes can be used as both sequence-specific primers and for PCR product detection and quantitation. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent dye molecule is attached to the 5'-end of the Scorpion probe, and a quencher is attached to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the dye on the 5'-end to fluoresce and generate a signal. Scorpion probes are available from, e.g, Premier Biosoft International (see http://www.premierbiosoft.com/tech_notes/Scorpion.html).

In some embodiments, labels that can be used on the FRET probes include colorimetric and fluorescent labels such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; *Marina* Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides useful in the preparation of RT-PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of RT-PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, dyes and other moieties, such as quenchers, are introduced into polynucleotide used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In other embodiments, the modified nucleotide includes one or more reactive groups that can react with a dye or quencher before, during, or after incorporation of the modified nucleotide into the nucleic acid. In specific embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In specific embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

Exemplary detectable moieties also include, but are not limited to, members of binding pairs. In some such embodiments, a first member of a binding pair is linked to a polynucleotide. The second member of the binding pair is linked to a detectable label, such as a fluorescent label. When the polynucleotide linked to the first member of the binding pair is incubated with the second member of the binding pair linked to the detectable label, the first and second members of the binding pair associate and the polynucleotide can be detected. Exemplary binding pairs include, but are not limited to, biotin and streptavidin, antibodies and antigens, etc.

In some embodiments, multiple target RNAs are detected in a single multiplex reaction. In some such embodiments, each probe that is targeted to a unique cDNA is spectrally distinguishable when released from the probe. Thus, each target RNA is detected by a unique fluorescence signal.

One skilled in the art can select a suitable detection method for a selected assay, e.g., a real-time RT-PCR assay. The selected detection method need not be a method described above, and may be any method.

4.2. Exemplary Compositions and Kits

In another aspect, compositions are provided. In some embodiments, compositions are provided for use in the methods described herein.

In some embodiments, a composition comprises at least one polynucleotide. In some embodiments, a composition comprises at least one primer. In some embodiments, a composition comprises at least one probe. In some embodiments, a composition comprises at least one primer and at least one probe.

In some embodiments, compositions are provided that comprise at least one target RNA-specific primer. The term "target RNA-specific primer" encompasses primers that have a region of contiguous nucleotides having a sequence that is (i) identically present in one of SEQ ID NOs: 1 to 41 or 133 to 211, (ii) complementary to the sequence of a region of contiguous nucleotides found in one of SEQ ID NOs: 1 to 41 or 133 to 211; (iii) complementary to the sequence of a region of contiguous nucleotides found in one of SEQ ID NOs: 345 to 388; or (iv) identically present in one of SEQ ID NOs: 345 to 388.

In some embodiments, compositions are provided that comprise at least one target RNA-specific probe. The term "target RNA-specific probe" encompasses probes that have a region of contiguous nucleotides having a sequence that is (i) identically present in one of SEQ ID NOs: 1 to 41 or 133 to 211, (ii) complementary to the sequence of a region of contiguous nucleotides found in one of SEQ ID NOs: 1 to 41 or 133 to 211; (iii) complementary to the sequence of a region of contiguous nucleotides found in one of SEQ ID NOs: 345 to 388; or (iv) identically present in one of SEQ ID NOs: 345 to 388.

In some embodiments, target RNA-specific primers and probes comprise deoxyribonucleotides. In other embodiments, target RNA-specific primers and probes comprise at least one nucleotide analog. Nonlimiting exemplary nucleotide analogs include, but are not limited to, analogs described herein, including LNA analogs and peptide nucleic acid (PNA) analogs. In some embodiments, target RNA-specific primers and probes comprise at least one nucleotide analog which increases the hybridization binding energy (e.g., an affinity-enhancing nucleotide analog, discussed above). In some embodiments, a target RNA-specific primer or probe in the compositions described herein binds to one target RNA in the sample. In some embodiments, a single primer or probe binds to multiple target RNAs, such as multiple isomirs.

In some embodiments, more than one primer or probe specific for a single target RNA is present in the compositions, the primers or probes capable of binding to overlapping or spatially separated regions of the target RNA.

It will be understood, even if not explicitly stated hereinafter, that in some embodiments in which the compositions described herein are designed to hybridize to cDNAs reverse transcribed from target RNAs, the composition comprises at least one target RNA-specific primer or probe (or region thereof) having a sequence that is identically present in a target RNA (or region thereof).

In some embodiments, a target RNA is capable of specifically hybridizing to at least one probe comprising a sequence selected from SEQ ID NOs: 1, 2, 3, 4, 5, 6, 7 and 8. In some embodiments, a target RNA is capable of specifically hybridizing to at least one nucleic acid probe comprising a sequence selected from SEQ ID NOs: 1, 2, 3, 4, 5, 6, 7, 8, 9, 10, 11 and 12. In some embodiments, a target RNA is capable of specifically hybridizing to at least one nucleic acid probe comprising a sequence selected from SEQ ID NOs: 142, 151, 153, 193, 194, 205, 172, 208, 210, and 211. In some embodiments, a target RNA is capable of specifically hybridizing to at least one nucleic acid probe comprising a sequence selected from SEQ ID NOs: 1, 5, 7, and 32. In some embodiments, a target RNA is capable of specifically hybridizing to at least one probe comprising a sequence selected from SEQ ID NOs: 1 to 41 and 133 to 211. In some embodiments, a target RNA comprises at least 15 contiguous nucleotides of a sequence selected from SEQ ID NOs: 345 to 388. In some embodiments, a target RNA comprises a sequence that is complementary to at least 15 contiguous nucleotides of a sequence selected from SEQ ID NOs: 1 to 41 and 133 to 211. In some embodiments, a target RNA, in its mature form, comprises fewer than 30 nucleotides. In some embodiments, a target RNA is a microRNA.

In some embodiments, the composition comprises a plurality of target RNA-specific primers and/or probes for each of at least 2, at least 3, at least 4, at least 5, at least 6, at least 7, or at least 8 target RNAs, the target RNAs comprising a region of contiguous nucleotides having a sequence that is identically present in one of SEQ ID NOs: 42, 43, 44, 45, 46, 47, 48, or 49. In some embodiments, the plurality includes a target RNA-specific primer and/or probe specific for each of at least 2, at least 3, at least 4, at least 5, at least 6, at least 7, at least 8, at least 9, at least 10, at least 11, or at least 12 target RNAs, the target RNAs comprising a region of contiguous nucleotides having a sequence that is identically present in one of SEQ ID NOs: 42, 43, 44, 45, 46, 47, 48, 49, 50, 51, 52, and 53. In some embodiments, the plurality includes a target RNA-specific primer and/or probe specific for each of at least 2, at least 3, at least 4, at least 5, at least 6, at least 7, at least 8, at least 9, at least 10, at least 15, at least 20, at least 25, at least 30, at least 40, at least 50, at least 75, or at least 100 target RNAs comprising a region of contiguous nucleotides having a sequence that is identically present in one of SEQ ID NOs: 42 to 82 or 226 to 317. It will be understood that, in some embodiments, target RNAs described herein comprise a sequence identically present in a sequence set forth in Table 2 or Table 12, except that thymine (T) bases in the sequences shown in Table 2 or Table 12 are replaced by uracil (U) bases in the target RNAs.

In some embodiments, a composition is an aqueous composition. In some embodiments, the aqueous composition comprises a buffering component, such as phosphate, tris, HEPES, etc., and/or additional components, as discussed below. In some embodiments, a composition is dry, for example, lyophilized, and suitable for reconstitution by addition of fluid. A dry composition may include a buffering component and/or additional components.

In some embodiments, a composition comprises one or more additional components. Additional components include, but are not limited to, salts, such as NaCl, KCl, and $MgCl_2$; polymerases, including thermostable polymerases; dNTPs; RNase inhibitors; bovine serum albumin (BSA) and the like; reducing agents, such as β-mercaptoethanol; EDTA and the like; etc. One skilled in the art can select suitable composition components depending on the intended use of the composition.

In some embodiments, an addressable microarray component is provided that comprises target RNA-specific probes attached to a substrate.

Microarrays for use in the methods described herein comprise a solid substrate onto which the probes are covalently or non-covalently attached. In some embodiments, probes capable of hybridizing to one or more target RNAs or cDNAs are attached to the substrate at a defined location ("addressable array"). Probes can be attached to the substrate in a wide variety of ways, as will be appreciated by those in the art. In some embodiments, the probes are synthesized first and subsequently attached to the substrate. In other embodiments, the probes are synthesized on the substrate. In some embodiments, probes are synthesized on the substrate surface using techniques such as photopolymerization and photolithography.

In some embodiments, the solid substrate is a material that is modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. In some embodiments, the substrates allow optical detection without appreciably fluorescing.

In some embodiments, the substrate is planar. In other embodiments, probes are placed on the inside surface of a tube, such as for flow-through sample analysis to minimize sample volume. In other embodiments, probes can be in the wells of multi-well plates. In still other embodiments, probes can be attached to an addressable microbead array. In yet other embodiments, the probes can be attached to a flexible substrate, such as a flexible foam, including closed cell foams made of particular plastics.

The substrate and the probe can each be derivatized with functional groups for subsequent attachment of the two. For example, in some embodiments, the substrate is derivatized with one or more chemical functional groups including, but not limited to, amino groups, carboxyl groups, oxo groups and thiol groups. In some embodiments, probes are attached directly to the substrate through one or more functional groups. In some embodiments, probes are attached to the substrate indirectly through a linker (i.e., a region of contiguous nucleotides that space the probe regions involved in hybridization and detection away from the substrate surface). In some embodiments, probes are attached to the solid support through the 5' terminus. In other embodiments, probes are attached through the 3' terminus. In still other embodiments, probes are attached to the substrate through an internal nucleotide. In some embodiments the probe is attached to the solid support non-covalently, e.g., via a biotin-streptavidin interaction, wherein the probe biotinylated and the substrate surface is covalently coated with streptavidin.

In some embodiments, the compositions comprise a microarray having probes attached to a substrate, wherein at least one of the probes (or a region thereof) comprises a sequence that is identically present in, or complementary to a region of, one of SEQ ID NOs: 1 to 41, 133 to 211, or SEQ ID NOs: 345 to 388. In some embodiments, at least 2, at least 5, at least 10, at least 15, at least 20, at least 25, at least 30, at least 40, at least 50, or at least 100 of the probes comprise a sequence that is identically present in, or complementary to a region of, one of SEQ ID NOs: 1 to 41, 133 to 211, or 345 to 388. In some embodiments, the microarray comprises at least one target RNA-specific probe comprising a sequence that is identically present in, or complementary to a region of, one of SEQ ID NOs: 1 to 41, 133 to 211, or 345 to 388 and at least one target RNA-specific probe comprising a sequence that is identically present in, or complementary to a region of, a target RNA set forth in Table 3. In some embodiments, the microarray comprises each target RNA-specific probe at only one location on the microarray. In some embodiments, the microarray comprises at least one target RNA-specific probe at multiple locations on the microarray.

As used herein, the terms "complementary" or "partially complementary" to a target RNA (or target region thereof), and the percentage of "complementarity" of the probe sequence to that of the target RNA sequence is the percentage "identity" to the reverse complement of the sequence of the target RNA. In determining the degree of "complementarity" between probes used in the compositions described herein (or regions thereof) and a target RNA, such as those disclosed herein, the degree of "complementarity" is expressed as the percentage identity between the sequence of the probe (or region thereof) and the reverse complement of the sequence of the target RNA that best aligns therewith. The percentage is calculated by counting the number of aligned bases that are identical as between the 2 sequences, dividing by the total number of contiguous nucleotides in the probe, and multiplying by 100.

In some embodiments, the microarray comprises at least one probe having a region with a sequence that is fully complementary to a target region of a target RNA. In other embodiments, the microarray comprises at least one probe having a region with a sequence that comprises one or more base mismatches when compared to the sequence of the best-aligned target region of a target RNA.

In some embodiments, the microarray comprises at least one probe having a region of at least 10, at least 11, at least 13, at least 14, at least 15, at least 16, at least 17, at least 18, at least 19, at least 20, at least 21, at least 22, at least 23, at least 24, or at least 25 contiguous nucleotides with a sequence that is identically present in, or complementary to a region of, one of SEQ ID NOs: 1 to 41 or 133 to 211. In some embodiments, the microarray comprises at least one probe having a region of at least 10, at least 11, at least 13, at least 14, at least 15, at least 16, at least 17, at least 18, at least 19, at least 20, at least 21, at least 22, at least 23, at least 24, or at least 25 contiguous nucleotides with a sequence that is identically present in, or complementary to a region of, one of SEQ ID NOs: 1 to 41 or 133 to 211, and at least one probe comprising a region of at least 10, at least 11, at least 13, at least 14, at least 15, at least 16, at least 17, at least 18, at least 19, at least 20, at least 21, at least 22, at least 23, at least 24, or at least 25 contiguous nucleotides having a sequence that is identically present in, or complementary to a region of, a target RNA set forth in Table 3.

In some embodiments, the microarray comprises at least one probe having a region with a sequence that is identically present in, or complementary to a region of, one of SEQ ID NOs: 1, 2, 3, 4, 5, 6, 7, or 8. In some embodiments, the microarray comprises at least one, at least two, at least three, at least five, or eight probes that each comprise a region with a sequence that is identically present in, or complementary to a region of, one of SEQ ID NOs: 1, 2, 3, 4, 5, 6, 7 or 8. In some embodiments, the microarray further comprises additional probes that do not have a region with a sequence that is identically present in, or complementary to a region of, one of SEQ ID NOs: 1, 2, 3, 4, 5, 6, 7 and 8.

In some embodiments, the microarray comprises at least one probe having a region with a sequence that is identically present in, or complementary to a region of, one of SEQ ID NOs: 1, 2, 3, 4, 5, 6, 7, 8, 9, 10, 11 or 12. In some embodiments, the microarray comprises at least one, at least two, at least three, at least five, at least eight, at least 10, or at least 12 probes that each comprise a region with a sequence that is identically present in, or complementary to a region of, one of SEQ ID NOs: 1, 2, 3, 4, 5, 6, 7, 8, 9, 10, 11 or 12. In some embodiments, the microarray further comprises additional probes that do not have a region with a sequence that is identically present in, or complementary to a region of, one of SEQ ID NOs: 1, 2, 3, 4, 5, 6, 7, 8, 9, 10, 11 or 12.

In some embodiments, the microarray comprises at least one probe having a region with a sequence that is identically present in, or complementary to a region of, one of SEQ ID NOs: 142, 151, 153, 193, 194, 205, 172, 208, 210, and 211. In some embodiments, the microarray comprises at least one, at least two, at least three, at least five, at least eight, or at least 10 probes that each comprise a region with a sequence that is identically present in, or complementary to a region of, one of SEQ ID NOs: 142, 151, 153, 193, 194, 205, 172, 208, 210, and 211. In some embodiments, the microarray further comprises additional probes that do not have a region with a sequence that is identically present in, or complementary to a region of, one of SEQ ID NOs: 142, 151, 153, 193, 194, 205, 172, 208, 210, and 211.

In some embodiments, the microarray comprises at least one probe having a region with a sequence that is identically present in, or complementary to a region of, one of SEQ ID NOs: 1, 5, 7, or 32. In some embodiments, the microarray comprises at least one, at least two, at least three, or at least four probes that each comprise a region with a sequence that is identically present in, or complementary to a region of, one of SEQ ID NOs: 1, 5, 7, or 32. In some embodiments, the microarray further comprises additional probes that do not have a region with a sequence that is identically present in, or complementary to a region of, one of SEQ ID NOs: 1, 5, 7, or 32.

In some embodiments, the microarrays comprise probes having a region with a sequence that is complementary to target RNAs that comprise a substantial portion of the human miRNome (i.e., the publicly known microRNAs that have been accessioned by others into miRBase (http://microrna.sanger.ac.uk/ at the time the microarray is fabricated), such as at least about 60%, at least about 70%, at least about 80%, at least about 90%, even at least about 95% of the human miRNome. In some embodiments, the microarrays comprise probes that have a region with a sequence that is identically present in target RNAs that comprise a substantial portion of the human miRNome, such as at least about 60%, at least about 70%, at least about 80%, at least about 90%, even at least about 95% of the human miRNome.

In some embodiments, components are provided that comprise probes attached to microbeads, such as those sold by Luminex, each of which is internally dyed with red and infrared fluorophores at different intensities to create a unique signal for each bead. In some embodiments, the compositions useful for carrying out the methods described herein include a plurality of microbeads, each with a unique spectral signature. Each uniquely labeled microbead is attached to a unique target RNA-specific probe such that the unique spectral signature from the dyes in the bead is associated with a particular probe sequence. Nonlimiting exemplary probe sequences include SEQ ID NOs: 1 to 41 and 133 to 211. Nonlimiting exemplary probe sequences also include probes comprising a region that is identically present in, or complementary to, a sequence selected from SEQ ID NOs: 1 to 41, 133 to 211, and SEQ ID NOs: 345 to 388. In some embodiments, a probe sequence comprises at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides that are identically present in, or complementary to a region of, SEQ ID NOs: 1 to 41, 133 to 211, and SEQ ID NOs: 345 to 388.

In some embodiments, a uniquely labeled microbead has attached thereto a probe having a region with a sequence that is identically present in, or complementary to a region of, one of SEQ ID NOs: 1 to 41, 133 to 211, or 345 to 388. In other embodiments, the uniquely labeled microbead has attached thereto a probe having a region with a sequence that comprises one or more base mismatches when compared to the most similar sequence selected from SEQ ID NOs: 1 to 41, 133 to 211, and 345 to 388, and sequences complementary to SEQ ID NOs: 1 to 41, 133 to 211.

In some embodiments, a composition is provided that comprises a plurality of uniquely labeled microbeads, wherein at least one microbead has attached thereto a probe having a region of at least 10, at least 11, at least 13, at least 14, at least 15, at least 16, at least 17, at least 18, at least 19, at least 20, at least 21, at least 22, at least 23, at least 24, or at least 25 contiguous nucleotides with a sequence that is identically present in, or complementary to a region of, one of SEQ ID NOs: 1 to 41, 133 to 211 or 345 to 388. In some embodiments, a composition comprises a plurality of uniquely labeled microbeads, wherein at least one of the microbeads has attached thereto a probe having a region of at least 10, at least 11, at least 13, at least 14, at least 15, at least 16, at least 17, at least 18, at least 19, at least 20, at least 21, at least 22, at least 23, at least 24, or at least 25 contiguous nucleotides with a sequence that is identically present in, or complementary to a region of, one of SEQ ID NOs: 1 to 41, 133 to 211, or 345 to 388, and at least a second microbead having attached thereto a probe comprising a region of at least 10, at least 11, at least 13, at least 14, at least 15, at least 16, at least 17, at least 18, at least 19, at least 20, at least 21, at least 22, at least 23, at least 24, or at least 25 contiguous nucleotides having a sequence that is identically present in, or complementary to a region of, a target RNA set forth in Table 3.

In some embodiments, the compositions comprise a plurality of uniquely labeled microbeads, at least one of which has attached thereto a target RNA-specific probe having a region with a sequence that is identically present in, or complementary to a region of, one of SEQ ID NOs: 1, 2, 3, 4, 5, 6, 7, or 8. In some embodiments, the compositions comprise at least two, at least three, at least five, or at least 8 uniquely labeled microbeads that each have attached thereto a unique target RNA-specific probe having a region with a sequence that is identically present in, or complementary to a region of, a different one of SEQ ID NOs: 1, 2, 3, 4, 5, 6, 7 or 8. In some embodiments, the composition comprises at least one uniquely labeled microbead having attached thereto a target RNA-specific probe having a region with a sequence that is not present in, or complementary to a region of, any of SEQ ID NOs: 1, 2, 3, 4, 5, 6, 7, or 8.

In some embodiments, the compositions comprise plurality of uniquely labeled microbeads, wherein at least one microbead has attached thereto a probe having a region with a sequence that is identically present in, or complementary to a region of, one of SEQ ID NOs: 1, 2, 3, 4, 5, 6, 7, 8, 9, 10, 11 or 12. In some embodiments, the compositions comprise at least two, at least three, at least five, at least eight, at least 10, or at least 12 uniquely labeled microbeads that each have attached thereto a unique target RNA-specific probe having a region with a sequence that is identically present in, or complementary to a region of, a different one of SEQ ID NOs: 1, 2, 3, 4, 5, 6, 7, 8, 9, 10, 11 or 12. In some embodiments, the composition comprises at least one uniquely labeled microbead having attached thereto a target RNA-specific probe having a region with a sequence that is not present in, or complementary to a region of, any of SEQ ID NOs: 1, 2, 3, 4, 5, 6, 7, 8, 9, 10, 11 or 12.

In some embodiments, the compositions comprise plurality of uniquely labeled microbeads, wherein at least one microbead has attached thereto a probe having a region with a sequence that is identically present in, or complementary to a region of, one of SEQ ID NOs: 142, 151, 153, 193, 194, 205, 172, 208, 210, and 211. In some embodiments, the compositions comprise at least two, at least three, at least five, at least eight, or at least 10 uniquely labeled microbeads that each have attached thereto a unique target RNA-specific probe having a region with a sequence that is identically present in, or complementary to a region of, a different one of SEQ ID NOs: 142, 151, 153, 193, 194, 205, 172, 208, 210, and 211. In some embodiments, the composition comprises at least one uniquely labeled microbead having attached thereto a target RNA-specific probe having a region with a sequence that is not present in, or complementary to a region of, any of SEQ ID NOs: 142, 151, 153, 193, 194, 205, 172, 208, 210, and 211.

In some embodiments, the compositions comprise plurality of uniquely labeled microbeads, wherein at least one microbead has attached thereto a probe having a region with a sequence that is identically present in, or complementary to a region of, one of SEQ ID NOs: 1, 5, 7, or 32. In some embodiments, the compositions comprise at least two, at least three, or at least four uniquely labeled microbeads that each have attached thereto a unique target RNA-specific probe having a region with a sequence that is identically present in, or complementary to a region of, a different one of SEQ ID NOs: 1, 5, 7, or 32. In some embodiments, the composition comprises at least one uniquely labeled microbead having attached thereto a target RNA-specific probe having a region with a sequence that is not present in, or complementary to a region of, any of SEQ ID NOs: 1, 5, 7, or 32.

In some embodiments, the compositions comprise a plurality of uniquely labeled microbeads, wherein the plurality comprises at least one microbead having attached thereto a probe having a region with a sequence that is identically present in, or complementary to a region of, one of SEQ ID NOs: 1 to 41, 133 to 211, or SEQ ID NOs: 345 to 388. In some embodiments, the plurality comprises at least two, at least five, at least 10, at least 15, at least 20, at least 25, at least 30, at least 40, at least 50, at least 60, at least 75, or at least 100 microbeads each of which having attached thereto a probe having a region with a sequence that is identically present in, or complementary to a region of, one of SEQ ID NOs: 1 to 41, 133 to 211, or 345 to 388. In some embodiments, a composition comprises at least one uniquely labeled microbead having attached thereto a target RNA-specific probe having a region with a sequence that is not present in, or complementary to a region of, any of SEQ ID NOs: 1 to 41 or 133 to 211.

In some embodiments, the compositions comprise a plurality of uniquely labeled microbeads, at least one of which has attached thereto a probe having a region with a sequence that identically present in, or complementary to a region of, one of SEQ ID NOs: 1 to 41, 133 to 211, or 345 to 388, and at least a second bead that has attached thereto a probe having a region with a sequence that is identically present in, or complementary to a region of, a target RNA set forth in Table 3.

In some embodiments, the compositions comprise a plurality of uniquely labeled microbeads, each of which has attached thereto a unique probe having a region that is complementary to target RNAs that comprise a substantial portion of the human miRNome, such as at least about 60%, at least about 70%, at least about 80%, at least about 90%, or at least about 95% of the human miRNome. In some embodiments, the compositions comprise a plurality of uniquely labeled microbeads having attached thereto a unique probe having a region with a sequence that is identically present in target RNAs that comprise a substantial portion of the human miRNome, such as at least about 60%, at least about 70%, at least about 80%, at least about 90%, or at least about 95% of the human miRNome.

In some embodiments, compositions are provided that comprise at least one polynucleotide for detecting at least one target RNA. In some embodiments, the polynucleotide is used as a primer for a reverse transcriptase reaction. In some embodiments, the polynucleotide is used as a primer for amplification. In some embodiments, the polynucleotide is used as a primer for RT-PCR. In some embodiments, the polynucleotide is used as a probe for detecting at least one target RNA. In some embodiments, the polynucleotide is detectably labeled. In some embodiments, the polynucleotide is a FRET probe. In some embodiments, the polynucleotide is a TaqMan® probe, a Molecular Beacon, or a Scorpion probe.

In some embodiments, a composition comprises at least one FRET probe having a sequence that is identically present in, or complementary to a region of, one of SEQ ID NOs: 1 to 41, 133 to 211, or 345 to 388. In some embodiments, a composition comprises at least two, at least five, at least 10, at least 15, at least 20, at least 25, at least 30, at least 40, at least 50, at least 60, at least 75, or at least 100 FRET probes, each of which has a sequence that is identically present in, or complementary to a region of, a different one of SEQ ID NOs: 1 to 41, 133 to 211, or 345 to 388. In some embodiments, a FRET probe is labeled with a donor/acceptor pair such that when the probe is digested during the PCR reaction, it produces a unique fluorescence emission that is associated with a specific target RNA. In some embodiments, when a composition comprises multiple FRET probes, each probe is labeled with a different donor/acceptor pair such that when the probe is digested during the PCR reaction, each one produces a unique fluorescence emission that is associated with a specific probe sequence and/or target RNA. In some embodiments, the sequence of the FRET probe is complementary to a target region of a target RNA. In other embodiments, the FRET probe has a sequence that comprises one or more base mismatches when compared to the sequence of the best-aligned target region of a target RNA.

In some embodiments, a composition comprises a FRET probe consisting of at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides, wherein at least a portion of the sequence is identically present in, or complementary to a region of, one of SEQ ID NOs: 1 to 41, 133 to 211, and 345 to 388. In some embodiments, at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides of the FRET probe are identically present in, or complementary to a region of, one of SEQ ID NOs: 1 to 41, 133 to 211, and 345 to 388. In some embodiments, the FRET probe has a sequence with one, two or three base mismatches when compared to the sequence or complement of one of SEQ ID NOs: 1 to 41 or 133 to 211.

In some embodiments, the compositions further comprise a FRET probe consisting of at least 10, at least 11, at least 13, at least 14, at least 15, at least 16, at least 17, at least 18, at least 19, at least 20, at least 21, at least 22, at least 23, at least 24, or at least 25 contiguous nucleotides, wherein the FRET probe comprises a sequence that is identically present in, or complementary to a region of, a region of a target RNA set forth in Table 3. In some embodiments, the FRET probe is identically present in, or complementary to a region of, at least at least 10, at least 11, at least 13, at least 14, at least 15, at least 16, at least 17, at least 18, at least 19, at least 20, at least 21, at least 22, at least 23, or at least 24 contiguous nucleotides of a target RNA set forth in Table 3.

In some embodiments, the compositions comprise at least one target RNA-specific FRET probe comprising a sequence that is identically present in, or complementary to a region of, one of SEQ ID NOs: 1, 2, 3, 4, 5, 6, 7, or 8. In some embodiments, the compositions comprise at least two, at least three, at least five, or at least 8 uniquely labeled target RNA-specific FRET probes, each comprising a sequence that is identically present in, or complementary to a region of, a different one of SEQ ID NOs: 1, 2, 3, 4, 5, 6, 7 and 8.

In some embodiments, the compositions comprise at least one target RNA-specific FRET probe comprising a sequence that is identically present in, or complementary to a region of, one of SEQ ID NOs: 1, 2, 3, 4, 5, 6, 7, 8, 9, 10, 11 or 12. In some embodiments, the compositions comprise at least two, at least three, at least five, at least eight, at least 10, or at least 12 uniquely labeled target RNA-specific FRET probes, each of which comprises a sequence that is identically present in, or complementary to a region of, a different one of SEQ ID NOs: 1, 2, 3, 4, 5, 6, 7, 8, 9, 10, 11 and 12.

In some embodiments, the compositions comprise at least one target RNA-specific FRET probe comprising a sequence that is identically present in, or complementary to a region of, one of SEQ ID NOs: 142, 151, 153, 193, 194, 205, 172, 208, 210, and 211. In some embodiments, the compositions comprise at least two, at least three, at least five, at least eight, at least nine, or at least 10 uniquely labeled target RNA-specific FRET probes, each of which comprises a sequence that is identically present in, or complementary to a region of, a different one of SEQ ID NOs: 142, 151, 153, 193, 194, 205, 172, 208, 210, and 211.

In some embodiments, the compositions comprise at least one target RNA-specific FRET probe comprising a sequence that is identically present in, or complementary to a region of, one of SEQ ID NOs: 1, 5, 7, or 32. In some embodiments, the compositions comprise at least two, at least three, or at least four uniquely labeled target RNA-specific FRET probes, each of which comprises a sequence that is identically present in, or complementary to a region of, a different one of SEQ ID NOs: 1, 5, 7, or 32.

In some embodiments, a kit comprises a polynucleotide discussed above. In some embodiments, a kit comprises at least one primer and/or probe discussed above. In some embodiments, a kit comprises at least one polymerase, such as a thermostable polymerase. In some embodiments, a kit comprises dNTPs. In some embodiments, kits for use in the real time RT-PCR methods described herein comprise one or more target RNA-specific FRET probes and/or one or more primers for reverse transcription of target RNAs and/or one or more primers for amplification of target RNAs or cDNAs reverse transcribed therefrom.

In some embodiments, one or more of the primers and/or probes is "linear". A "linear" primer refers to a polynucleotide that is a single stranded molecule, and typically does not comprise a short region of, for example, at least 3, 4 or 5 contiguous nucleotides, which are complementary to another region within the same polynucleotide such that the primer forms an internal duplex. In some embodiments, the primers for use in reverse transcription comprise a region of at least 4, such as at least 5, such as at least 6, such as at least 7 or more contiguous nucleotides at the 3'-end that has a sequence that is complementary to region of at least 4, such as at least 5, such as at least 6, such as at least 7 or more contiguous nucleotides at the 5'-end of a target RNA.

In some embodiments, a kit comprises one or more pairs of linear primers (a "forward primer" and a "reverse primer") for amplification of a cDNA reverse transcribed from a target RNA. Accordingly, in some embodiments, a first primer comprises a region of at least 4, at least 5, at least 6, at least 7, at least 8, at least 9, or at least 10 contiguous nucleotides having a sequence that is identical to the sequence of a region of at least 4, at least 5, at least 6, at least 7, at least 8, at least 9, or at least 10 contiguous nucleotides at the 5'-end of a target RNA. Furthermore, in some embodiments, a second primer comprises a region of at least 4, at least 5, at least 6, at least 7, at least 8, at least 9, or at least 10 contiguous nucleotides having a sequence that is complementary to the sequence of a region of at least 4, at least 5, at least 6, at least 7, at least 8, at least 9, or at least 10 contiguous nucleotides at the 3'-end of a target RNA. In some embodiments, the kit comprises at least a first set of primers for amplification of a cDNA that is reverse transcribed from a target RNA capable of specifically hybridizing to a nucleic acid comprising a sequence identically present in one of SEQ ID NOs: 1 to 41 and 133 to 211 and/or a cDNA that is reverse transcribed from a target RNA that comprises at least 15 contiguous nucleotides of a sequence selected from SEQ ID NOs: 345 to 388. In some embodiments, the kit further comprises at least a second set of primers for amplification of a cDNA that is reverse transcribed from a target RNA set forth in Table 3.

In some embodiments, the kit comprises at least two, at least five, at least 10, at least 15, at least 20, at least 25, at least 30, at least 40, at least 50, at least 60, at least 75, or at least 100 sets of primers, each of which is for amplification of a cDNA that is reverse transcribed from a different target RNA capable of specifically hybridizing to a sequence selected from SEQ ID NOs: 1 to 41 and 133 to 211 and/or a cDNA that is reverse transcribed from a target RNA that comprises at least 15 contiguous nucleotides of a sequence selected from SEQ ID NOs: 345 to 388. In some embodiments, the kit comprises at least one set of primers that is capable of amplifying more than one cDNA reverse transcribed from a target RNA in a sample.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the compositions described herein also comprise probes, and in the case of RT-PCR, primers, that are specific to one or more housekeeping genes for use in normalizing the quantities of target RNAs. Such probes (and primers) include those that are specific for one or more products of housekeeping genes selected from U6 snRNA, ACTB, B2M, GAPDH, GUSB, HPRT1, PPIA, RPLP, RRN18S, TBP, TUBB, UBC, YWHA (TATAA), PGK1, and RPL4.

In some embodiments, the kits for use in real time RT-PCR methods described herein further comprise reagents for use in the reverse transcription and amplification reactions. In some embodiments, the kits comprise enzymes such as reverse transcriptase, and a heat stable DNA polymerase, such as Taq polymerase. In some embodiments, the kits further comprise deoxyribonucleotide triphosphates (dNTP) for use in reverse transcription and amplification. In further embodiments, the kits comprise buffers optimized for specific hybridization of the probes and primers.

4.2.1. Exemplary Normalization of RNA Levels

In some embodiments, quantitation of target RNA expression levels requires assumptions to be made about the total RNA per cell and the extent of sample loss during sample preparation. In order to correct for differences between different samples or between samples that are prepared under different conditions, the quantities of target RNAs in some embodiments are normalized to the expression of at least one endogenous housekeeping gene.

Appropriate genes for use as reference genes in the methods described herein include those as to which the quantity of the product does not vary between normal and dysplastic or cancerous cervical cells, or between different cell lines or under different growth and sample preparation conditions. In some embodiments, endogenous housekeeping genes useful as normalization controls in the methods described herein include, but are not limited to, U6 snRNA, RNU44, RNU 48, and U47. In typical embodiments, the at least one endogenous housekeeping gene for use in normalizing the measured quantity of microRNAs is selected from U6 snRNA, U6 snRNA, RNU44, RNU 48, and U47. In some embodiments, one housekeeping gene is used for normalization. In some embodiments, more than one housekeeping gene is used for normalization.

4.2.2. Exemplary Qualitative Methods

In some embodiments, methods comprise detecting a qualitative change in a target RNA profile generated from a clinical sample of human cervical cells as compared to a normal target RNA profile (in some exemplary embodiments, a target RNA profile of a control sample). Some qualitative changes in the expression profile are indicative of the presence of cervical dysplasia in a sample of human cervical cells. Various qualitative changes in the expression profile are indicative of the propensity to proceed to cervical cancer. The term "target RNA profile" refers to a set of data regarding the concurrent expression of a plurality of target RNAs in the same sample.

In some embodiments, at least one, at least two, at least three, at least four, at least five, at least six, at least seven, or at least eight of the target RNAs of the plurality of target RNAs are capable of specifically hybridizing to a nucleic acid comprising a sequence selected from SEQ ID NOs: 1, 2, 3, 4, 5, 6, 7 and 8. In some embodiments, at least one, at least two, at least three, at least four, at least five, at least six, at least seven, at least eight, at least nine, at least 10, at least 11, or at least 12 of the target RNAs of the plurality of target RNAs is capable of specifically hybridizing to a nucleic acid comprising a sequence selected from SEQ ID NOs: 1, 2, 3, 4, 5, 6, 7, 8, 9, 10, 11 and 12. In some embodiments, at least one, at least two, at least three, at least four, at least five, at least six, at least seven, at least eight, at least nine, or at least 10 of the target RNAs of the plurality of target RNAs is capable of specifically hybridizing to a nucleic acid comprising a sequence selected from SEQ ID NOs: 142, 151, 153, 193, 194, 205, 172, 208, 210, and 211. In some embodiments, at least one, at least two, at least three, or at least four of the target RNAs of the plurality of target RNAs is capable of specifically hybridizing to a nucleic acid comprising a sequence selected from SEQ ID NOs: 1, 5, 7, and 32.

In some embodiments, at least one, at least two, at least five, at least 10, at least 15, at least 20, at least 25, at least 30, at least 40, at least 50, at least 60, at least 75, or at least 100 of the plurality of target RNAs is capable of specifically hybridizing to a nucleic acid comprising a sequence selected from SEQ ID NOs: 1 to 41 and 133 to 211. In some embodiments, at least one, at least two, at least five, at least 10, at least 15, at least 20, at least 25, at least 30, at least 40 of the plurality of target RNAs comprises at least 15 contiguous nucleotides of a sequence selected from SEQ ID NOs: 345 to 388. In some embodiments, at least one, at least two, at least five, at least 10, at least 15, at least 20, at least 25, at least 30, at least 40, at least 50, at least 60, at least 75, or at least 100 of the plurality of target RNAs comprises a sequence that is complementary to at least 15 contiguous nucleotides of a sequence selected from SEQ ID NOs: 1 to 41 and 133 to 211. In some embodiments, a target RNA, in its mature form, comprises fewer than 30 nucleotides. In some embodiments, a target RNA is a microRNA.

Qualitative expression data for use in preparing target RNA expression profiles is obtained using any suitable analytical method, including the analytical methods presented herein.

In some embodiments, for example, concurrent expression data are obtained using, e.g., a microarray, as described above. Thus, in addition to use for quantitative expression level assays of specific target RNAs as described above, a microarray comprising probes having sequences that are complementary to a substantial portion of the miRNome may be employed to carry out target RNA gene expression profiling, for analysis of target RNA expression patterns.

In some embodiments, distinct target RNA signatures are associated with established markers for cervical dysplasia, or directly with the presence of cervical dysplasia. In some embodiments, distinct target RNA signatures are associated with established markers for CIN-1, CIN-2 or CIN-3 cervical dysplasia, or directly with the level of severity of cervical dysplasia. In some embodiments, distinct target RNA signatures are associated with established markers for cervical dysplasia likely to progress to carcinoma, or directly with cervical dysplasia that is likely to progress to carcinoma. In some embodiments, distinct target RNA signatures are associated with HPV infection and/or integration into the genome of the host cell. In some embodiments, distinct target RNA signatures are associated with established markers for cervical cancer, or directly with the presence of cervical cancer.

According to the expression profiling method, in some embodiments, total RNA from a sample from a subject suspected of having cervical dysplasia is quantitatively reverse transcribed to provide a set of labeled polynucleotides complementary to the RNA in the sample. The polynucleotides are then hybridized to a microarray comprising target RNA-specific probes to provide a hybridization profile for the sample. The result is a hybridization profile for the sample representing the expression pattern of target RNAs in the sample. The hybridization profile comprises the signal from the binding of the polynucleotides reverse transcribed from the sample to the target RNA-specific probes in the microarray. In some embodiments, the profile is recorded as the presence or absence of binding (signal vs. zero signal). In some embodiments, the profile recorded includes the intensity of the signal from each hybridization. The profile is compared to the hybridization profile generated from a normal, i.e., noncancerous, or in some embodiments, a control sample. An alteration in the signal is indicative of the presence of cervical dysplasia or cervical cancer in the subject.

4.3. Exemplary Additional Target RNAs

In some embodiments, in combination with detecting one or more target RNAs that are capable of specifically hybridizing to a nucleic acid comprising a sequence selected from SEQ ID NOs:1 to 41 and 133 to 211 and/or detecting one or more target RNAs comprising at least 15 contiguous nucleotides of a sequence selected from SEQ ID NOs: 345 to 388 and/or detecting one or more target RNAs that comprise a sequence that is complementary to at least 15 contiguous nucleotides of a sequence selected from SEQ ID NOs:1 to 41 and 133 to 211, methods herein further comprise detecting the level(s) of expression of at least one other marker associated with cervical dysplasia or HPV integration.

Accordingly, in some embodiments, the methods described herein further comprise detecting increased expression of any one or more of miR-21, miR-31, miR-182, miR-183, miR-146a, miR-155, and miR-205. In some embodiments, the methods described herein further comprise detecting increased expression of any one or more of miR-663, miR-765, miR-92b*, miR-936, miR-9, miR-199a*, miR-199a, miR-199b, miR-145, miR-133a, miR-133b, miR-214, miR-127, miR-210, miR-301, miR-142-3p, miR-142-5p, miR-194, miR-215 and miR-32.

In some embodiments, the methods described herein further comprise detecting altered expression of target RNAs associated with HPV integration sites. As used herein, the term "associated with" a given HPV integration site means that the target RNA gene is located in close proximity to the HPV integration site; i.e., when the target RNA is located within the same chromosomal band or within 3 megabases (3 Mb), preferably within 2.5 Mb, of the HPV integration site. Thus, in some embodiments, the methods further comprise detecting increased expression of target RNAs associated with HPV integration sites, such as fragile sites which are preferential targets for HPV16 associated with cervical tumors. Such target RNAs include: miR-186, miR-101 (associated with FRA1A on chromosome 1p36 and FRA1C on chromosome 1p31); miR-194 and miR-215 (associated with FRA1F on chromosome 1q21 and FRA1H on chromosome 1q42.1); miR-106b, miR-25 and miR93 (associated with FRAXF on chromosome 7q22); miR-29b, miR-29a, miR-96, miR-182-5p, miR-182-3p, miR-183, and miR-129-1 (associated with FRA7G on chromosome 7q31.2 and FRA7H on chromosome 7q32.3); let7-1a, let7-d, let-7f-1, miR-23b, miR-24-1, and miR-27b (associated with FRA9D on chromosome 9q22.1); miR-32 (associated with FRA9E on chromosome 9q32-33.1); miR159-1 and miR-192 (associated with FRA11A on chromosome 11q13.3); miR-125b-1, let-7a-2, and miR-100 (associated with FRA11B on chromosome 11q23.3); miR-196-2 and miR-148b (associated with FRA12A on chromosome 12q13.1); miR-190 (associated with FRA15A on chromosome 15q22); miR-21, miR-301, miR-142-5p, and miR-142-3p (associated with FRA17B on chromosome 17q23.1); and miR-105-1 and miR-175 (associated with FRAXF on chromosome Xq28).

In other embodiments, the methods described herein further comprise detecting altered expression of cervical cancer-associated small RNAs with non-canonical hairpins.

In other embodiments, the methods described herein further comprise detecting increased expression of the mRNA of one or more of the following genes: BIRC5, IGF2BP3, TERC, CDKN2A, MCM5, TOP2A, MYBL2, PIK3CA, DROSHA, MKI67, MMP9, and MCM2. In some embodiments, the methods described herein further comprise detecting increased expression of the mRNA of one or more of the following genes: CDKN2A, MKI67, TOP2A, and MCM5. In some embodiments, the methods described herein further comprise detecting increased expression of the mRNA of one or more of the following genes: CDKN2A, MKI67, TOP2A, MCM5, BIRC5, MMP9, and MCM2. Appropriate genes for use as reference genes when detecting mRNA expression include those as to which the quantity of the product does not vary between normal and cancerous cervical cells, or between different cell lines or under different growth and sample preparation conditions. In some embodiments, endogenous housekeeping genes useful as normalization controls in the methods described herein include, but are not limited to, ACTB, B2M, GAPDH, GUSB, HPRT1, PPIA, RPLP, TBP, TUBB, UBC, PGK1 and RPL4. In typical embodiments, the at least one endogenous housekeeping gene for use in normalizing the measured quantity of mRNAs is selected from GAPDH, TBP and ACTB. In some embodiments, one housekeeping gene is used for normalization. In some embodiments, more than one housekeeping gene is used for normalization.

In alternative embodiments, the methods described herein further comprise detecting chromosomal codefendants, i.e., target RNAs clustered near each other in the human genome which tend to be regulated together. Accordingly, in further embodiments, the methods comprise detecting the expression of one or more target microRNAs, each situated within the chromosome no more than 50,000 bp from the chromosomal location of the pre-microRNA sequences in Table 2.

The following examples are for illustration purposes only, and are not meant to be limiting in any way.

5. EXAMPLES

5.1 Example 1: MicroRNAs from Cervical Cancer Cell Lines

Using microarray analysis, 41 distinct microRNAs were demonstrated to be overexpressed in cervical cell lines.
Cell Lines Total RNA was prepared from eight different cell lines of cervical origin that are commonly used in studies of cervical dysplasia and/or carcinoma. The RNA was used for both microRNA array profiling, further described below, and mRNA expression studies.

As set forth in Table 5 below, cell lines were selected for diversity, deriving from various squamous cervical cancers (SCC) and adenocarcinomas (AC) and, in most cases, chronically infected with HPV. Cell line C-33A appears to be HPV negative, but likely originally contained HPV. In order to identify early molecular markers that indicate a high progression rate from cervical dysplasia to cancer, seven of the eight cell lines chosen were derived from primary lesions. One cell line, ME-180, was derived from a metastatic source. All cell lines were purchased from LGC Promochem (ATCC) and cultured according to ATCC's guidelines.

TABLE 5

| Cell line | ATCC accession no. | Cancer type | HPV-type |
|---|---|---|---|
| C4-I | CRL-1594 | carcinoma | HPV18 |
| C4-II | CRL-1595 | carcinoma | HPV18 |
| HELA S3 | CCL-2.2 | adenocarcinoma | HPV18 |
| Ca Ski | CRL-1550 | epidermoid carcinoma | HPV16 |
| SIHA | HTB-35 | squamous cell carcinoma | HPV16 |
| SW756 | CRL-10302 | squamous cell carcinoma | HPV18 |
| C-33A | HTB-31 | carcinoma | HPV negative |
| ME-180 | HTB-33 | epidermoid carcinoma metastatic site: omentum | HPV 68 |

All cell lines except for HeLa S3 grew normally. Growth of HeLa S3 was very slow in the beginning of culturing, taking about two weeks before the first passage was done.

Total RNA Preparation and Analysis

Cells from two confluent 75 cm$^2$ flasks were harvested (totaling approximately 10$^7$ cells). Total RNA was prepared using TRIzol® (Invitrogen™) according to the manufacturer's protocol. All RNA samples were diluted in RNase-free water and stored in −80° C. (−112° F.). OD260/280 was measured on a spectrophotometer.

The quantity of RNA obtained is set forth in Table 6, below.

TABLE 6

| | [μg/ml] | Volume μl | Total μg | Ratio 28S/18S |
|---|---|---|---|---|
| CaSki (CRL-1550) | 1000 | 300 | 300 | 1.8 |
| sw756 (CRL-10302) | 2716 | 150 | 407.4 | 1.5 |
| C33A (HTB-31) | 2236 | 150 | 335.4 | 1.6 |
| ME-180 (HTB-33) | 1628 | 150 | 244.2 | 1.6 |
| SiHa (HTB-35) | 1508 | 150 | 226.2 | 1.4 |
| C4-I (CRL-1594) | 1452 | 150 | 217.8 | 1.7 |
| C4-II (CRL-1595) | 1656 | 150 | 248.4 | 1.4 |
| HeLa S3 (CCL-2.2) | 3954 | 150 | 593.1 | 1.6 |

Figure 2:
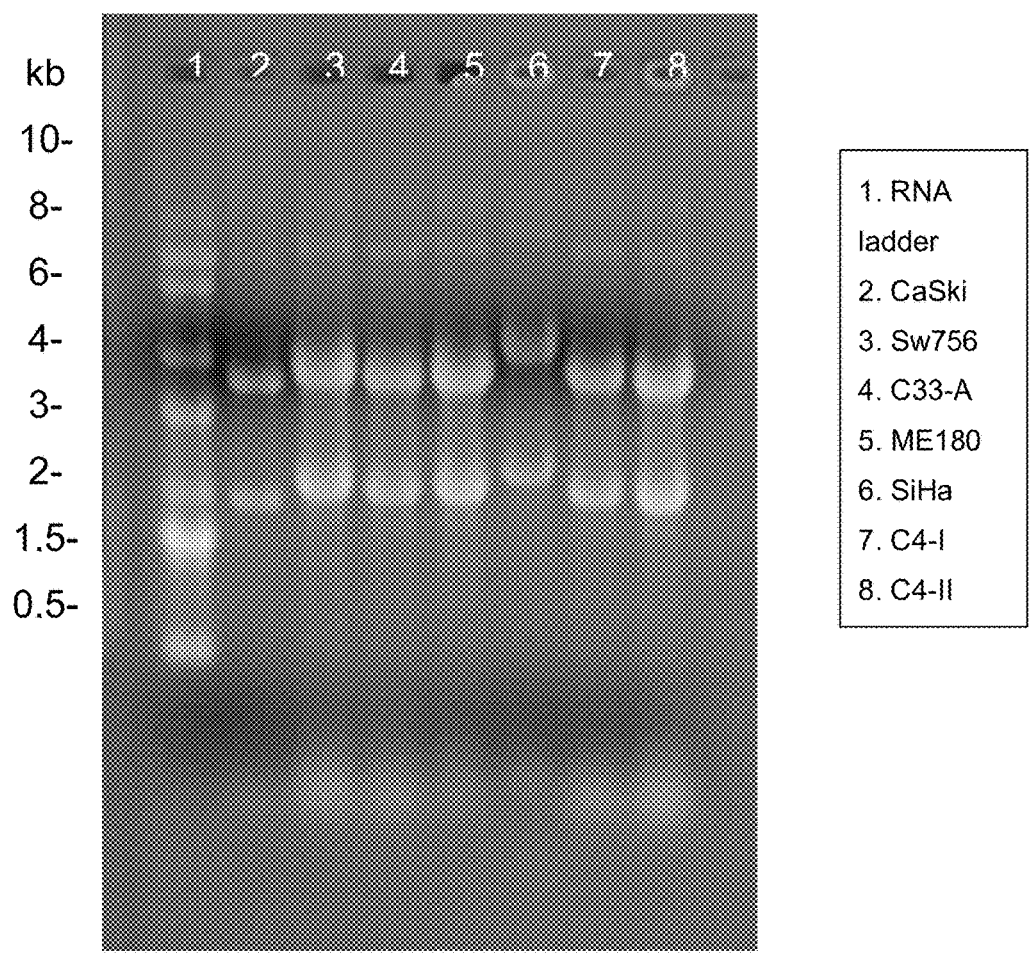

RNA quality was assessed by calculating OD 260/280 ratios, and by electrophoresis on agarose gels under denaturing conditions. The quality of all RNA samples was high as assessed using an Agilent Bioanalyser 2100, as exemplified by the electropherogram shown in FIG. 1 obtained for total RNA from cell line CaSki. FIG. 2 shows denaturing gel electrophoresis of total RNA from the cell lines. The quantity was sufficient for microRNA array profiling and quantitative RT-PCR of both microRNA and mRNA.

Total RNA from normal cervix was purchased for use as a control from Ambion (Applied Biosystems).

MicroRNA Enrichment

MicroRNA enrichment was performed using a Flash PAGE Fractionator (Ambion). The gel purification protocol enriches for small RNAs less than about 40 nucleotides (nt) long, including microRNAs. Briefly, a total RNA sample (prepared as above) was loaded onto a pre-cast gel using the Flash PAGE Fractionator. The total RNA fraction smaller than 40 nt (the "microRNA fraction") was recovered after gel migration and resuspended into nuclease free water.

Microarray Analysis

Probe Design and Spotting

The polynucleotide probes used for microarray preparation had the configuration 5'-NH$_2$—(C)$_6$-(spacer)-(oligomer probe sequence)-3'. The 5'-amino group allowed chemical bonding onto the array support. Each also included an identical spacer sequence of 15 nt, as shown below, to prevent non-specific interactions of the polynucleotide probes with the array support:

```
                                           (SEQ ID NO: 90)
5'AminoC6-TTGTAATACGACTCA - Oligo probe sequence.
```

Probe sequences given in Table 1 omit the linker.

The probes were synthesized according to standard protocols by Eurofins MWG Operon (Ebersberg, Germany). Nexterion (Schott) microarray glass slides were used as the solid support for the microarray.

The polynucleotide probe concentration used for the spotting was 25 μmol. The probes were spotted in duplicate using the Nexterion spotting buffer provided with the array glass support by Schott with 1% SDS (sodium dodecyl sulfate) added to allow larger spot sizes (e.g., 100-150 microns compared to 70-100 microns without SDS). The spotter used was the QArray mini (Genetix) equipped with Stealth SMP3 pins (Telechem). After deposition of one series of spots, the spotting needle was washed 5 times with 60 mM NaOH before spotting the next series of probes. Each slide is designed with 32 blocks of spotted probes, with each block being a 20×20 square of spotted probes. Each probe was spotted in duplicate. Spotted glass slides were stored at 4° C. until use.

MicroRNA Labelling

The labelling of the microRNA fraction was adapted from a published protocol developed at EMBL (Heidelberg, Germany) by the European Molecular Biology Group (Castoldi et al., "A sensitive array for microRNA expression profiling (miChip) based on locked nucleic acids (LNA)," RNA 2006 May; 12(5):913-20. Epub 2006 Mar. 15, incorporated herein by reference in its entirety). Briefly, the microRNA fraction was incubated for 6 hours at 4° C. with a mixture containing 10 μM of dye-labelled tetra-nucleotide (5'-rUrUrUrU-Cy5-3') (or alternatively, 5'-rUrUrUrU-Cy3-3') (Biospring, Germany) in Ambion buffer diluted to 1× with RNase free water, 8% polyethylene glycol (PEG), 2 mM adenosine triphosphate (ATP), and T4 RNA ligase (0.7 U/μl). The labelling reaction was run by heating the mixture for 15 minutes at 65° C. This procedure ligated the poly-U dye-labelled tail to the 3' end of all the microRNAs. Labelled samples were stored at 4° C. before hybridization.

Array Hybridization

The labelled microRNA fraction was hybridized to the spotted arrays using a Discovery hybridization station (Ventana, Tucson, Ariz.). Briefly, 2 mL of a mixture of 1% BSA, 2×SSC, and 0.2% SDS was incubated with the chips for 30 min at 42° C. Then the chips were washed once using EZ Prep buffer (Ventana) and then three more times with Ribowash (Ventana). Next, 20 μl of the labelled microRNA mixture and 180 μl of ChipHybe Reagent (Ventana) were added to the array. The arrays were heated for 6 minutes at 37° C., then were incubated at 42° C. for 8 hours, after which the heating was stopped. The chips were washed once with Ribowash (Ventana) and then heated for 2 minutes at 37° C. The chips were washed again with Ribowash (Ventana) with one drop of CheapClean (Ventana) added, and incubated for 2 minutes at 37° C. The chips were washed two more times using Ribowash (Ventana). The chips were then stored dry at room temperature overnight. On the following day, the final washes were done according to Ventana's instructions for the Discovery hybridization station. The slides were washed twice with 2×SSC+0.2×SDS buffer and then one more time with 0.1×SSC. All the slides were dried using a speed centrifuge from Arrayit (TeleChem International, Sunnyvale, Calif.) at room temperature and kept in the dark before scanning.

As an alternative to the ChipHybe Reagent solution (solution 1), the following solution may be used for array hybridization (solution 2) to form probe:target RNA hybrids by mixing 2 parts of 1.5×TMAC Hybridization Solution to 1 part (v:v) sample, so that the final component concentrations are 3M TMAC, 0.10% Sarkosyl, 50 mM Tris, and 4 mM EDTA, and incubating on the array at 42° C. for 8 h:

| 1.5X TMAC Hybridization Solution | | | |
|---|---|---|---|
| Reagent | Catalog Number | Final Conc | Amount/ 250 mL |
| 5M TMAC* | Sigma T3411 | 4.5M | 225 mL |
| 20% Sarkosyl | — | 0.15% | 1.88 mL |
| 1M Tris-HCl, pH 8.0 | Sigma T3038 | 75 mM | 18.75 mL |
| 0.5M EDTA, pH 8.0 | Invitrogen 15575-020 | 6 mM | 3.0 mL |
| H$_2$O | — | — | 1.37 mL |

*TMAC is tetramethyl ammonium chloride

Array Image Acquisition

The arrays were scanned using an Axon™ scanner (Molecular Devices, Sunnyvale, Calif.) and their Genepix™ software. The image was formatted in tif format, defined by an image color depth of 16 bits/pixel (1600*1600). At such setting, pixels can assume intensity values ranging from 0 to 65,535. Pixels exhibiting the maximum intensity value are "saturated" and were assigned the value of 65,535. The resolution of the array scan was set at 10 μm/pixel. For hybridization experiments using different fluorescent dyes (e.g., Cy5 and Cy3) the photomultiplier tube (PMT) was adjusted to the higher intensity spot (Cy3 is scanned at lower PMT settings than Cy5).

Array Image Analysis

The PMT of the laser scanner digitized the captured fluorescence intensity for each given "point" of a slide and stored the numerical value as a pixel corresponding to that point. A picture composed of such pixels was then analyzed.

The first task for image analysis was to detect the spot position, using a process called segmentation. Spots were segmented by circles of adaptable or fixed radius. To be reliably segmented and quantified, the spot diameter was required to be more than 5-6 pixels. Before segmentation an indexing grid was provided giving the approximate positions of the spots. The segmentation itself detected the limits of spots near the grid circles. Briefly, the Genepix software assigns a circle to each spot on the array (segmentation). The segmentation had to be conducted in a somewhat flexible way due to spotting imperfections and/or support deformation, as the spots were almost never on a perfectly rectangular grid.

After segmentation by the software, the circles were modified manually and adjusted onto the spots until all the spots on the array were clearly identified. At this stage, if the array presented high background noise preventing real spots from being distinguished from the background, the array was rejected for further analysis.

The second task of image analysis was to quantify spots and export the data into a result file. This was a relatively easy and well-defined task once the spots were located on the image. The statistical approach used most frequently to quantify spot intensity was the mean or median of pixels belonging to a spot. The median approach was more robust than the mean value in the presence of outlier pixels. In practice, however, there was little difference in the results obtained using mean or median.

Array Data Analysis

All the array data were analysed using the R bioconductor package ("Bioconductor: open software development for computational biology and bioinformatics," *Genome Biol.* 2004; 5(10):R80. Epub 2004 Sep. 15, which is incorporated herein by reference in its entirety).

Array data were first tested for quality by comparing the spot intensities for the internal controls. One internal control (SEQ ID NO: 83; Table 7) was used as a labelling control (this synthetic RNA is added to the purified microRNA fraction before labelling), and 7 other internal controls (SEQ ID NOs: 84-89 and 405; Table 7) were used for the normalization of the data (these synthetic RNA controls are added to the total RNA fraction before hybridization at 520 fmol each/array). The probe sequences that bind to the synthetic RNAs, and certain mutant probe sequences, are also shown in Table 7 (SEQ ID NOs: 406 to 409 and 212 to 217).

TABLE 7

| Control Sequences used in microarray experiments | |
|---|---|
| Sequence (5'-3') | Sequence identification number |
| CGCGCGUCGCUUUAUCUACUGU | SEQ ID NO: 83; CTL30_COMP |
| UUAUCGUUCGAUAAGUCGCGUU | SEQ ID NO: 84; CTL11_COMP |
| GAAGUUACUAUGUAGGCAACCU | SEQ ID NO: 85; CTL23_COMP |
| CGCGGGACUAAUUGUUACCGGG | SEQ ID NO: 86; CTL26_COMP |
| UCGCGUCGAACUCCGCAACCGA | SEQ ID NO: 87; CTL29_COMP |
| ACCGAACGCCGUACCCAUCGGG | SEQ ID NO: 88; CTL31_COMP |
| CGAGGGUAACGACUCUCGUGUC | SEQ ID NO: 89; CTL36_COMP |
| GCGUACCGACGCGUAGACGGAC | SEQ ID NO: 405; CTL13_COMP |
| TTGTAATACGACTCAACAGTAGATAAAGCGACGCGCG | SEQ ID NO: 406; CTL30 |
| TTGTAATACGACTCAAACGCGACTTATCGAACGATAA | SEQ ID NO: 407; CTL11 |

TABLE 7-continued

Control Sequences used in microarray experiments

| Sequence (5'-3') | Sequence identification number |
|---|---|
| TTGTAATACGACTCAAGGTTGCCTACATAGTAACTTC | SEQ ID NO: 408; CTL23 |
| TTGTAATACGACTCACCCGGTAACAATTAGTCCCGCG | SEQ ID NO: 409; CTL26 |
| TTGTAATACGACTCATCGGTTGCGGAGTTCGACGCGA | SEQ ID NO: 212; CTL29 |
| TTGTAATACGACTCACCCGATGGGTACGGCGTTCGGT | SEQ ID NO: 213; CTL31 |
| TTGTAATACGACTCAGACACGAGAGTCGTTACCCTCG | SEQ ID NO: 214; CTL36 |
| TTGTAATACGACTCAGTCCGTCTACGCGTCGGTACGC | SEQ ID NO: 215; CTL13 |
| TTGTAATACGACTCAGGCCGTCTACGCGTCGGTACGC | SEQ ID NO: 216; CTL13_MUT |
| TTGTAATACGACTCACCCGGTAACAATTAGACCCGCG | SEQ ID NO: 217; CTL26_MUT |

All sequences for which the intensity of the spot was higher than the mean local background intensity plus 1.5 times its standard deviation were categorized as expressed microRNAs. The following criteria were required to be met:
1. Specificity of the hybridization controls had to be within acceptance criteria (e.g. CTL26) vs. its corresponding single base mutant, CTL26_MUT, or CTL13 vs. its corresponding single base mutant, CTL13_mut).
2. Approximate equality of the signal intensity of the replicates of the positive controls
3. Approximate equality between median block signal intensities based on the positive controls for each block
4. Approximate equality between median array signals based on all sequences detected
5. Signal intensity for the purification and labelling control (CTL30).

Statistical normalization of the data was done by computing the Log 2ratio where the Log 2ratio equals average intensity signal of the duplicated spots/median intensity of all positives controls for the block. The normalization was done per block to avoid non-homogenous labelling of all blocks of the array. This block-by-block normalization has been shown to be more efficient then using overall normalization of the slide. The obtained values are Log 2 values.

The intensities of the spots for each polynucleotide probe were compared in the sample from the cervical cancer cell line versus normal cervical tissue, resulting in an evaluation of the relative expression for each microRNA.

The expression fold-change corresponds to 2(Log 2ratio). The Log 2ratio is the ratio between the two conditions compared, or log 2(Xcell-line/Xnormal), which is the same as (log 2Xcell-line–log 2Xnormal), where X is the measured intensity value. In cases where there was no signal from the "normal" condition, the lowest measured intensity value in the experiment was used as the baseline from which a fold-change expression value was calculated. A fold-change value of less than zero corresponds to a down-regulation of (1/fold-change) times.

Data are tabulated in Table 1, and include all microRNAs overexpressed in more than 50% of tested cell lines. Expression in HeLa was not used to qualify microRNAs for inclusion in Table 1, because of an observed odd expression and signal pattern.

5.2 Example 2: Analysis of microRNA on Luminex Platform

The Luminex technology (Luminex Corp., Austin, Tex.) is based on liquid phase hybridization to probe-labelled beads, followed by flow cytometry detection of beads with differing ratios of fluorescent dyes. Beads with up to 100 different dye ratios are available, making it possible to interrogate a single sample for up to 100 analytes simultaneously.

Coupling of Probes to Luminex Beads

Aliquots of each 5'-amino-modified probe having sequences as set forth in Example 1 and Table 1 are prepared at a concentration of 0.1 nmol/μL in molecular biology grade water. The probes are coupled to the beads using carbodiimide chemistry according to the manufacturer's protocol (Luminex bead coupling protocol). The probe-coupled beads are stored at 4° C.

Total RNA Preparation for Luminex Analysis

Fifty fmoles of each of 7 internal controls (the same synthetic RNAs used for the array controls) are added to the total RNA fraction isolated from the biological samples. Prior to hybridization with Luminex beads, the total RNA preparation is treated to avoid the formation of dendrimers, which result from the circularization of a single RNA molecule, or concatenation to another RNA molecule. To avoid the formation of dendrimers, the RNA is pre-treated with calf intestinal phosphatase (CIP) to remove the 5'-phosphate groups. The CIP reagent can be obtained from Invitrogen (Carlsbad, Calif.) and the CIP reaction is run according to the manufacturer's protocol.

Bead Labelling and Hybridization

After CIP treatment, the total RNA fraction is then labelled with biotin using the Vantage microRNA Labelling Kit (Marligen). The labelled fraction is hybridized to the Luminex beads using the Marligen protocol. Briefly, the polynucleotide beads are mixed with the Marligen hybridization solution (1.5×TMAC) and the labelled total RNA. The hybridization is performed at 60° C. for an hour in the dark. After hybridization, the beads are washed using the Luminex standard 6×SSPET wash buffer (sodium phosphate, sodium chloride, EDTA, Triton X-100, pH 7.4).

Detection of Bead Hybridization

The detection of the Luminex beads is done using streptavidin phycoerythrin (SAPE) (Europa Bioproducts, Cambridge, UK). The SAPE is added to the washed beads according to the Luminex protocol. The beads are then read using the Luminex IS-200 instrument using the high gain setting for better resolution.

Data Acquisition and Analysis

The Luminex IS-200 reads at least 25 beads of each dye-ratio in the reaction mix. Each dye-ratio bead corresponds to a particular probe sequence, and the intensity value is returned as an average value of all read beads. The mean fluorescence intensity (MFI) data is normalized using synthetic RNA controls, and fold changes between normal and diseased samples are computed using the Bioplex software (Bio-Rad, Hercules, Calif.) and the R bioconductor package (Bioconductor: open software development for computational biology and bioinformatics, *Genome Biol.* 2004; 5(10):R80. Epub 2004 Sep. 15).

5.3 Example 3: MicroRNAs from Clinical Cervix Samples

Tissue Samples

Archived formalin-fixed, paraffin-embedded (FFPE) blocks from cervical tumors were cut into 10 to 20 μm sections. Three to four sections per sample were extracted using RecoverAll™ Total Nucleic Acid Isolation Kit (Applied Biosystems, Inc.; Foster City, Calif.) according to the manufacturer's protocol. RNA samples were diluted in RNase-free water and stored in −80° C. (−112° F.).

Archived or freshly snap-frozen specimens from cervical tumors were also used. Tissue samples were homogenized by mortar and pestle in TRIzol® Reagent (Invitrogen; Carlsbad, Calif.) and RNA was extracted according to manufacturer's protocol. RNA samples were diluted in RNase-free water and stored in −80° C. (−112° F.).

The cervical samples used in this experiment are shown in Table 8:

TABLE 8

Clinical samples

| Sample name | Sample type | Description |
|---|---|---|
| ASCC-1a | FFPE | AdenoSquamous Cervical Carcinoma (ASCC) |
| SCC-1a | FFPE | Squamous Cervical Carcinoma (SCC) |
| SCC-2 | FFPE | SCC |
| ADC-1a | FFPE | AdenoCarcinoma (ADC) |
| SCC-3a | FFPE | SCC |
| SCC-1b | FFPE | SCC |
| SCC-3b | Frozen | SCC |
| ADC-1b | Frozen | ADC |
| SCC-5 | Frozen | SCC |
| ASCC-1b | Frozen | ASCC |
| SCC-7 | Frozen | SCC |
| SCC-8 | Frozen | SCC |
| cx-normal-4 | Frozen | |
| cx-normal-7 | Frozen | |
| cx-normal-11 | Frozen | |

MicroRNA Preparation:

All samples were enriched for the microRNA fraction using a Flash PAGE Fractionator (Ambion). Briefly, a total RNA sample was loaded onto a pre-cast gel using the Flash PAGE Fractionator. The total RNA fraction smaller than 40 nt (the "microRNA fraction") was recovered after gel migration and resuspended into nuclease free water.

Microarray Analysis

Probe Design and Spotting

The polynucleotide probes used for microarray preparation had the configuration 5'-NH$_2$—(C)$_6$-(spacer)-(oligomer probe sequence)-3'. The 5'-amino group allowed chemical bonding onto the array support. Each also included an identical spacer sequence of 15 nt, as shown below, to prevent non-specific interactions of the polynucleotide probes with the array support:

(SEQ ID NO: 90)
5'AminoC6-TTGTAATACGACTCA - Oligo probe sequence.

Probe sequences given in Table 11 omit the linker.

The probes were synthesized according to standard protocols by Eurofins MWG Operon (Ebersberg, Germany). Nexterion (Schott) microarray glass slides were used as the solid support for the microarray.

The polynucleotide probe concentration used for the spotting was 25 μmol. The probes were spotted in duplicate using the Nexterion spotting buffer provided with the array glass support by Schott with 1% SDS (sodium dodecyl sulfate) added to allow larger spot sizes (e.g., 100-150 microns compared to 70-100 microns without SDS). The spotter used was the QArray mini (Genetix) equipped with Stealth SMP3 pins (Telechem). After deposition of one series of spots, the spotting needle was washed 5 times with 60 mM NaOH before spotting the next series of probes. Each slide is designed with 48 blocks of spotted probes, with each block being a 20×18 square of spotted probes. Each probe was spotted in duplicate. Spotted glass slides were stored at 4° C. until use.

MicroRNA Labelling

The labelling of the microRNA fraction was adapted from a published protocol developed at EMBL (Heidelberg, Germany) by the European Molecular Biology Group (Castoldi et al., "A sensitive array for microRNA expression profiling (miChip) based on locked nucleic acids (LNA)," RNA 2006 May; 12(5):913-20. Epub 2006 Mar. 15, incorporated herein by reference in its entirety). Briefly, the microRNA fraction was incubated for 6 hours at 4° C. with a mixture containing 10 μM of dye-labelled tetra-nucleotide (5'-rUrUrUrU-Cy5-3') (or alternatively, 5'-rUrUrUrU-Cy3-3') (Biospring, Germany) in Ambion buffer diluted to 1× with RNase free water, 8% polyethylene glycol (PEG), 2 mM adenosine triphosphate (ATP), and T4 RNA ligase (0.7 U/μl). The labelling reaction was run by heating the mixture for 15 minutes at 65° C. This procedure ligated the poly-U dye-labelled tail to the 3' end of all the microRNAs. Labelled samples were stored at 4° C. before hybridization.

Array Hybridization

The labelled microRNA fraction was hybridized to the spotted arrays using a Discovery hybridization station (Ventana, Tucson, Ariz.). Briefly, 2 mL of a mixture of 1% BSA, 2×SSC, and 0.2% SDS was incubated with the chips for 30 min at 42° C. Then the chips were washed once using EZ Prep buffer (Ventana) and then three more times with Ribowash (Ventana). Next, 20 μl of the labelled microRNA mixture and 180 μl of ChipHybe Reagent (Ventana) were added to the array. The arrays were heated for 6 minutes at 37° C., then were incubated at 42° C. for 8 hours, after which the heating was stopped. The chips were washed once with Ribowash (Ventana) and then heated for 2 minutes at 37° C. The chips were washed again with Ribowash (Ventana) with one drop of CheapClean (Ventana) added, and incubated for 2 minutes at 37° C. The chips were washed two more times using Ribowash (Ventana). On the following day, the final washes were done according to Ventana's instructions for the Discovery hybridization station. The slides were washed twice with 2×SSC+0.2×SDS buffer and then one more time with 0.1×SSC. All the slides were dried using a speed centrifuge from Arrayit (TeleChem International, Sunnyvale, Calif.) at room temperature and kept in the dark before scanning.

Array Image Acquisition

The arrays were scanned using an Axon™ scanner (Molecular Devices, Sunnyvale, Calif.) and their Genepix™ software. The image was formatted in tif format, defined by an image color depth of 16 bits/pixel (1600*1600). At such setting, pixels can assume intensity values ranging from 0 to 65,535. Pixels exhibiting the maximum intensity value are "saturated" and were assigned the value of 65,535. The resolution of the array scan was set at 10 μm/pixel. For hybridization experiments using different fluorescent dyes (e.g., Cy5 and Cy3) the photomultiplier tube (PMT) was adjusted to the higher intensity spot (Cy3 is scanned at lower PMT settings than Cy5).

Array Image Analysis

The PMT of the laser scanner digitized the captured fluorescence intensity for each given "point" of a slide and stored the numerical value as a pixel corresponding to that point. A picture composed of such pixels was then analyzed. The first task for image analysis was to detect the spot position, using a process called segmentation. Spots were segmented by circles of adaptable or fixed radius. To be reliably segmented and quantified, the spot diameter was required to be more than 5-6 pixels. Before segmentation an indexing grid was provided giving the approximate positions of the spots. The segmentation itself detected the limits of spots near the grid circles. Briefly, the Genepix software assigns a circle to each spot on the array (segmentation). The segmentation had to be conducted in a somewhat flexible way due to spotting imperfections and/or support deformation, as the spots were almost never on a perfectly rectangular grid.

After segmentation by the software, the circles were modified manually and adjusted onto the spots until all the spots on the array were clearly identified. At this stage, if the array presented high background noise preventing real spots from being distinguished from the background, the array was rejected for further analysis.

The second task of image analysis was to quantify spots and export the data into a result file. This was a relatively easy and well-defined task once the spots were located on the image. The statistical approach used most frequently to quantify spot intensity was the mean or median of pixels belonging to a spot. The median approach was more robust than the mean value in the presence of outlier pixels. In practice, however, there was little difference in the results obtained using mean or median.

Array Data Analysis

All the array data were analysed using the R bioconductor package ("Bioconductor: open software development for computational biology and bioinformatics," *Genome Biol.* 2004; 5(10):R80. Epub 2004 Sep. 15, which is incorporated herein by reference in its entirety).

Array data were first tested for quality by comparing the spot intensities for the internal controls. One internal control (SEQ ID NO: 83; Table 9) was used as a labelling control (this synthetic RNA is added to the purified microRNA fraction before labelling), and 6 other internal controls (SEQ ID NOs: 84-89; Table 9) were used for the normalization of the data (these synthetic RNA controls are added to the total RNA fraction before hybridization at 520 fmol each/array). The probe sequences that bind to the synthetic RNAs, and a mutant probe sequence, are also shown in Table 9 (SEQ ID NOs: 406 to 409, 212 to 214, and 217).

TABLE 9

Control Sequences used in microarray experiments

| Sequence (5'-3') | Sequence identification number |
| --- | --- |
| CGCGCGUCGCUUUAUCUACUGU | SEQ ID NO: 83; CTL30_COMP |
| UUAUCGUUCGAUAAGUCGCGUU | SEQ ID NO: 84; CTL11_COMP |
| GAAGUUACUAUGUAGGCAACCU | SEQ ID NO: 85; CTL23_COMP |
| CGCGGGACUAAUUGUUACCGGG | SEQ ID NO: 86; CTL26_COMP |
| UCGCGUCGAACUCCGCAACCGA | SEQ ID NO: 87; CTL29_COMP |
| ACCGAACGCCGUACCCAUCGGG | SEQ ID NO: 88; CTL31_COMP |
| CGAGGGUAACGACUCUCGUGUC | SEQ ID NO: 89; CTL36_COMP |
| TTGTAATACGACTCAACAGTAGATAAAGCGACGCGCG | SEQ ID NO: 406; CTL30 |
| TTGTAATACGACTCAAACGCGACTTATCGAACGATAA | SEQ ID NO: 407; CTL11 |
| TTGTAATACGACTCAAGGTTGCCTACATAGTAACTTC | SEQ ID NO: 408; CTL23 |
| TTGTAATACGACTCACCCGGTAACAATTAGTCCCGCG | SEQ ID NO: 409; CTL26 |
| TTGTAATACGACTCATCGGTTGCGGAGTTCGACGCGA | SEQ ID NO: 212; CTL29 |
| TTGTAATACGACTCACCCGATGGGTACGGCGTTCGGT | SEQ ID NO: 213; CTL31 |
| TTGTAATACGACTCAGACACGAGAGTCGTTACCCTCG | SEQ ID NO: 214; CTL36 |
| TTGTAATACGACTCACCCGGTAACAATTAGACCCGCG | SEQ ID NO: 217; CTL26_MUT |

All sequences for which the intensity of the spot was higher than the mean local background intensity plus 1.5 times its standard deviation were categorized as expressed microRNAs. The following criteria were required to be met in order consider the array intensity data valid for further analysis:

1. Specificity of the hybridization controls had to be within acceptance criteria (e.g. CTL26 vs. its corresponding single base mutant, CTL26_MUT).
2. Approximate equality of the signal intensity of the replicates of the positive controls
3. Approximate equality between median block signal intensities based on the positive controls for each block
4. Approximate equality between median array signals based on all sequences detected
5. Signal intensity for the purification and labelling control (CTL30).

Statistical normalization of the data was done by computing the Log 2ratio where the Log 2ratio equals average intensity signal of the duplicated spots/median intensity of all positives controls for the block. The normalization was done per block to avoid non-homogenous labelling of all blocks of the array. This block-by-block normalization has been shown to be more efficient then using overall normalization of the slide. The obtained values are Log 2 values.

The intensities of the spots for each polynucleotide probe were compared in the sample from the cervical cancer cell line versus normal cervical tissue, resulting in an evaluation of the relative expression for each microRNA.

The expression fold-change corresponds to $2^{(Log\ 2ratio)}$. The Log 2ratio is the ratio between the two conditions compared, or log 2(Xcell-line/Xnormal), which is the same as (log 2Xcell-line–log 2Xnormal), where X is the measured intensity value. In cases where there was no signal from the "normal" condition, the lowest measured intensity value in the experiment was used as the baseline from which a fold-change expression value was calculated. A fold-change value of less than zero corresponds to a down-regulation of (1/fold-change) times.

Results

All of the samples generated low signals, possibly due to degradation of the samples. For three of the normal samples (normal–4, –7, and –11), a reliable number of sequences were detected, so those samples were used as controls for the analysis.

In this experiment, miR-21 was up-regulated in all of the tumors tested compared to the normal samples. In certain tumor samples (for example, ADC-1a, ADC-1b, ASCC-1b, SCC-4a, and SCC-7), a particularly high or low number of sequences was detected. Two microRNAs, miR-145 and miR-143, which have previously been reported to be down-regulated in certain cancer tissues (Wang et al., *PLoS One* (2008) 3: e2557), were also found to be downregulated in this experiment. Table 10 shows a list of the microRNAs that were found to be upregulated in at least one of the tumor samples tested. Table 11 shows the probe sequences that were used to detect the microRNAs listed in Table 10. Table 12 shows the microRNA precursor sequences and their chromosomal location.

TABLE 10

| | Fold-change in expression relative to normal controls | | | | | | | | | | | |
|---|---|---|---|---|---|---|---|---|---|---|---|---|
| Sequence | SCC1a | SCC1b | SCC2 | SCC3a | SCC3b | SCC5 | SCC7 | SCC8 | ADC1a | ADC1b | ASCC1a | ASCC1b |
| 10030-R5-1 | 0.48 | 0.62996 | 0.42 | 0.68 | 0.45 | 5.13 | 1.09 | 0.83 | 0.48 | 6.55 | 0.34 | 7.08 |
| 10435-R4-1 | 0.55 | 0.62996 | 0.42 | 0.68 | 0.45 | 4.01 | 0.59 | 0.83 | 0.48 | NA | 0.37 | 4.24 |
| 12730-R5-2 | 0.30 | 0.56850 | 0.38 | 0.89 | 0.40 | 0.69 | 0.76 | 0.75 | 0.43 | NA | 0.30 | 3.09 |
| 12917-R5-1 | 0.29 | 0.54270 | 0.36 | 0.58 | 0.38 | 0.47 | 2.93 | 0.72 | 0.41 | NA | 0.29 | 0.51 |
| 12917-R5-2 | 0.29 | 0.53431 | 0.35 | 0.57 | 0.38 | 0.47 | 2.79 | 0.71 | 0.40 | NA | 0.29 | 0.50 |
| 13075-L5-1 | 0.34 | 0.62996 | 0.42 | 1.17 | 0.45 | 0.55 | 1.71 | 0.83 | 0.48 | NA | 0.34 | 0.94 |
| 13108-L5-2 | 1.23 | 1.34983 | 0.87 | 0.68 | 0.60 | 10.57 | 0.81 | 0.83 | 0.48 | 11.37 | 0.34 | 16.00 |
| 13111-L5-3 | 1.50 | 1.52386 | 0.79 | 1.69 | 0.99 | 1.30 | 3.85 | 0.85 | 0.58 | NA | 0.55 | 1.26 |
| 13122-L5-1 | 1.79 | 1.68168 | 0.69 | 0.68 | 0.54 | 2.80 | 1.68 | 0.83 | 0.48 | 4.43 | 0.34 | 3.47 |
| 13124-L5-2 | 0.48 | 0.43358 | 0.40 | 0.82 | 0.23 | 0.62 | 1.22 | 0.43 | 0.25 | NA | 0.18 | 6.48 |
| 13129-L5-3 | 0.80 | 0.72991 | 0.77 | 0.82 | 0.40 | 1.14 | 4.07 | 0.25 | 0.34 | NA | 0.10 | 42.27 |
| 13168-L5-1 | 0.92 | 2.67482 | 1.46 | 1.65 | 1.02 | 2.21 | 0.59 | 0.83 | 0.48 | NA | 6.61 | 0.59 |
| 13181-L5-2 | 0.61 | 0.50095 | 0.33 | 0.54 | 0.35 | 1.04 | 1.13 | 0.66 | 0.38 | NA | 0.27 | 48.83 |
| 13195-L5-1 | 0.40 | 1.75224 | 0.42 | 0.68 | 0.45 | 0.55 | 0.59 | 0.83 | 0.48 | 5.52 | 0.52 | 0.59 |
| 13207-R5-4 | 1.50 | 1.36744 | 1.01 | 0.68 | 0.45 | 2.13 | 2.09 | 0.83 | 0.48 | NA | 0.34 | 2.06 |
| 13209-L5-2 | 0.47 | 0.39869 | 0.38 | 0.26 | 0.17 | 1.77 | 1.59 | 1.08 | 0.26 | NA | 0.41 | 3.61 |
| 13219-L5-1 | 1.01 | 0.85828 | 0.64 | 0.68 | 0.45 | 1.79 | 1.42 | 0.83 | 0.48 | NA | 0.34 | 2.00 |
| 13227-L5-2 | 0.78 | 0.73130 | 0.47 | 0.78 | 0.47 | 1.30 | 3.21 | 1.02 | 0.31 | NA | 0.22 | 2.28 |
| 13229-R5-3 | 0.68 | 0.81104 | 0.57 | 2.52 | 1.40 | 1.07 | 0.70 | 1.14 | 0.31 | NA | 0.69 | 1.55 |
| 13231-L5-3 | 0.19 | 0.35780 | 0.24 | 0.38 | 0.25 | 0.31 | 1.08 | 0.47 | 0.27 | NA | 0.19 | 5.11 |
| 13247-L5-3 | 0.48 | 0.51572 | 0.20 | 0.92 | 0.62 | 0.83 | 5.13 | 1.41 | 0.27 | NA | 0.41 | 2.28 |
| 13252-L5-3 | 1.77 | 2.03164 | 0.42 | 0.68 | 0.45 | 3.37 | 0.59 | 0.83 | 0.48 | 17.08 | 0.34 | 75.31 |
| 13254-R5-1 | 3.95 | 3.51150 | 0.94 | 0.55 | 0.69 | 16.00 | 0.48 | 1.86 | 0.39 | 26.31 | 0.28 | 9.67 |
| 13260-L5-2 | 0.31 | 0.49907 | 0.33 | 0.53 | 0.35 | 0.43 | 0.47 | 0.66 | 0.38 | NA | 0.27 | 0.47 |
| 13267-L5-1 | 0.66 | 0.51565 | 0.56 | 1.62 | 0.55 | 0.83 | 2.21 | 1.01 | 0.19 | NA | 0.14 | 31.04 |
| 13274-L5-3 | 0.90 | 1.05855 | 0.54 | 0.67 | 0.55 | 1.71 | 3.59 | 0.93 | 0.33 | NA | 0.38 | 2.23 |
| 13283-L5-3 | 0.75 | 0.84669 | 0.39 | 0.58 | 0.38 | 5.35 | 1.84 | 0.72 | 0.41 | 6.57 | 0.29 | 9.44 |
| 13291-L5-1 | 0.49 | 0.58218 | 0.31 | 0.50 | 0.33 | 0.64 | 2.38 | 0.83 | 0.35 | NA | 0.25 | 1.82 |
| 13296-L5-3 | 0.60 | 0.50124 | 0.33 | 0.54 | 0.35 | 1.04 | 1.14 | 0.66 | 0.38 | NA | 0.27 | 11.21 |
| 13312-L5-1 | 0.29 | 0.24998 | 0.26 | 0.92 | 0.30 | 0.36 | 1.29 | 0.23 | 0.13 | NA | 1.25 | 4.81 |
| 13325-R5-2 | 0.56 | 0.70384 | 0.63 | 1.81 | 0.99 | 1.22 | 5.31 | 0.67 | 0.38 | NA | 0.56 | 0.47 |
| 13335-L5-2 | 0.49 | 0.43467 | 0.34 | 0.32 | 0.21 | 0.97 | 1.51 | 0.39 | 0.22 | NA | 0.16 | 3.91 |
| 13335-L5-3 | 0.43 | 0.39498 | 0.30 | 0.59 | 0.44 | 1.00 | 2.18 | 0.89 | 0.17 | NA | 0.24 | 2.14 |
| 13339-L5-1 | 0.68 | 0.62012 | 0.43 | 0.46 | 0.32 | 1.17 | 2.49 | 1.05 | 0.26 | NA | 0.28 | 3.69 |
| 13504-R5-3 | 1.55 | 1.49604 | 1.52 | 0.68 | 0.45 | 1.57 | 0.83 | 0.83 | 0.48 | NA | 0.65 | 0.59 |
| 13532-L5-2 | 1.98 | 2.37574 | 0.73 | 0.64 | 0.42 | 5.40 | 0.56 | 0.88 | 0.46 | 12.41 | 0.32 | 2.08 |
| 227-L5-1 | 0.64 | 0.74093 | 0.56 | 0.81 | 0.51 | 0.96 | 2.97 | 0.95 | 0.32 | NA | 0.54 | 1.31 |
| 25-R5-2 | 0.90 | 1.05584 | 0.29 | 0.47 | 0.31 | 1.62 | 0.78 | 0.58 | 0.33 | 10.98 | 0.23 | 1.40 |

TABLE 10-continued

Fold-change in expression relative to normal controls

| Sequence | SCC1a | SCC1b | SCC2 | SCC3a | SCC3b | SCC5 | SCC7 | SCC8 | ADC1a | ADC1b | ASCC1a | ASCC1b |
|---|---|---|---|---|---|---|---|---|---|---|---|---|
| 2819-L5-2 | 0.34 | 0.62996 | 7.35 | 0.68 | 0.45 | 0.55 | 0.59 | 0.83 | 0.48 | NA | 0.34 | 0.59 |
| 2819-R5-4 | 0.47 | 0.38389 | 0.32 | 0.57 | 0.40 | 0.67 | 1.32 | 0.64 | 0.23 | 0.87 | 0.32 | 1.86 |
| 3371-L4-1 | 0.21 | 0.38626 | 0.25 | 1.04 | 0.45 | 0.52 | 1.00 | 0.51 | 0.29 | NA | 0.21 | 0.91 |
| 3744-R5-1 | 1.33 | 1.09513 | 0.78 | 0.67 | 0.54 | 1.93 | 2.78 | 1.04 | 0.25 | NA | 0.18 | 3.05 |
| 3911-R5-1 | 0.34 | 0.62996 | 0.42 | 2.28 | 0.90 | 0.55 | 0.59 | 0.83 | 0.48 | NA | 0.34 | 1.79 |
| 4417-R5-2 | 1.29 | 2.32318 | 0.96 | 0.68 | 0.45 | 3.07 | 0.59 | 0.83 | 0.48 | NA | 1.14 | 1.56 |
| 4440-L3-2 | 4.04 | 7.35978 | 3.34 | 8.03 | 6.55 | 3.01 | 2.06 | 0.53 | 1.66 | 3.29 | 2.85 | 1.51 |
| 4440-R3-2 | 0.50 | 0.50446 | 0.38 | 0.67 | 0.39 | 3.32 | 1.03 | 0.36 | 0.16 | 2.82 | 0.28 | 4.80 |
| 4498-L3-2 | 0.84 | 0.78263 | 0.50 | 0.68 | 0.45 | 5.48 | 0.91 | 0.83 | 0.48 | 5.05 | 0.46 | 8.39 |
| 4719-R5-1 | 2.00 | 2.68058 | 0.84 | 0.68 | 0.45 | 3.15 | 0.59 | 0.83 | 0.48 | 8.15 | 0.34 | 0.59 |
| 4765-L5-1 | 0.54 | 0.62996 | 0.42 | 3.01 | 1.55 | 1.22 | 0.59 | 0.83 | 0.48 | NA | 0.34 | 2.20 |
| 4829-R2-1 | 0.53 | 0.61657 | 0.43 | 1.12 | 0.62 | 1.73 | 5.34 | 0.87 | 0.25 | NA | 0.56 | 2.07 |
| 4855-R5-1 | 1.84 | 2.01422 | 1.31 | 1.88 | 1.00 | 1.82 | 2.61 | 0.33 | 0.65 | 3.60 | 3.08 | 0.24 |
| 4988-R5-2 | 0.57 | 0.58473 | 0.57 | 0.85 | 0.46 | 0.32 | 1.47 | 0.48 | 0.28 | NA | 2.25 | 0.34 |
| 6216-L1-1 | 3.25 | 5.58042 | 2.97 | 8.16 | 5.47 | 2.04 | 2.31 | 0.67 | 1.39 | NA | 2.38 | 1.62 |
| 6216-R5-2 | 0.57 | 0.55598 | 0.45 | 0.80 | 0.46 | 4.04 | 1.04 | 0.33 | 0.20 | 3.13 | 0.30 | 5.54 |
| 6235-R5-2 | 4.37 | 4.36450 | 1.88 | 0.68 | 1.20 | 6.64 | 2.24 | 0.83 | 0.48 | 7.33 | 0.34 | 8.03 |
| 6803-R5-2 | 0.57 | 0.53791 | 0.39 | 2.83 | 1.52 | 1.31 | 1.27 | 0.57 | 0.33 | NA | 0.33 | 3.89 |
| 7067-L5-1 | 0.44 | 0.62996 | 0.42 | 0.68 | 0.45 | 2.73 | 0.59 | 0.83 | 0.48 | NA | 0.34 | 4.27 |
| 7126-L3-1 | 0.56 | 0.49062 | 0.37 | 0.74 | 0.50 | 0.64 | 2.54 | 1.08 | 0.23 | NA | 0.39 | 1.37 |
| 7182-L5-1 | 0.48 | 0.50155 | 0.43 | 0.82 | 0.51 | 0.78 | 4.34 | 0.82 | 0.18 | NA | 0.32 | 1.29 |
| 7292-R3-2 | 0.37 | 0.63424 | 0.35 | 0.57 | 0.38 | 1.26 | 0.50 | 0.71 | 0.41 | 18.66 | 0.29 | 3.23 |
| 7578-L3-1 | 4.60 | 0.54709 | 1.08 | 0.59 | 0.85 | 0.48 | 0.51 | 1.78 | 0.85 | 39.02 | 0.57 | 7.03 |
| 7781-R5-2 | 0.43 | 0.51223 | 0.34 | 0.55 | 0.36 | 0.84 | 1.58 | 0.68 | 0.39 | NA | 0.27 | 2.40 |
| 7887-L5-3 | 0.47 | 0.48451 | 0.32 | 0.52 | 0.34 | 1.27 | 0.45 | 0.64 | 0.37 | NA | 0.26 | 3.37 |
| 8004-R3-2 | 1.02 | 0.91481 | 0.42 | 0.68 | 0.45 | 1.94 | 1.27 | 0.83 | 0.48 | NA | 0.34 | 1.95 |
| 8298-R5-1 | 0.38 | 0.38316 | 0.34 | 0.50 | 0.34 | 0.63 | 2.32 | 1.05 | 0.29 | NA | 0.30 | 1.85 |
| 8339-R5-1 | 0.70 | 1.10768 | 0.91 | 0.68 | 0.45 | 4.60 | 0.59 | 0.83 | 0.48 | NA | 0.57 | 3.15 |
| 836-R4-1 | 1.33 | 1.43068 | 0.42 | 0.68 | 0.45 | 1.85 | 1.53 | 0.83 | 0.48 | NA | 0.34 | 0.59 |
| 9053-R3-1 | 0.68 | 0.80482 | 0.64 | 0.87 | 0.48 | 3.04 | 1.01 | 0.89 | 0.33 | NA | 0.23 | 4.22 |
| 9164-R5-1 | 0.34 | 0.62996 | 0.42 | 2.42 | 1.14 | 1.06 | 0.72 | 0.83 | 0.48 | NA | 0.34 | 1.09 |
| 9485-R5-1 | 2.15 | 2.24932 | 2.77 | 0.68 | 0.82 | 1.32 | 0.59 | 0.83 | 1.14 | NA | 0.34 | 0.59 |
| 9691-L4-1 | 0.58 | 0.70634 | 0.38 | 0.62 | 0.41 | 0.98 | 2.22 | 0.76 | 0.44 | NA | 0.31 | 1.55 |
| 9816-R5-1 | 0.46 | 0.58377 | 0.39 | 0.63 | 0.41 | 0.51 | 1.55 | 0.82 | 0.44 | NA | 0.31 | 1.76 |
| 999996-L4-1 | 0.25 | 0.46163 | 0.30 | 0.49 | 0.33 | 0.40 | 0.43 | 0.61 | 0.35 | 5.53 | 3.56 | 0.43 |
| miR-1246 | 3.51 | 4.24691 | 1.92 | 0.68 | 1.16 | 5.40 | 2.72 | 0.96 | 0.55 | 5.82 | 0.55 | 7.41 |
| miR-1290 | 1.46 | 1.29141 | 0.77 | 0.68 | 0.45 | 1.94 | 1.74 | 0.83 | 0.48 | NA | 0.34 | 1.84 |
| miR-1308 | 5.41 | 5.16798 | 1.26 | 0.50 | 0.97 | 18.09 | 0.50 | 2.59 | 1.12 | 39.12 | 0.79 | 15.99 |
| miR-142-3p | 0.79 | 0.68772 | 1.20 | 0.68 | 1.44 | 4.46 | 0.59 | 1.37 | 0.48 | NA | 0.55 | 0.97 |
| miR-143 | 0.21 | 0.39339 | 0.26 | 0.42 | 0.28 | 0.42 | 0.37 | 0.52 | 0.30 | 5.20 | 0.60 | 0.37 |
| miR-145 | 0.31 | 0.40117 | 0.43 | 0.43 | 0.28 | 0.48 | 0.37 | 0.53 | 0.65 | 5.99 | 0.81 | 0.60 |
| miR-1826 | 2.93 | 4.04445 | 2.24 | 0.57 | 1.23 | 4.97 | 1.14 | 1.44 | 1.02 | 11.52 | 1.00 | 5.45 |
| miR-195 | 0.37 | 0.41556 | 0.27 | 0.45 | 0.55 | 1.21 | 0.39 | 0.55 | 0.31 | 5.64 | 0.53 | 1.19 |
| miR-200c | 1.00 | 1.22187 | 0.95 | 0.68 | 0.99 | 1.34 | 0.59 | 0.83 | 0.48 | NA | 1.11 | 2.05 |
| miR-205 | 6.23 | 5.69362 | 2.07 | 0.61 | 1.47 | 4.24 | 0.53 | 1.13 | 0.43 | NA | 1.45 | 2.54 |
| miR-21 | 3.01 | 3.70795 | 10.92 | 0.56 | 7.46 | 24.36 | 1.01 | 7.32 | 3.70 | 21.96 | 11.87 | 24.14 |
| miR-31 | 0.34 | 0.62996 | 0.42 | 0.68 | 0.45 | 0.55 | 0.59 | 0.83 | 0.48 | NA | 0.58 | 0.92 |
| miR-451 | 0.65 | 0.52572 | 0.33 | 0.47 | 0.65 | 0.38 | 5.85 | 0.58 | 0.33 | NA | 0.70 | 0.41 |
| miR-483-5p | 0.54 | 0.37151 | 0.25 | 1.24 | 0.26 | 0.32 | 1.72 | 0.49 | 0.28 | NA | 0.20 | 0.35 |
| miR-491-3p | 0.50 | 0.62996 | 0.42 | 0.68 | 0.81 | 12.59 | 0.59 | 0.83 | 0.48 | 58.76 | 0.34 | 18.82 |
| miR-494 | 0.63 | 0.81477 | 0.54 | 0.68 | 0.45 | 1.56 | 0.59 | 0.83 | 0.48 | NA | 0.49 | 2.70 |
| miR-720 | 1.15 | 1.54266 | 1.73 | 1.02 | 0.92 | 1.78 | 0.59 | 0.83 | 0.85 | NA | 1.27 | 1.45 |
| miR-765 | 0.28 | 0.42837 | 0.28 | 0.84 | 0.46 | 0.51 | 1.56 | 0.55 | 0.32 | NA | 0.28 | 0.84 |
| miR-98 | 1.11 | 0.57757 | 0.61 | 0.41 | 1.01 | 1.00 | 0.36 | 0.51 | 0.59 | 7.06 | 1.04 | 2.14 |

TABLE 11

Probe sequences

| probe | probe sequence 5' -> 3' | SEQ ID |
|---|---|---|
| 25-R5-2 | TTCTGCTTTCCCAGAGCCTCACCCCCTCTTTT | 133 |
| 227-L5-1 | ACACCTGTCTCTCCCCAGTGCTTCCGCCCCTCA | 134 |
| 836-R4-1 | AAATAATCATTCCAAATGGTTCTCCCTGCTATGATTCAC | 32 |
| 2819-L5-2 | CCACACTTCTAATTGGACAAAGTGCCTTTCAAACT | 136 |
| 2819-R5-4 | CAGCCTGCCACCGCCGCTTTTGAAAGAAGCACTTCA | 137 |
| 3371-L4-1 | TTTCCTTTCCTCCCCTCCACACCCCATGACTCCCCACACTTGAG | 1 |

TABLE 11-continued

Probe sequences

| probe | probe sequence 5' -> 3' | SEQ ID |
|---|---|---|
| 3744-R5-1 | CTTCTCCTTCCTCCCTGCTCCCCTCCCACTAATGCCAAAT | 138 |
| 3911-R5-1 | GGCTCCCTAGTGAAAAAATGCAAAATTTGTATAAT | 139 |
| 4417-R5-2 | ACTCGGCGCTCATCAAAAAGTTCCCTGTCCG | 141 |
| 4440-L3-2 | TTTGACATTCAGAGCACTGGGCAGAAATCACA | 142 |
| 4440-R3-2 | GTCATAGTTACTCCCGCCGTTTACCCGCATTTC | 143 |
| 4498-L3-2 | GAGATCCAGACGGCCGTGCGCCTGCTGCTGCCT | 144 |
| 4719-R5-1 | ACAGCATCACATGGATTCTGTGTCCAGTGGCCTTAGCA | 145 |
| 4765-L5-1 | ACATGCTCCTGACACTTTCTCTTAGTTTCTCGGGCTCC | 146 |
| 4829-R2-1 | TCCCTTTGTGCTGCCCGAGTGCCTTCCCCCTG | 147 |
| 4855-R5-1 | CGGGTCTCCCGCTTCCCCCTCCTGCTCCAAGG | 148 |
| 4988-R5-2 | CTCCTCCTCCCCGTCTTTGGATACCAAACAC | 149 |
| 6216-L1-1 | GACATTCAGAGCACTGGGCAGAAATCACATG | 151 |
| 6216-R5-2 | CATAGTTACTCCCGCCGTTTACCCGTGCTTC | 152 |
| 6235-R5-2 | TCTGCTCCAAAAATCCATTTAATATATTGT | 153 |
| 6803-R5-2 | GCTCCCTCTCTGGTTGGACCTCACCCAAA | 154 |
| 7067-L5-1 | GGAGATCCAGACGGCCGAGCGCCTGCTGCTGCCC | 155 |
| 7126-L3-1 | GCACACCCGCTCTCCGGCCCGCGCCCCTG | 156 |
| 7182-L5-1 | AACTAGCCGTTTCCGTCACCTTCCCCTGCCCCC | 157 |
| 7292-R3-2 | ACAATATTTATCCAGGGATGGGAGTCAGATGCA | 158 |
| 7578-L3-1 | CGCAGTGCACACCCTGAGCTACAGCCCCTC | 159 |
| 7781-R5-2 | AGCCTGTGCCTGCCGCTGTCTAGTACTGGT | 160 |
| 7887-L5-3 | CAAGAGCCAGCCTGCACTACCAGTCCCATGCCA | 161 |
| 8004-R3-2 | GGAACTGCTTCTCCTTGCTCCAGTCATTGAAG | 162 |
| 8298-R5-1 | GATGCTGGCGTCCGCCGCAGCCTCTCGCCCCATCCCGG | 163 |
| 8339-R5-1 | AAAAGCCAATACATTTTCACTGTACCGGCCAC | 164 |
| 9053-R3-1 | TTCTTGCCCTCCAATCCCCGGGCTCCACCAGCC | 5 |
| 9164-R5-1 | TGCTTCCATCCCGCCAGTTTGGTTTCATTGTACTGACAACC | 166 |
| 9485-R5-1 | CTGGGTGAGGTCCCACCGTGGTGCGCTTGGCTGTGCCAGC | 167 |
| 9691-L4-1 | AATCATCCATTTCATCCGCATCTCCCTCTTGGCCCCTTGC | 7 |
| 9816-R5-1 | CCCTTTAAGAGCCTCTCCGCGCGCTGCCG | 169 |
| 10030-R5-1 | CCGTGGATGTCAACTCAGCTGCCTTCCGCC | 170 |
| 10435-R4-1 | GCATGCTAATTGTGCCCTGTTGTCTTTCTTAAACT | 171 |
| 999996-L4-1 | GGGAGGAGTCAGGTGTGTGCTGTGGGTTGGGGGAAGAC | 173 |
| 12730-R5-2 | GCGCCCTGTGTTGTGCTCCGCTCTCCGGGAAATGC | 174 |
| 12917-R5-1 | GGGCCCTTCCCTTCCCCCAACATTGAGCCTTG | 175 |
| 12917-R5-2 | GGACCTATGGGCCCTTCCCTTCCCCAACATTG | 176 |
| 13075-L5-1 | TGAAAGCTGAAGTCCAGCCCAGCCCTCT | 177 |

TABLE 11-continued

Probe sequences

| probe | probe sequence 5' -> 3' | SEQ ID |
|---|---|---|
| 13108-L5-2 | CTGCTGCCTTCCTTGGTTGAGGGGCCTGAGCACG | 178 |
| 13111-L5-3 | TCTCCGCCGGGCCTTCACCCTGCCCTGCTCTTCT | 179 |
| 13122-L5-1 | TTAGGAAATTCCATCTCACCTGCTCCAGTCC | 180 |
| 13124-L5-2 | GCTCCATGTCTCCTCCCCTCCGCGAAAGCCTAAAC | 181 |
| 13129-L5-3 | AGCCTTCCTGTCCCCTGGCCCCCGACCTGCTCCA | 182 |
| 13168-L5-1 | CGCTTCCTTAACCATTTTTTTTTTTTAACCAC | 183 |
| 13181-L5-2 | TGGACGTCTGAACAGTCACTGCCTGCCCCAACCT | 184 |
| 13195-L5-1 | ATGACCATTTGTATTAGTATCTTTTTTTTTTT | 185 |
| 13207-R5-4 | CTGCGGCAAGTGCTTCTACATCCCTGCTCCAACAA | 186 |
| 13209-L5-2 | TAACTCGCCTGCTGCCCCGGCGGCCTGCCCGCCG | 187 |
| 13219-L5-1 | CTCTGACTCCCTCACTCAGTCTCTCTGCTCCAGC | 188 |
| 13227-L5-2 | GGGCCCAGTCCTCCTCGTCCCCCTTCCCACCTCGG | 189 |
| 13229-R5-3 | GCAGCTCCGCCAGTCTCTGTGGGCAGGGAGAAG | 190 |
| 13231-L5-3 | GGCCCACCCGGGGGCCGCTCCCCAGCACCGACGCC | 191 |
| 13247-L5-3 | TCCTGAGCCGCCTTCCCCTCCCGACCTCAGAGCCCT | 192 |
| 13252-L5-3 | ACGTGCCTTCCTGACTGTGAGCTCCTTGAGAGC | 193 |
| 13254-R5-1 | CAATGAACCACTGAACCACTCATGCACTGAACC | 194 |
| 13260-L5-2 | CTGTAGACCCCACACTCAGTCTCTATAGCTA | 195 |
| 13267-L5-1 | CACTCCCTGCTGGCCCCCACCTCACCTATGGTG | 196 |
| 13274-L5-3 | CCTTCTCTTCTCCCGTGCTCCCACCCTCCCTCAGGG | 197 |
| 13283-L5-3 | GGACCCCTGCCTTCCTTGCTGCCACCCTTTGCACA | 198 |
| 13291-L5-1 | CCCAAGCGCCCCTTCCTCCCTCCTTCCCTCCCG | 199 |
| 13296-L5-3 | CAGTCACCTCAGATTCCTGTGCCCTCTGCCCTGG | 200 |
| 13312-L5-1 | CCACCCCTCCCCCACAGCCCAGCCCCACTCAC | 201 |
| 13325-R5-2 | TCCAACACTGCCTGGCGCTGGGCTCTTCCCCA | 134 |
| 13335-L5-2 | CCACTGCCCTCCTGCCGCATCCTATGCTCCTCT | 140 |
| 13335-L5-3 | ACCTCAGCCTCCACTGCCCTCCTGCCGCATCCTAT | 168 |
| 13339-L5-1 | GACTGAGGGTTTAAAGAAGATGGTGTCCGCCGC | 150 |
| 13504-R5-3 | AGACTGCTGTAAATGCGGACAAAGCGTCCCTGC | 165 |
| 13532-L5-2 | TGCTCTACCGGCTATGACATTAGGTGTGACCG | 172 |
| miR-1246 | CCTGCTCCAAAAATCCATT | 208 |
| miR-1290 | TCCCTGATCCAAAAATCCA | 209 |
| miR-1308 | CCACTGAACCACCCATGC | 210 |
| miR-1826 | ATTGCGTTCGAAGTGTCGATGATCAAT | 211 |
| miR-200c | TCCATCATTACCCGGCAGTATTA | 203 |
| miR-451 | AACTCAGTAATGGTAACGGTTT | 204 |
| miR-483-5p | CTCCCTTCTTTCCTCCCGTCTT | 202 |
| miR-491-3p | GTAGAAGGGAATCTTGCATAAG | 205 |

TABLE 11-continued

Probe sequences

| probe | probe sequence 5' -> 3' | SEQ ID |
|---|---|---|
| miR-494 | GAGGTTTCCCGTGTATGTTTCA | 206 |
| miR-720 | TGGAGGCCCCAGCGAGA | 207 |
| miR-765 | CATCACCTTCCTTCTCCTCCA | 39 |
| miR-143 | GAGCTACAGTGCTTCATCTCA | 218 |
| miR-145 | AGGGATTCCTGGGAAAACTGGAC | 219 |
| miR-205 | CAGACTCCGGTGGAATGAAGGA | 220 |
| miR-21 | TCAACATCAGTCTGATAAGCTA | 221 |
| miR-31 | AGCTATGCCAGCATCTTGCCT | 222 |
| miR-142-3p | TCCATAAAGTAGGAAACACTACA | 223 |
| miR-195 | GCCAATATTTCTGTGCTGCTA | 224 |
| miR-98 | AACAATACAACTTACTACCTCA | 225 |

TABLE 12 microRNA precursor sequences and chromosomal locations

| probe | microRNA precursor sequence 5' -> 3' | SEQ ID | chr | start | end | strand |
|---|---|---|---|---|---|---|
| 25-R5-2 | TCCCGCAGCCGGTGACTGGAGCCCACCTCTGCAGAGACAAAGGTTAGAAAAG AGGGGGTGAGGCTCTGGGAAAGCAGAATGCGGGG | 226 | 2 | 176709550 | 176709636 | -1 |
| 227-L5-1 | TGAGGGGCGGAAGCACTGGGGAGAGACAGGTGTGAGCTTCCCACGTGGTGATC AGCTCACACCTGTCTTGTGTTCTTGGTATTCACAGACTCTCA | 227 | 3 | 187350863 | 187350957 | 1 |
| 836-R4-1 | AAATAAGCCATTCCAAACCATTCTCTGATTTGCTGTGAGTGGCAGAATCATTC ACCGTGGTGAATCATAGCAGGGAGAACCATTTGGAATGATTATTT | 73 | 3 | 170758581 | 170758678 | -1 |
| 2819-L5-2 | AATGCCAGTGAGTTTGAAAGGCACTTTGTCCAATTAGAAGTGTGGAGAAATAT TCATCCTGTCCATGACAAAGATGAAGTGCTTCTTTCAAAAGCGGCGGTGGCAG GCTG | 228 | 15 | 59266509 | 59266618 | 1 |
| 2819-R5-4 | AATGCCAGTGAGTTTGAAAGGCACTTTGTCCAATTAGAAGTGTGGAGAAATAT TCATCCTGTCCATGACAAAGATGAAGTGCTTCTTTCAAAAGCGGCGGTGGCAG GCTG | 229 | 15 | 59266509 | 59266618 | 1 |
| 3371-L4-1 | CTCAAGTGTGGGGAGTCATGGGGTGTGGAGGGGAGGAAAGGAAAGGTATTTTG TTTCTTTGTCTATACATTTCCTAGATTTCTATGCAGTTGGG | 42 | 18 | 58394821 | 58394914 | 1 |
| 3744-R5-1 | CTTCTCTTATTCTCCCTGTTTTCATCCTACTTTTAAGTAATAAATTTGGCATT AGTGGGAGGGGAGCAGGGAGGAAGGAGAAG | 230 | 19 | 14176021 | 14176103 | 1 |
| 3911-R5-1 | GGCCCTTAGGAAATTAGAGTGTGTTTGAATTTCACAAGTATAATTTTAATTAT ACAAATTTTGCATTTTTTCACTAGGGAGCC | 231 | 17 | 52705568 | 52705650 | 1 |
| 3995-L2-1 | TGGCCTGACGTGAGGAGGAGGGACTTTTCGAAGTTTTATAGGAAAGTTTCCGC TTTCCAGTCCCCCTCCCCGTCCCA | 232 | 7 | 19123856 | 19123933 | 1 |
| 4417-R5-2 | GCTGGGGTTCATCGGAGAAACTCCCTGCGATGAGCCACTAGGGTCACGGACAG GGAACTTTTTGATGAGCGCCGAGT | 233 | 14 | 34943859 | 34943935 | 1 |
| 4440-L3-2 | GTGATGTGATTTCTGCCCAGTGCTCTGAATGTCAAACTGAAGAAATTCAGTGA AATGCGGGTAAACGGCGGGAGTAACTATGAC | 234 | 7 | 68165348 | 68165431 | 1 |
| 4440-R3-2 | GTGATGTGATTTCTGCCCAGTGCTCTGAATGTCAAACTGAAGAAATTCAGTGA AATGCGGGTAAACGGCGGGAGTAACTATGAC | 235 | 7 | 68165348 | 68165431 | 1 |
| 4498-L3-2 | TTCCCCAGGCAGCAGCAGGCGCACGGCCGTCTGGATCTCCCTGGAGGTGATGG TCGAGCGCTTGTCATAATGCGCCAGGCGGGA | 236 | 6 | 25840053 | 25840136 | 1 |
| 4719-R5-1 | ACAGCGGCATGGTTCATGCCAAATTCCGAAGCAATCTTCCTGCTAAGGCCACT GGACACAGAATCCATGTGATGCTGT | 237 | 13 | 71318356 | 71318433 | 1 |

TABLE 12-continued microRNA precursor sequences and chromosomal locations

| probe | microRNA precursor sequence 5' -> 3' | SEQ ID | chr | start | end | strand |
|---|---|---|---|---|---|---|
| 4765-L5-1 | GGAGCCCGAGAAACTAAGAGAAAGTGTCAGGAGCATGTTAATCAGACTCGTTA CACTGTAACAATAACGTCTCTCTCGGGTCTCC | 238 | 13 | 99346548 | 99346632 | 1 |
| 4829-R2-1 | GGTGTGTCTGCCTCTCTTTCTGCCCCCCTATACCCCTTGACCCCAGGGGAAG GCACTCGGGCAGCACAAAGGGAGCAGATGCCC | 239 | 1 | 149949355 | 149949439 | 1 |
| 4855-R5-1 | GGGTCCGGGTCTCTACCGCGCCCTCATGCAGGAGGCCCTTGGAGCAGGAGGGG GAAGCGGGAGACCCGGCAGCCC | 240 | 12 | 46684439 | 46684513 | 1 |
| 4988-R5-2 | CTTTTTCTCTCTGCTGGGAAACCTTGCTTGACTTCATGTCCAGTGTTTGGTAT CCAAAGACGGGGAGGAGGAG | 241 | 14 | 77814294 | 77814366 | 1 |
| 5192-L3-2 | GTCTTTGCTGATATAGAGGAAGGAAGGGGAAAAATGAGCGCATTAGTTCTCTT TTATTAAAAGAGTTATTTCAGCATGAC | 58 | 5 | 168281079 | 168281158 | 1 |
| 4440-L3-2 | CATGTGATTTCTGCCCAGTGCTCTGAATGTCAAAGTGAAGAAATTCAATGAAG CACGGGTAAACGGCGGGAGTAACTATG | 242 | 11 | 77275152 | 77275231 | 1 |
| 6216-L1-1 | CATGTGATTTCTGCCCAGTGCTCTGAATGTCAAAGTGAAGAAATTCAATGAAG CACGGGTAAACGGCGGGAGTAACTATG | 243 | 11 | 77275152 | 77275231 | 1 |
| 6216-R5-2 | CATGTGATTTCTGCCCAGTGCTCTGAATGTCAAAGTGAAGAAATTCAATGAAG CACGGGTAAACGGCGGGAGTAACTATG | 244 | 11 | 77275152 | 77275231 | 1 |
| 6235-R5-2 | TCTGTTTTTATCAGTTTAATATATGATACATCTTCTATCCAAGGACAATATAT TAAATGGATTTTTGGAGCAGA | 245 | 15 | 94090075 | 94090148 | 1 |
| 6803-R5-2 | GCCACCTTTCATGGTGAGGATGCCTGCCACCTTCAGGATCACATCTTTGGGTG AGGTCCAACCAGAGAGGGAGC | 246 | 22 | 33316496 | 33316569 | 1 |
| 7067-L5-1 | GGGCAGCAGCAGGCGCTCGGCCGTCTGGATCTCCCTGGAGGTGATGGTCGAGC GCTTGTTGTAATGCGCC | 247 | 3 | 115304855 | 115304924 | 1 |
| 7126-L3-1 | CAGGGGCGCGGGCCGGAGAGCGGGTGTGCAAAGTGGGCGCAGGGCCCTGGGGC CGCGCCCCTTGCTCTGCCGGCTCGACTCTTG | 248 | 5 | 134391424 | 134391507 | 1 |
| 7182-L5-1 | GGGGGCAGGGGAAGGTGACGGAAACGGCTAGTTACCCAGAATTCTCTGGGGGA ACCAGAAAAATCGGTTATCTAGAATTCTCCC | 249 | 12 | 55013754 | 55013837 | 1 |
| 7292-R3-2 | GCAATTAGAATGCAGGGAGGTTCAGAAGCTATTTAACTGGGTGACCCCTGAGG TCGCTGCATCTGACTCCCATCCCTGGATAAATATTGT | 250 | 1 | 44534497 | 44534586 | 1 |
| 7352-R3-2 | GCCTCTGTGCGCATGGATATAATCAGCTTTGATAGGCAGAGGCTGAGGCTGTT TTTCCAATTAGAGCTGTTAGAGGATTCTGGCAGGGGC | 67 | 1 | 178017933 | 178018022 | 1 |
| 7578-L3-1 | GAGGGGCTGTAGCTCAGGGTGTGCACTGCGAGGCTGGACCTGTTGAGTCTGCA GTGGACATCCATTTAGCTTCAGGTTGTC | 251 | 2 | 104755260 | 104755340 | 1 |
| 7781-R5-2 | AGCCTGTTCCGTGCTCGCTAACTATAAACTATCTGATTTATATTCATTAACCA GTACTAGACAGCGGCAGGCACAGGCT | 252 | 17 | 32249690 | 32249768 | 1 |
| 7887-L5-3 | ACAGTAGGTATAGCTGGCATGGGACTGGTAGTGCAGGCTGGCTCTTGGAAAGG AGTATGTATTCCAGGCTGGTTGGCTGCTGT | 253 | 11 | 24870096 | 24870178 | 1 |
| 8004-R3-2 | GGGGCTGCCATCCTGCTGTCCGTCATCTGTGTGGTGCTGGTCACGGCCTTCAA TGACTGGAGCAAGGAGAAGCAGTTCC | 254 | X | 152460383 | 152460461 | 1 |
| 8298-R5-1 | GATGCCGGGCGCCCGCCGCAGCCGCTGCCGCCGGAGCCCGGGATGGGGCGAGA GGCTGCGGCGGACGCCAGCATC | 255 | 22 | 38183356 | 38183430 | 1 |
| 8339-R5-1 | AAGAGCACAAACCTTTCATTTTGCCGTTTATTTGTCTTGTGGCCGGTACAGTG AAAATGTATTGGCTTTT | 256 | 8 | 37597525 | 37597594 | 1 |
| 8433-L3-1 | CGGTGGAGGGAAAGGGGAAAGGAGCCATTTTCTGCTGCACATCAGTCAGTGCC TGCGCCCTCCCTCCCTCCGCCG | 53 | 17 | 75427043 | 75427117 | 1 |
| 7887-L5-3 | ACAGTAGGTATAGCTGGCATGGGACTGGTAGTGCAGGCTGGCTCTTGGAAAGG AGTATGTATTCCAGGCTGGTTGGCTGCTGT | 257 | 3 | 29199527 | 29199609 | -1 |
| 9053-R3-1 | GGAAGGGCACTGTCTCTCTGATTCCCAGGGCCTGTCATTTCCCGAGGGCTGGT GGAGCCCGGGGATTGGAGGGCAAGAAGCCCAGCC | 46 | X | 144618949 | 144619035 | 1 |
| 9164-R5-1 | TGTTTTCATCTTGCTTCTTCATGGTCCATGATGCCAGCTGAGGTTGTCAGTAC AATGAAACCAAACTGGCGGGATGGAAGCA | 258 | 1 | 218383957 | 218384038 | 1 |

TABLE 12-continued microRNA precursor sequences and chromosomal locations

| probe | microRNA precursor sequence 5' -> 3' | SEQ ID | chr | start | end | strand |
|---|---|---|---|---|---|---|
| 9485-R5-1 | CTGGGAACAATGGGGCCATTGTGGGAGGATGGAGTGCAGCAGACTGCTGGCACAGCCAAGCGCACCACGGTGGGACCTCACCCAG | 259 | 11 | 118290213 | 118290297 | 1 |
| 9691-L4-1 | GCAAGGGGCCAAGAGGGAGATGCGGATGAAATGGATGATTTAATGGGTCATCTCTCCTGTAGTTAATTTCTCTAGATCTCTTGT | 48 | 14 | 77897549 | 77897632 | 1 |
| 9774-R2-1 | GCTTGTCCTAAAAGATCTTCCTTCTGTTTCCCTGGGTTTATCCACTTGGTTGGCCTGATGGGAGCAGGAGGCGGTGAGGGGCGGGC | 260 | 13 | 35312134 | 35312220 | 1 |
| 9816-R5-1 | CTGGCCCATTTTCATTCTGCATAAAATTTTAATGGTCTCTCTGGCTGATCCGGGACGGCAGCGCGCGGAGAGGCTCTTAAAGGGCCAG | 261 | 17 | 35028328 | 35028415 | 1 |
| 10030-R5-1 | GGATGCAACCGTGGAAGCCGGTGCCGTTGAGGATCTGCCACAGGCGGAAGGCAGCTGAGTTGACATCCACGGGCATCC | 262 | 10 | 98752662 | 98752739 | 1 |
| 10435-R4-1 | GAGGCTGCTTAATGAGGTGCCCTTTTCAAAATGTCATCTTAATCTTTTATTAGTTTAAGAAAGACAACAGGGCACAATTAGCATGCAACTC | 263 | 5 | 168043163 | 168043253 | -1 |
| 4315D-R4-1 | GGGGACGTGGCCCCTCCCCCCCGGAGCGGGACTCCAAGAACTCCGGGGGCGCTGGGGGCTGACTTTCC | 264 | 1 | 153319527 | 153319595 | 1 |
| 999996-L4-1 | GTCTTCCCCCAACCCACAGCACACACCTGACTCCTCCCTTCCAGGGAAAAGACCTCAGGGCTGCTGGTGAGTCAGAAATAGGAAGAC | 265 | 17 | 35759252 | 35759338 | -1 |
| 12730-R5-2 | CCCGGCTCGGCCCCGCGTCTCTCCAGCTCCTCCGGCTCCTTTTAGTGCATAAATTAGTGATGGCATTTCCCGGAGAGCGGAGCACAACACAGGGCGCCGGGCTCGGG | 266 | 17 | 75427123 | 75427229 | 1 |
| 12917-R5-1 | GGACCTGGGGGCTTCTCTGACCCTTGAACAGCTTATACTATGAGACCTTGGGAACCTCCTCCATGCAGACACACAAGGCTCAATGTTGGGGGAAGGGAAGGGCCCATAGGTCC | 267 | 1 | 45246668 | 45246780 | 1 |
| 12917-R5-2 | GGACCTGGGGGCTTCTCTGACCCTTGAACAGCTTATACTATGAGACCTTGGGAACCTCCTCCATGCAGACACACAAGGCTCAATGTTGGGGGAAGGGAAGGGCCCATAGGTCC | 268 | 1 | 45246668 | 45246780 | 1 |
| 13075-L5-1 | AGAGGGCTGGGCTGGACTTCAGCTTTCACCTAGGAAATGAGTCTTGCTGCCCTTT | 269 | 2 | 42137734 | 42137788 | 1 |
| 13108-L5-2 | TTCCCACACGTGCTCAGGCCCCTCAACCAAGGAAGGCAGCAGGCCCACTGGCCTCCTTATTCAGAGGGGCTGCACTGCACCCTAGGGAG | 270 | 2 | 31479610 | 31479698 | 1 |
| 13111-L5-3 | AGCCTGTGGGAAAGAGAAGAGCAGGGCAGGGTGAAGGCCCGGCGGAGACACTCTGCCCACCCCACACCCTGCCTATGGGCCACACAGCT | 271 | 16 | 3475382 | 3475470 | -1 |
| 13122-L5-1 | GGACTGGAGCAGGTGAGATGGAATTTCCTAAAGGTCCAGATATTTAGGACCCTGGACCCATCTCACCCGCTGCCTCTGTCC | 272 | 2 | 85447047 | 85447127 | 1 |
| 13124-L5-2 | TGAGGGGTAAGTTTAGGCTTTCGCGGAGGGGAGGAGACATGGAGCCTGGGAACTCCTTGTTCTCCCCTCTGCTGCCTCTCCCCACCCCTTA | 273 | 1 | 154700544 | 154700634 | -1 |
| 13129-L5-3 | CCAGACTCTGGGTGGATGGAGCAGGTCGGGGGCCAGGGGACAGGAAGGCTAGGGCCCCAGAGACCTGTCCTGGGCCCCATGTCCAGCTCTGCCCTTAGTGCTTGG | 274 | 20 | 61388629 | 61388733 | 1 |
| 13168-L5-1 | GTGGTTAAAAAAAAAAAAAATGGTTAAGGAAGCGGACCATGGAGCAGAAAGTTGCAGTGACTGGATTCTGGCTCCAGGCTGCAAATTTAACCATTGAATATCAC | 275 | 11 | 78788919 | 78789022 | -1 |
| 13181-L5-2 | TCCTGAAAGAGGTTGGGCAGGCAGTGACTGTTCAGACGTCCAATCTCTTTGGGACGCCTCTTCAGCGCTGTCTTCCCTGCCTCTGCCTTTAGGA | 276 | 1 | 98283397 | 98283491 | -1 |
| 13195-L5-1 | AAAAAAAAAAAGATACTAATACAAATGGTCATGGAGGGGAATATAGAGAAGATCAATTTTGTACAGAAAAACCATTGGTTAGTATTTTTTTTCTTTT | 277 | 3 | 54069253 | 54069352 | 1 |
| 13207-R5-4 | GCCCCCCAAAATGCTTCTGTACCCCTGCCCCAACAAGGAAGGACAAGAGGTGTGAGCCACACACACGCCTGGCCTCCTGTCTTTCCTTGTTGGAGCAGGGATGTAGAAGCACTTGCCGCAG | 278 | 10 | 677614 | 677734 | -1 |
| 13209-L5-2 | GGGAGCCGCCGGCGGGCAGGCCGCCGGGGCAGCAGGCGAGTTACCTCAACTCCCGGCCGCTCCGGAGGTTGCCGGGCACCGAGGAGCCGCCGTGCCCTTCAGGCGCCTGCGGCGGCGACCA | 279 | 10 | 74122118 | 74122238 | 1 |
| 13219-L5-1 | GCTGGAGCAGAGAGACTGAGTGAGGGAGTCAGAGAGTTAAGAGAATTAGTACAGGTGAGATTGTACTGATTATCTTAACTCTCTGACCCCCTCACTCAGTAAAGATCAGATTGTGCCAGGC | 280 | 11 | 100895740 | 100895860 | -1 |

TABLE 12-continued microRNA precursor sequences and chromosomal locations

| probe | microRNA precursor sequence 5' -> 3' | SEQ ID | chr | start | end | strand |
|---|---|---|---|---|---|---|
| 13227-L5-2 | AAGCAAGACACCGAGGTGGGAAGGGGGACGAGGAGGACTGGGCCCTATTTCTCCCATCTATGTAAAGGGAGGGATATCAGGGAAGTCTCTGTCTGTGTACTCAAGTTTGGGATGCT | 281 | 11 | 133373044 | 133373159 | 1 |
| 13229-R5-3 | TGCTGGCCCAAGGGGTAAAGGGGCAGGGACGGGTGGCCCCAGGAAGAAGGGCCTGGTGGAGCCGCTCTTCTCCCTGCCCACAGAGACTGGCGGAGCTGC | 282 | 11 | 199324 | 199422 | 1 |
| 13231-L5-3 | AGGAACAGGACGATGATGCTGGCGTCGGTGCTGGGGAGCGGCCCCCGGGTGGGCCTCTGCTCTGGCCCCTCCTGGGGCCCGCACTCTCGCTCTGGGCCCGCTCCTCTTCC | 283 | 11 | 34919943 | 34920052 | 1 |
| 13247-L5-3 | ATCTCACAGAGGAAGAACAGGGCTCTGAGGTCGGGAGGGGAAGGCGGCTCAGGACTTCTGGCTCCAGAGCCTCCTCTCCTTCCACCATAGTGCCTGCTCCAGAGGAGAC | 284 | 1 | 165748638 | 165748746 | 1 |
| 13252-L5-3 | CTTTGGCACAGTCCGTGCTCTCAAGGAGCTCACAGTCAGGAAGGCACGTGGAATTTCAGCCTGGAGTTCCAAGTGCTGCCCTCAGGGAGTGCTGGGCCTGAGCTGGGGTGAGGCTGCAGGG | 285 | 1 | 176734861 | 176734981 | -1 |
| 13254-R5-1 | CTCACACATGGTACGTTTTCAATGAGCTGATTTTGTTTCTCCACTCAATGCAGTAATTGAGCTTCTTTGGTTCAGTGCATGAGTGGTTCAGTGGTTCATTGGGCATCCTGGTTGAGGG | 286 | 1 | 181542244 | 181542361 | -1 |
| 13260-L5-2 | GTGCTATAGCTATAGAGACTGAGTGTGGGGTCTACAGAAAATGTGGCCATGCCCTCCACCCCAGTGGCTGGGCAGCCTTTGGCACAG | 287 | 1 | 210949402 | 210949488 | -1 |
| 13267-L5-1 | CACCATAGGTGAGGTGGGGGCCAGCAGGGAGTGGGCTGGGCTGGGCTGGGCCAAGGTACAAGGCCTCACCCTGCATCCCGCACCCAGGCTTCAACGTGG | 288 | 1 | 226351579 | 226351677 | 1 |
| 13274-L5-3 | AGGTGGTGGTGGGGAGGACCCTGAGGGAGGGTGGGAGCACGGGAGAAGAGAAGGCATACCCAACCTGACCTACTTACCTGTCCCCTACCCCACAGAGGGCTTCCCTGGAGGCCGCCATTGC | 289 | 12 | 51578925 | 51579045 | -1 |
| 13283-L5-3 | GGGCACGGGGGTTGGGTGTGCAAAGGGTGGCAGCAAGGAAGGCAGGGGTCCTAAGGTGTGTCCTCCTGCCCTCCTTGCTGTAGACTTTGGCCTGAGCAAAGAGGCC | 290 | 1 | 26753591 | 26753696 | 1 |
| 13291-L5-1 | CGGGAGGGAAGGAGGGAGGAAGGGGCGCTTGGGCAGAACCAAGGGTGGCAGATTATCCTAGGGACTCTTGGGGCAGAACCAGACGCCTCTGCGTCCTCCCCTCTCCCC | 291 | 1 | 36545595 | 36545702 | 1 |
| 13296-L5-3 | CAGGAATTCCACTGGCAGCCAGGGCAGAGGGCACAGGAATCTGAGGTGACTGGCACAGAAGACTCAGGCCTGTGGCTCCTCCCTCAGGACTGCTTCCTA | 292 | 1 | 43686783 | 43686881 | 1 |
| 13312-L5-1 | GTGAGTGGGGCTGGGCTGTGGGGGAGGGGTGGGGTGGCAGGGAACAGGCAGACCATCCCTTCTACCCACAGGATCCTGCTGCTGCAGACAG | 293 | 15 | 72689606 | 72689696 | -1 |
| 13325-R5-2 | ACTCAGGCACTGCCTCTGACGATGCTCTCCCAGATCTGGTACGCTCATGGGAAGAGCCCAGCGCCAGGCAGTGTTGGA | 294 | 16 | 88088866 | 88088944 | 1 |
| 13335-L5-2 | TGGCTGGGAGAGGAGCATAGGATGCGGCAGGAGGGCAGTGGAGGCTGAGGTACGGATTTCTAGGCCCGCCCTACCCTCCTCTCTGCCCCTAGTGCCCGTGGCCAA | 295 | 17 | 4803649 | 4803753 | -1 |
| 13335-L5-3 | TGGCTGGGAGAGGAGCATAGGATGCGGCAGGAGGGCAGTGGAGGCTGAGGTACGGATTTCTAGGCCCGCCCTACCCTCCTCTCTGCCCCTAGTGCCCGTGGCCAA | 296 | 17 | 4803649 | 4803753 | -1 |
| 13339-L5-1 | GCGGCGGACACCATCTTCTTTAAACCCTCAGTCCGTATTGGTCTCTATGGCATCCATAGAGGCCATTCGGCTCTGAGGTCCTCAGTAAAGAAACTTAGATGGTATTACTGTGT | 297 | 17 | 7150842 | 7150954 | -1 |
| 13504-R5-3 | TCACATGTCCTCAGCTGTTGTCTGGGTGAGGCATCCCTGTCGTGGGAGCAGCCACAGCTCTGCCTGGTCTCCCAGAGCAGGGACGCTTTGTCCGCATTTACAGCAGTCTACACAGATG | 298 | 7 | 150369385 | 150369502 | 1 |
| 13532-L5-2 | AGCCACACGGTCACACCTAATGTCATAGCCGGTAGAGCAGGGAGCCCTCTGGATGGAAGCACTGTGAGGCTC | 299 | 9 | 131989877 | 131989948 | -1 |
| miR-1246 | TGTATCCTTGAATGGATTTTTGGAGCAGGAGTGGACACCTGACCCAAAGGAAATCAATCCATAGGCTAGCAAT | 300 | 2 | 177173954 | 177174026 | -1 |
| miR-1290 | GAGCGTCACGTTGACACTCAAAAAGTTTCAGATTTTGGAACATTTCGGATTTTGGATTTTTGGATCAGGGATGCTCAA | 301 | 1 | 19096152 | 19096229 | -1 |
| miR-1308 | CCCCGCATGGGTGGTTCAGTGGCAGAATTCTCAAATTGTAATCCCCATAATCCC | 302 | X | 21990180 | 21990233 | -1 |

TABLE 12-continued microRNA precursor sequences and chromosomal locations

| probe | microRNA precursor sequence 5' -> 3' | SEQ ID | chr | start | end | strand |
|---|---|---|---|---|---|---|
| miR-142-3p | GACAGTGCAGTCACCCATAAAGTAGAAAGCACTACTAACAGCACTGGAGGGTGTAGTGTTTCCTACTTTATGGATGAGTGTACTGTG | 303 | 17 | 53763592 | 53763678 | -1 |
| miR-1826 | ATTGATCATCGACACTTCGAACGCAATTGCAGCCCGGGTTCCTCCCAGGGCTTTGCCTGTCTGAGCGTCGCTTGCCGATCAGTAG | 304 | 16 | 33873009 | 33873093 | 1 |
| miR-195 | AGCTTCCCTGGCTCTAGCAGCACAGAAATATTGGCACAGGGAAGCGAGTCTGCCAATATTGGCTGTGCTGCTCCAGGCAGGGTGGTG | 305 | 17 | 6861658 | 6861744 | -1 |
| miR-200c | CCCTCGTCTTACCCAGCAGTGTTTGGGTGCGGTTGGGAGTCTCTAATACTGCCGGGTAATGATGGAGG | 306 | 12 | 6943123 | 6943190 | 1 |
| miR-451 | CTTGGGAATGGCAAGGAAACCGTTACCATTACTGAGTTTAGTAATGGTAATGGTTCTCTTGCTATACCCAGA | 307 | 17 | 24212513 | 24212584 | -1 |
| miR-483-5p | GAGGGGGAAGACGGGAGGAAAGAAGGGAGTGGTTCCATCACGCCTCCTCACTCCTCTCCTCCCGTCTTCTCCTCTC | 308 | 11 | 2111940 | 2112015 | -1 |
| miR-491-3p | TTGACTTAGCTGGGTAGTGGGGAACCCTTCCATGAGGAGTAGAACACTCCTTATGCAAGATTCCCTTCTACCTGGCTGGGTTGG | 309 | 9 | 20706104 | 20706187 | 1 |
| miR-494 | GATACTCGAAGGAGAGGTTGTCCGTGTTGTCTTCTCTTTATTTATGATGAAACATACACGGGAAACCTCTTTTTTAGTATC | 310 | 14 | 100565724 | 100565804 | 1 |
| miR-720 | CCGGATCTCACACGGTGGTGTTAATATCTCGCTGGGGCCTCCAAAATGTTGTGCCCAGGGGTGTTAGAGAAAACACCACACTTTGAGATGAATTAAGAGTCCTTTATTAG | 311 | 3 | 165541823 | 165541932 | 1 |
| miR-765 | TTTAGGCGCTGATGAAAGTGGAGTTCAGTAGACAGCCCTTTTCAAGCCCTACGAGAAACTGGGGTTTCTGGAGGAGAAGGAAGGTGATGAAGGATCTGTTCTCGTGAGCCTGAA | 80 | 1 | 155172547 | 155172660 | -1 |
| miR-98 | AGGATTCTGCTCATGCCAGGGTGAGGTAGTAAGTTGTATTGTTGTGGGGTAGGGATATTAGGCCCCAATTAGAAGATAACTATACAACTTACTACTTTCCCTGGTGTGTGGCATATTCA | 312 | X | 53599909 | 53600027 | -1 |
| miR-143 | GCGCAGCGCCCTGTCTCCCAGCCTGAGGTGCAGTGCTGCATCTCTGGTCAGTTGGGAGTCTGAGATGAAGCACTGTAGCTCAGGAAGAGAGAAGTTGTTCTGCAGC | 313 | 5 | 148788674 | 148788779 | 1 |
| miR-145 | CACCTTGTCCTCACGGTCCAGTTTTCCCAGGAATCCCTTAGATGCTAAGATGGGGATTCCTGGAAATACTGTTCTTGAGGTCATGGTT | 314 | 5 | 148790402 | 148790489 | 1 |
| miR-205 | AAAGATCCTCAGACAATCCATGTGCTTCTCTTGTCCTTCATTCCACCGGAGTCTGTCTCATACCCAACCAGATTTCAGTGGAGTGAAGTTCAGGAGGCATGGAGCTGACA | 315 | 1 | 207672101 | 207672210 | 1 |
| miR-21 | TGTCGGGTAGCTTATCAGACTGATGTTGACTGTTGAATCTCATGGCAACACCAGTCGATGGGCTGTCTGACA | 316 | 17 | 55273409 | 55273480 | 1 |
| miR-31 | GGAGAGGAGGCAAGATGCTGGCATAGCTGTTGAACTGGGAACCTGCTATGCCAACATATTGCCATCTTTCC | 317 | 9 | 21502114 | 21502184 | -1 |

Microarray Validation

One or two microarrays were used for each of the samples in Table 8.

All sequences for which the intensity of the spot was higher than the local background mean intensity plus 1.5 times its standard deviation were declared "expressed." The normalization was based on the signal obtained for positive controls.

The following parameters where used to check the quality of the microarray data for this experiment.

Control HeatMap: allows verification, after normalization, of:
a. the low signal of the negative control,
b. the specificity (CTL26 versus CTL26_MUT),
c. the approximate equality between positive control signals (without CTL30, which is a purification and labelling control),
d. the approximate equality between block signal medians (based only on positive controls),
e. the approximate equality between array signal medians (based on all sequences detected)
f. the purification and labelling control (CTL30).

Correlation within Sample Type:
for one sample type, the correlation between technical replicates (2 by 2) are computed, then the mean of all correlations obtained is computed.

Approximation of the Number of Detected Sequences by Sample:
When only one array is run for a sample, a very large or very small number of detected sequences may suggest a technical problem.

Effect of the Block and Array on the Normalized Signal:
based on the positive controls used for normalization, an ANOVA analysis is done to show the effect of the block and the array on the normalized signal. We check that the normalized signal obtained for one control on a particular block and a particular array is not due to the particular block or array.

Standard Deviation for Positive Control within One Particular Array and Among all Arrays:

The standard deviation for each positive control among all arrays is computed, as well as the mean of the standard deviation obtained for each control within one particular array. The normalization process may allow computation of similar "intra" and "inter" array variation (mean of standard deviation obtained within each array and standard deviation among all arrays).

Ability of the miRNA Profiles to Distinguish Sample Type:

A hierarchical classification among all arrays is applied, taking into account all predictions (the distance used is based on Pearson correlation and the agglomerate method is "Ward's minimum variant method"). A good clustering by sample type (technical replicates) indicates data of good quality.

Results of Microarray Validation

Control Heatmap:

The positive, block, and labeling/purification controls gave approximately the same normalized signals. We found that the specificity of all of the arrays was excellent.

Correlation, Standard Deviation, Approximate Number of Detected Sequences.

As shown in Table 13, the correlations obtained for tissues with two technical replicates were excellent. A higher or lower number of detected sequences were observed in some tissues compared to the typical number of detected sequences (see Table 13, bold rows). That result may be due to the degradation state of the RNA obtained.

TABLE 13

| | Correlation (mean) | Number of detected sequences | Number of Arrays kept for analysis | Number of Arrays not computed |
|---|---|---|---|---|
| ASCC-1 | — | 322 | 1 | 0 |
| SCC-1 | 0.983 | ~400 | 2 | 0 |
| SCC-2 | 0.969 | ~300 | 2 | 0 |
| ADC-1a | — | 97 | 1 | 0 |
| normal | — | — | 0 | 1 |
| SCC-3a | 0.962 | ~300 | 2 | 0 |
| SCC-4 | 0.99 | ~100 | 2 | 0 |
| SCC-1b | 0.986 | ~250 | 2 | 0 |
| SCC-3b | — | 291 | 1 | 1 |
| ADC-1b | — | 74 | 1 | 0 |
| SCC-5 | 0.978 | ~450 | 2 | 0 |
| ASCC-1b | — | 624 | 1 | 0 |
| CIN1 | — | — | 0 | 1 |
| SCC-6 | — | 123 | 1 | 0 |
| CIN3 | — | — | 0 | 1 |
| SCC-7 | — | 610 | 1 | 0 |
| SCC-8 | — | 249 | 1 | 0 |
| ex-normal-1 | — | 109 | 1 | 0 |
| ex-normal-3 | — | 66 | 1 | 0 |
| ex-normal-4 | — | 365 | 1 | 0 |
| Mean/Total | 0.978 | 961 | 23 | 14.81% |

Effect of the Array and Block on the Normalized Signal Obtained.

Based on the ANOVA analysis, we observed no effect of the array and block on the positive control normalized signal.

Standard Deviation of Positive Controls.

The intra-array standard deviation was 0.29, and the inter-array standard deviation was 0.32. Both numbers are low and suggest little array effect on the normalized signals.

Ability of the miRNA Profiles to Distinguish Between Sample Types.

All tissues that were analyzed in duplicate clustered together in this analysis, suggesting that the miRNA profiles did distinguish between sample types.

Based on the quality criteria considered, this microarray experiment was technically successful. For some tissues, however, a low number of sequences were detected, suggesting that tissue or RNA degradation may have affected some samples.

5.4 Example 4: mRNA Expression in Cervical Cell Lines and Clinical Samples

Cell Lines and Tumor Samples

The cell lines shown in Table 5 were used in this experiment. Total RNA from the cell lines was prepared as described in Example 1.

In addition, total RNA from two normal cervix and one squamous cervical tumor (SCC) were purchased from Applied Biosystems (Foster City, Calif.). See Table 14.

TABLE 14

Total RNA from Ambion

| sample | Applied Biosystems |
|---|---|
| normal cervix - Ambion #1 | AM6992 lot no. 07060421 |
| normal cervix - Ambion #2 | AM7276 lot no. 03030243 |
| cervix tumor - Ambion #1 (squamous) | AM7277 lot 03030253 |

Total RNA was prepared from fresh frozen samples using TRIzol® Reagent (Invitrogen; Carlsbad, Calif.) according to manufacturer's protocols. All RNA samples showed a good A260/280 ratio.

TABLE 15

Clinical samples

| Sample name | Sample type |
|---|---|
| SCC-1c | Frozen |
| SCC-3b | Frozen |
| SCC-4b | Frozen |
| SCC-5 | Frozen |
| SCC-8 | Frozen |
| SCC-9 | Frozen |
| SCC-10 | Frozen |
| ADC-1b | Frozen |
| ASCC-1b | Frozen |
| CIN1#1 | Frozen |
| CIN1#2 | Frozen |
| CIN2#1 | Frozen |
| cx-normal-6 | Frozen |
| cx-normal-8 | Frozen |
| cx-normal-9 | Frozen |
| cx-normal-12 | Frozen | cDNA Synthesis—Cell Lines and Ambion Samples

Reverse transcription was performed using 1 µg total RNA. In each case, the cDNA preparation was performed in a 50 µL reaction volume using random hexamers and TaqMan® reverse transcription reagents (Applied Biosystems; Foster City, Calif.) according to manufacturer's instructions. In parallel, the same reactions were performed without the reverse transcriptase as no-RT controls.

cDNA Synthesis—Clinical Samples

Reverse transcription was performed using 0.5 µg total RNA in a 20 µL reaction volume using random hexamers and the High Capacity cDNA RT kit from Applied Biosystems, Inc. (Foster City, Calif.) according to manufacturer's protocol. In parallel, the same reactions were performed without the reverse transcriptase as no-RT controls. In order to evaluate the variation of cDNA synthesis within a sample, three parallel cDNA syntheses were performed on a selection of RNA samples.

Selection of Reference Genes

For the cell lines, ACTB and TBP were used as reference genes. For the clinical samples, ACTB, TBP, and GAPDH were used as reference genes for the clinical samples.

Selection of mRNA Targets

The mRNA targets are shown in Table 16.

TABLE 16 mRNA targets

| gene | alias | amplicon size | exon boundary | comment |
|---|---|---|---|---|
| CDKN2A | p16$^{ink4}$ | 70 | 1-2 | all major isoforms |
| BIRC5 | survivin | 86 | 1-2 | all major isoforms |
| TOP2A | | 72 | 23-24 | |
| MCM5 | | 70 | 16-17 | |
| KRT19 | CK19 | 64 | 2-3 | |
| EPCAM | TACSTD1 | 82 | 2-3 | |
| MMP2 | | 86 | 10-11 | |
| MMP9 | | 67 | 1-2 | |
| MCM2 | | 82 | 2-3 | |
| VEGFC | | 93 | 4-5 | |
| TERT | | 94 | 3-4 | |
| PCNA | | 117 | 5-6 | |
| RPSA | 67LR | 121 | 7 | |
| MAPK3 | Erk-1 | 64 | 2-3 | |
| IGF2BP3 | L523S, IMP-3 | 97 | 12-13 | |
| PIK3CA | | 104 | 6-7 | |
| POU4F1 | brn-3a | 104 | 1-2 | |
| MKI67 | Ki-67 | 66 | 8-9 | |

PCR

All PCR reactions were performed in triplicate in a 25 µL reaction volume on a Stratagene MX3000p instrument using a template concentration corresponding to 2 ng total RNA/reaction. TaqMan® Universal PCR Master Mix (Applied Biosystems Inc, Foster City, Calif.) was used for all reactions. The primers and probes used in the PCR reactions are shown in Tables 17 and 18. All probes were FAM-labeled and all reactions were run in singleplex.

TABLE 17

Primers and probes for mRNA target PCR reactions

| | | | SEQ ID |
|---|---|---|---|
| CDKN2A | | | |
| forward | 5'-CATAGATGCCGCGGAAGGT-3' | | 318 |
| reverse | 5'-CCCGAGGTTTCTCAGAGCCT-3' | | 319 |
| probe | FAM-CCTCAGACATCCCCGATTGAAAGAACC-TAMRA | | 320 |
| BIRC5 | | | |
| forward | 5'-CTTTCTCAAGGACCACCGCA-3' | | 321 |
| reverse | 5'-GCCTCGGCCATCCGCT-3' | | 322 |
| probe | FAM-CATTCAAGAACTGGCCCTTCTTGGAGG-TAMRA | | 323 |
| KRT19 | | | |
| forward | 5'-AGATCGACAATGCCCGT-3' | | 324 |
| reverse | 5'-AGAGCCTGTTCCGTCTCAAA-3' | | 325 |
| probe | FAM-TGGCTGCAGATGACTTCCGAACCA-TAMRA | | 326 |

TABLE 17-continued

Primers and probes for mRNA target PCR reactions

| | | | SEQ ID |
|---|---|---|---|
| EPCAM | | | |
| forward | 5'-TCATTTGCTCAAAGCTGGCTG-3' | | 327 |
| reverse | 5'-AAACTTGGGAGAAGAGCAAAACC-3' | | 328 |
| probe | FAM-AAATGTTTGGTGATGAAGGCAGAAATGAATGG-TAMRA | | 329 |
| VEGFC | | | |
| forward | 5'-TTCATTCCATTATTAGACGTTCCCT-3' | | 330 |
| reverse | 5'-GATTATTCCACATGTAATTGGTGGG-3' | | 331 |
| probe | FAM-CCAGCAACACTACCACAGTGTCAGGCA-TAMRA | | 332 |
| PCNA | | | |
| forward | 5'-TTAAATTGTCACAGACAAGTAATGTCG-3' | | 333 |
| reverse | 5'-TGGCTTTTGTAAAGAAGTTCAGGTAC-3' | | 334 |
| probe | FAM-TGGTTCATTCATCTCTATGGTAACAGCTTCCTCCT-TAMRA | | 335 |
| MMP9 | | | |
| forward | 5'-CCCTGGAGACCTGAGAACCA-3' | | 336 |
| reverse | 5'-AACCATAGCGGTACAGGTATTCCT-3' | | 337 |
| probe | FAM-TCTCACCGACAGGCAGCTGGCA-TAMRA | | 338 |
| MMP2 | | | |
| forward | 5'-CCTGAGATCTGCAAACAGGACAT-3' | | 339 |
| reverse | 5'-CCAAATGAACCGGTCCTTGA-3' | | 340 |
| probe | FAM-TTGATGGCATCGCTCAGATCCGTG-TAMRA | | 341 |
| IGF2BP3 | | | |
| forward | 5'-GCTAAAGTGAGGATGGTGATTATCACT-3' | | 342 |
| reverse | 5'-ACTAACAAAGTTTTCTTCTTTAATTTTTCCAT-3' | | 343 |
| probe | FAM-ACCAGAGGCTCAGTTCAAGGCTCAGGGAA-TAMRA | | 344 |

TABLE 18

Primer/probe kits used for mRNA target PCR reactions

| | Applied Biosystems Item Number |
|---|---|
| ACTB | Hs99999903_m1 |
| GAPDH | Hs00266705_g1 |
| TBP | Hs00427621_m1 |
| TOP2A | Hs03063307_m1 |
| MCM5 | Hs01052142_m1 |
| MKI67 | Hs010332443_m1 |
| POU4F1 | Hs00366711_m1 |
| MCM2 | Hs00170472_m1 |
| PIK3CA | Hs00180679_m1 |
| MAPK3 | Hs00385075_m1 |
| RPSA | Hs03046712_g1 |
| TERT | Hs99999022_m1 |

Primer and probe concentrations, as well as threshold settings used on the Stratagene MX3000 are shown in Table 19.

TABLE 19 mRNA target PCR conditions

| target | Master Mix 25 μL reaction | | | Threshold setting |
|---|---|---|---|---|
| | [forward] | [reverse] | [probe] | |
| CDKN2A | 300 nM | 300 nM | 100 nM | 500 |
| BIRC5 | 100 nM | 900 nM | 150 nM | 500 |
| EPCAM | 200 nM | 200 nM | 200 nM | 500 |
| KRT19 | 200 nM | 200 nM | 200 nM | 500 |
| VEGFC | 500 nM | 500 nM | 200 nM | 500 |
| PCNA | 500 nM | 500 nM | 200 nM | 500 |
| MMP2 | 500 nM | 500 nM | 200 nM | 500 |
| MMP9 | 500 nM | 500 nM | 200 nM | 500 |
| IGF2BP3 | 500 nM | 500 nM | 200 nM | 250 |
| RPSA 20X mix | | 1.25 μL | | 500 |
| MAPK3 20X mix | | 1.25 μL | | 500 |
| MCM5 20X mix | | 1.25 μL | | 250 |
| TOP2A 20X mix | | 1.25 μL | | 500 |
| TERT 20X mix | | 1.25 μL | | 250 |
| MCM2 20X mix | | 1.25 μL | | 500 |
| MKI67 20X mix | | 1.25 μL | | 500 |
| PIK3CA 20X mix | | 1.25 μL | | 150 |
| POU4F1 20X mix | | 1.25 μL | | 250 |
| ACTB mix | | 1.25 μL | | 500 |
| TBP mix | | 1.25 μL | | 500 |
| GAPDH mix | | 1.25 μL | | 500 |

All reactions, except for EPCAM, were cycled as follows: 10 minutes at 95°, followed by 40 cycles of 20 seconds at 95° C. and 1 minute at 60° C. For EPCAM, the reaction was cycled as follows: 10 minutes at 95°, followed by 40 cycles of 20 seconds at 95° C. and 1 minute at 64° C.

Expression and Statistical Analysis

For the analysis of relative expression, GenEx 4.4.2 software was used (multiD analysis, Gothenburg, Sweden). The GenEx software uses the ΔΔCt formula, compensating for differences in PCR efficiency. All fold-change values are calculated relative to one normal sample from Ambion (AM6992). The GenEx statistical module was used for descriptive statistics and t-test analysis.

Results

PCR Specificity.

Specificity was determined using no-RT controls and analysis of amplicon size on an agarose gel. All amplicons tested were of the expected size, and we observed no amplification in no-RT controls, except for the no-RT controls for PCNA and RPSA, which was at very low levels and may have been due to contaminating DNA.

PCR Efficiency.

In order to estimate the PCR efficiency for target and control mRNAs, a pool of cDNA from all of the cell lines was diluted in three-fold steps to generate a standard curve. PCR efficiency was calculated by the MX3000p software (Stratagene). Most assays had a similar efficiency, as shown in Table 20, except for MMP2, IGF2BP3, PIK3CA and POU4F1, which had very low expression levels in the cell lines, so it was not possible to generate a standard curve. We found that MMP9 was not expressed in cell lines at all.

TABLE 20

PCR efficiency in pooled cDNA from cell lines

| gene | PCR efficiency (%) |
|---|---|
| ACTB | 95 |
| TBP | 95 |
| GAPDH | 95 |
| CDKN2A | 95 |
| BIRC5 | 80 |
| TOP2A | 90 |
| MCM5 | 95 |
| KRT19 | 80 |
| EPCAM | 90 |
| MMP2 | too low expression |
| MMP9 | no expression in cell lines |
| MCM2 | 75 |
| VEGFC | 80 |
| TERT | too low expression |
| PCNA | 75 |
| RPSA | 95 |
| MAPK3 | 80 |
| IGF2BP3 | too low expression |
| PIK3CA | too low expression |
| POU4F1 | too low expression |
| MKI67 | 90 |

Expression in Cell Lines.

In this experiment, CDKN2A and MKI67 were highly elevated compared to the normal cervix sample from Ambion. BIRC5 and TOP2A also show elevated levels. See Tables 21 and 22. MMP2, MMP9, TERT, and POU4F1 generated very high or no Ct values. IGF2BP3 was expressed at fairly high levels in all but one cell line.

TABLE 21

Fold-changes in expression levels: Cell lines vs. normal#1 (Ambion)

| cell line | CDKN2A | BIRC5 | TOP2A | MCM5 | MKI67 |
|---|---|---|---|---|---|
| CaSki | 589.3 | 11.4 | 16.5 | 7.2 | 128.8 |
| SiHa | 241.6 | 5.3 | 3.3 | 1.3 | 47.0 |
| C4-1 | 294.6 | 5.1 | 2.7 | 0.5 | 85.6 |
| C4-2 | 899.5 | 17.7 | 49.5 | 22.9 | 507.9 |
| sw756 | 684.8 | 6.3 | 9.5 | 0.9 | 217.1 |
| ME-180 | 455.7 | 4.2 | 4.4 | 0.7 | 98.0 |
| C33-A | 523.7 | 4.3 | 12.0 | 3.9 | 67.8 |
| HeLa S3 | 487.1 | 5.1 | 20.8 | 3.9 | 137.4 |

TABLE 22

Fold-changes in expression levels: Cell lines vs. normal#1 (Ambion)

| cell line | KRT19 | EPCAM | MCM2 | RPSA | PCNA | MAPK3 | VEGFC |
|---|---|---|---|---|---|---|---|
| CaSki | 2.86 | 1.27 | 0.27 | 0.82 | 1.51 | 0.40 | 0.23 |
| SiHa | 0.02 | 0.02 | 0.13 | 0.20 | 0.36 | 0.21 | 0.06 |
| C4-1 | 2.11 | 2.19 | 0.06 | 0.80 | 1.02 | 0.61 | 0.26 |
| C4-2 | 4.79 | 1.47 | 0.97 | 3.49 | 3.79 | 2.72 | 0.12 |
| sw756 | No Ct | 0.20 | 0.14 | 0.58 | 1.46 | 0.36 | 0.17 |
| ME-180 | 2.05 | 0.36 | 0.16 | 0.28 | 0.81 | 0.37 | No Ct |

TABLE 22-continued

Fold-changes in expression levels: Cell lines vs. normal#1 (Ambion)

| cell line | KRT19 | EPCAM | MCM2 | RPSA | PCNA | MAPK3 | VEGFC |
|---|---|---|---|---|---|---|---|
| C33-A | No Ct | 0.03 | 0.31 | 1.90 | 0.55 | 0.78 | 1.72 |
| HeLa S3 | 0.06 | 0.03 | 0.61 | 1.27 | 1.70 | 0.36 | 0.60 |

Expression in Clinical Samples.

All of the clinical samples, except for CIN3, SCC6, and SCC7, generated reliable Ct values for all of the reference genes. CIN3, SCC6, and SCC7 were therefore excluded from the analysis. See Tables 23 and 24.

TABLE 23

Fold-changes in expression levels: Clinical samples vs. normal#1 (Ambion)

| Tissue samples | CDKN2A | BIRC5 | TOP2A | MCM5 | MMP9 | MKI67 |
|---|---|---|---|---|---|---|
| CIN1#1 | 21.6 | 9.5 | 26.1 | 23.0 | 70.9 | 0.2 |
| CIN1#2 | 24.0 | 1.0 | 1.3 | 1.9 | 1.1 | 0.8 |
| CIN2#1 | 30.8 | 3.5 | 3.7 | 0.4 | 2.0 | 1.2 |
| SCC1c | 304.3 | 7.0 | 65.7 | 31.6 | 14.0 | 137.9 |
| SCC3b | 202.2 | 5.5 | 79.5 | 39.8 | 6.4 | 107.0 |
| SCC4b | 282.1 | 9.9 | 39.3 | 13.4 | 3.4 | 46.4 |
| SCC5 | 248.5 | 13.9 | 77.7 | 90.5 | 57.7 | 352.1 |
| SCC8 | 292.0 | 4.0 | 26.1 | 11.9 | 8.8 | 48.7 |
| SCC9 | 1.4 | 3.6 | 34.4 | 14.1 | 4.2 | 15.8 |
| SCC10 | 261.4 | 4.0 | 15.7 | 1.5 | 11.9 | 9.6 |
| ADC1b | 76.6 | 13.1 | 82.3 | 21.3 | 12.2 | |
| ASCC1b | 131.6 | 6.7 | 43.4 | 66.6 | 1.9 | 144.1 |
| Tumor AM7277 Ambion | 382.8 | 2.5 | 57.8 | 47.9 | 1.4 | 84.4 |
| Normal AM7276 Ambion | 3.6 | 0.6 | 1.9 | 1.6 | 0.1 | 1.8 |
| normal#6 | 4.8 | 3.1 | 6.9 | 1.0 | 0.8 | 4.8 |
| normal#8 | 6.3 | 3.7 | 3.5 | 2.1 | 0.8 | 6.2 |
| normal#9 | 4.5 | 2.6 | 2.7 | 2.4 | 0.4 | 5.2 |
| normal#12 | 8.7 | 1.4 | 1.0 | 1.1 | 4.2 | 2.6 |

The expression patterns for the cell lines in this experiment was similar to the expression patterns in the tumors. CDKN2A showed very high fold-changes in all SCC samples except for SCC9. SCC9 was further evaluated by immunohistological staining, and interestingly, the SCC9 sample was CDKN2A negative on the protein level. It is possible that SCC9 is HPV negative. MKI67, TOP2A, and MCM5 also showed high fold-changes in many of the tumor specimens.

There was a divergence in the results between the two CIN1 samples in this experiment. Because the CIN samples originate from biopsies without further micro-dissection, it is possible that the samples contain differing amounts of normal cells.

In this experiment, VEGFC, TERT, PIK3CA, POU4F1, and IGF2BP3 showed low to absent expression in all tumor an normal samples. Interestingly, IGF2BP3 was only detected in tumor samples, although with very high Ct values, and not in any of the normal samples.

Figure 3:
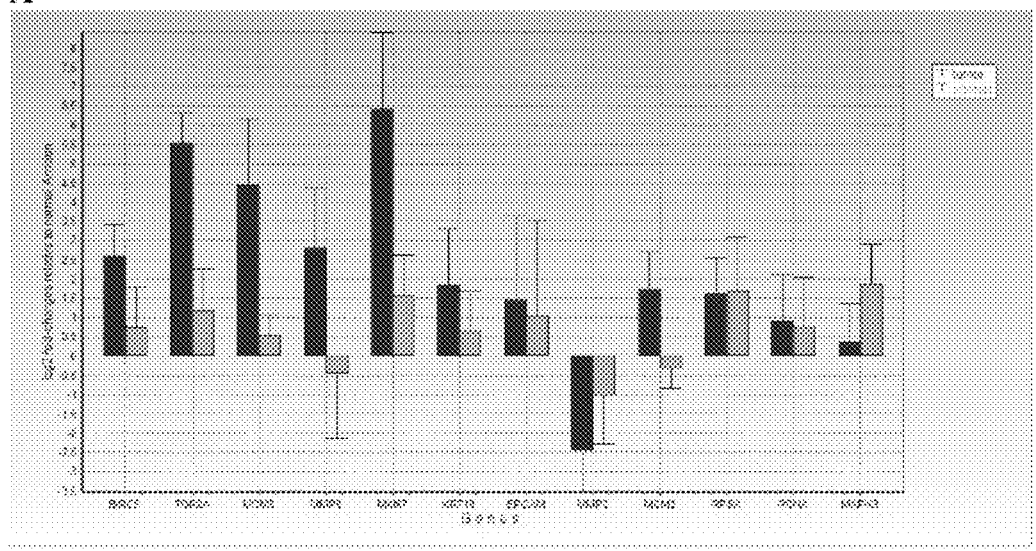
FIGS. 3A and 3B show the log 2 fold-changes±SD of certain mRNAs in tumor and normal samples relative to the Ambion normal sample, as discussed in Example 4. For each pair of bars, the left bar represents tumor samples and the right bar represents normal samples.
Figure 3:
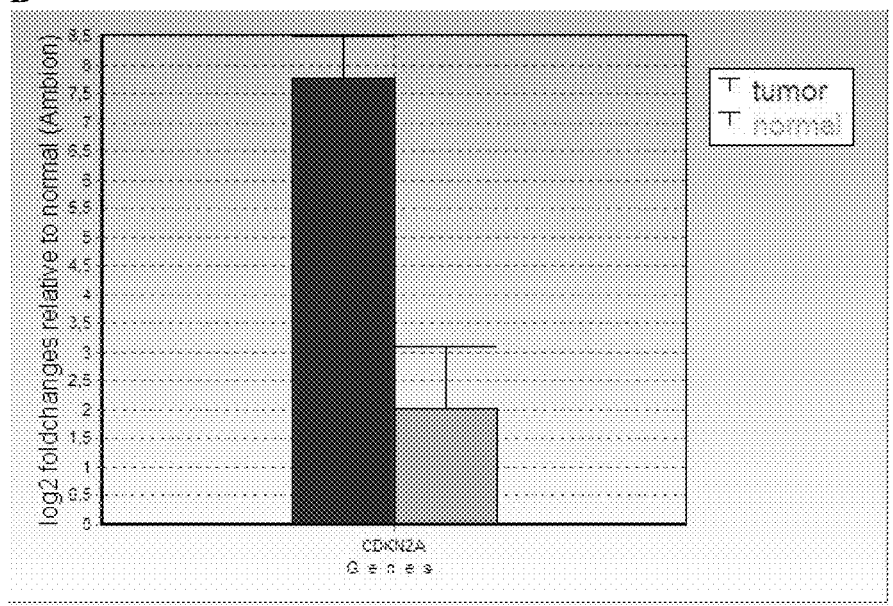

Log 2 fold-change in expression values relative to the Ambion normal sample were plotted for all tumor samples, except for CIN samples, and for all of the normal samples. Those results are shown in FIGS. 3A and 3B. Error bars represent standard deviation (SD).

Statistical Analysis.

Tumor samples (n=10) and normal samples (n=6) were further analysed for significant differences in relative expression levels, using the t-test. Because SCC9 alone among tumor samples did not appear to express CDKN2A, SCC9 was excluded in the t-test. All genes fulfilled the normal distribution criteria for the t-test to be valid. The results are shown in Table 25.

TABLE 24

Fold-changes in expression levels: Clinical samples vs. normal#1 (Ambion)

| Tissue samples | KRT19 | EPCAM | MMP2 | MCM2 | RPSA | PCNA | MAPK3 |
|---|---|---|---|---|---|---|---|
| CIN1#1 | 1.1 | 0.8 | 0.02 | 1.5 | 6.2 | 1.7 | 0.9 |
| CIN1#2 | 2.8 | 3.2 | 0.26 | 0.3 | 4.9 | 1.3 | 1.8 |
| CIN2#1 | 1.4 | 1.0 | 0.23 | 0.3 | 3.1 | 2.4 | 3.3 |
| SCC1c | 2.8 | 1.8 | 0.09 | 4.7 | 4.6 | 1.7 | 0.8 |
| SCC3b | 2.2 | 2.7 | 0.30 | 4.5 | 2.8 | 4.4 | 1.4 |
| SCC4b | 4.7 | 17.6 | 0.41 | 5.2 | 3.6 | 1.0 | 2.2 |
| SCC5 | 4.6 | 2.5 | 0.09 | 10.7 | 4.6 | 2.1 | 1.9 |
| SCC8 | 7.5 | 1.6 | 0.32 | 2.1 | 3.3 | 1.2 | 0.5 |
| SCC9 | 11.9 | 0.9 | 0.08 | 1.7 | 5.6 | 0.8 | 0.7 |
| SCC10 | 5.0 | 1.6 | 0.39 | 1.0 | 6.0 | 8.1 | 2.4 |
| ADC1b | 2.7 | 31.8 | 0.38 | 2.6 | 1.5 | 1.6 | 3.8 |
| ASCC1b | 7.5 | 9.5 | 0.16 | 4.9 | 2.8 | 4.4 | 0.6 |
| Tumor AM7277 Ambion | 0.3 | 0.1 | 0.07 | 3.3 | 0.7 | 0.6 | 1.6 |
| Normal AM7276 Ambion | 0.5 | 1.2 | 0.11 | 1.2 | 1.4 | 0.4 | 3.0 |
| normal#6 | 1.5 | 0.3 | 0.39 | 0.5 | 4.4 | 2.8 | 3.8 |
| normal#8 | 2.0 | 0.9 | 0.40 | 0.7 | 2.2 | 2.8 | 7.6 |
| normal#9 | 4.2 | 32.5 | 0.60 | 1.0 | 10.5 | 3.6 | 6.2 |
| normal#12 | 2.3 | 7.2 | 1.31 | 0.6 | 8.0 | 2.3 | 4.3 |

TABLE 25

Statistical (t-test) analysis of expression data - tumor vs. normal

| gene | expression pattern | p-value |
|---|---|---|
| CDKN2A | tumor > normal | 0.000000012 |
| BIRC5 | tumor > normal | 0.0015591 |
| TOP2A | tumor > normal | 0.0000002 |
| MCM5 | tumor > normal | 0.0000901 |
| MMP9 | tumor > normal | 0.0015077 |
| MKI67 | tumor > normal | 0.0000787 |
| KRT19 | | 0.1037645 NS |
| EPCAM | | 0.7343875 NS |
| MMP2 | tumor < normal | 0.0315609 |
| MCM2 | tumor > normal | 0.0002907 |
| RPSA | | 0.8822517 NS |
| PCNA | | 0.8408861 NS |
| MAPK3 | tumor < normal | 0.0116822 |

NS = not significant

In this experiment, expression levels of CDKN2A, MKI67, TOP2A, and MCM5 were clearly elevated, and that elevation was statistically significant. Increased expression of at least those four mRNAs, and possibly others, correlate with tumors.

5.5 Example 5: mRNA Expression in Liquid PAP Specimens

Materials and Methods

Samples.

Three to six week old clinical liquid PAP specimens in PreservCyt transport media (Cytec) were used in this study. Four mL of each cell suspension was centrifuged at 2200×g for 15 minutes. The cell pellet was mixed with 700 µL QIAzol lysis reagent (Qiagen; Hilden, Germany). Total RNA was extracted using miRNeasy RNA extraction kit (Qiagen; Hilden, Germany), according to manufacturer's protocol. The RNA concentration of each sample was measured with a NanoDrop instrument (Thermo Scientific; Wilmington, Del.).

cDNA Synthesis.

Reverse transcription was performed using 10 µL total RNA (0.1-0.5 µg) in a 20 µL reaction volume using random hexamers and the High Capacity cDNA RT kit (Applied Biosystems, Inc.; Foster City, Calif.) according to manufacturer's protocol. In parallel, the same reactions were performed without the reverse transcriptase for no RT controls.

Selection of Reference mRNAs and Target mRNAs.

ACTB, GAPDH and TBP were selected as references for this experiment. CDKN2A and MKI67 were selected as target mRNAs.

PCR Reactions.

All PCR reactions were performed in triplicate in a 25 µL reaction volume on a Stratagene MX3000p instrument using a cDNA concentration corresponding to about 2 ng total RNA/reaction. TaqMan® Universal PCR Master Mix (Applied Biosystems, Inc; Foster City, Calif.) was used for all reactions. Primer and probe sequences, concentrations and thermal cycling conditions were the same as discussed in Example 4. All probes were FAM-labeled and all reactions were run in singleplex.

Expression Analysis.

GenEx 4.4.2 software (multiD analysis, Gothenburg, Sweden) to analyse relative expression. The GenEx software uses the ΔΔCt formula, compensating for differences in PCR efficiency.

Results

Figure 4:
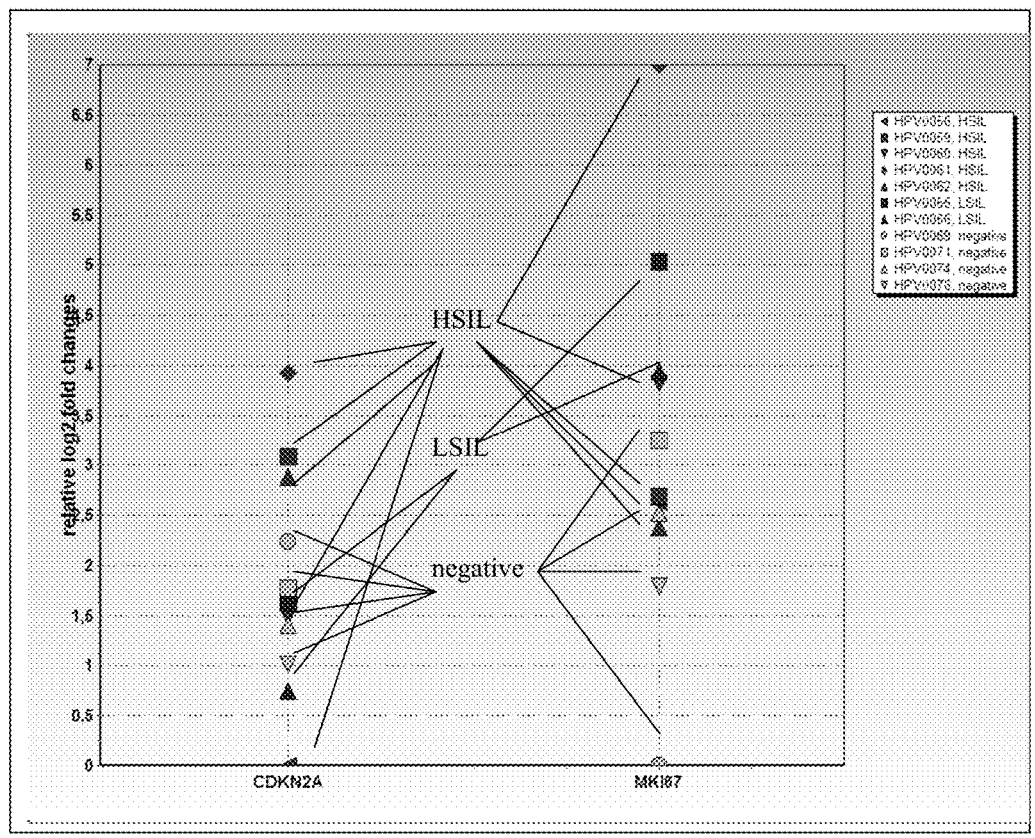
FIG. 4 shows relative log 2 fold changes of certain mRNAs in liquid PAP samples, as discussed in Example 5.

Total RNA yield varied between 0.3 µg-4 µg. Four of the samples yielded insufficient concentrations of RNA to be used for cDNA synthesis. Ten out of twenty-one cDNAs were further analyzed for mRNA expression; the remaining samples resulted in Ct values that were too high to be reliable. Ct values for the analyzed samples are shown in Table 26. The relative log 2 fold-changes are plotted in FIG. 4.

TABLE 26

| | Ct values | | | | |
|---|---|---|---|---|---|
| Sample ID | ACTB | GAPDH | TBP | CDKN2A | MKI67 |
| HPV0056, HSIL | 24.19 | 26.21 | 33.73 | 31.37 | 34.53 |
| | 24.16 | 26.28 | 34.31 | 31.3 | 34.16 |
| | 24.46 | 26.46 | 33.58 | 31.14 | 34.72 |
| HPV0059, HSIL | 24.79 | 27.20 | 35.30 | 28.9 | 35.14 |
| | 24.54 | 27.42 | 35.18 | 29.18 | 35.2 |
| | 25.03 | 27.24 | 35.27 | 28.99 | 35.74 |
| HPV0060, HSIL | 25.38 | 24.92 | 31.75 | 28.91 | 32.41 |
| | 25.63 | 25.10 | 31.67 | 28.95 | 32.31 |
| | 25.65 | 25.13 | 31.59 | 29.09 | 32.76 |
| HPV0061, HSIL | 25.88 | 25.98 | 31.69 | 26.98 | 29.68 |
| | 25.79 | 25.93 | 32.09 | 27.01 | 29.52 |
| | 26.05 | 25.91 | 31.93 | 26.89 | 29.86 |
| HPV0062, HSIL | 25.64 | 28.14 | 33.87 | 29.61 | 36.34 |
| | 25.48 | 28.05 | 35.43 | 29.56 | 35.64 |
| | 25.86 | 28.10 | 34.76 | 29.66 | 36.16 |
| HPV0065, LSIL | 29.72 | 28.07 | 35.75 | 32.44 | 34.86 |
| | 29.62 | 27.87 | 35.92 | 32.22 | 34.98 |
| | 30.01 | 27.82 | 34.90 | 32.84 | 34.82 |
| HPV0066, LSIL | 27.17 | 27.72 | 35.23 | 32.41 | 35.27 |
| | 27.29 | 27.56 | 34.97 | 32.18 | 35.21 |
| | 27.31 | 27.67 | 35.02 | 32.41 | 34.34 |
| HPV0069, negative | 26.56 | 29.05 | 34.97 | 31.21 | No Ct |
| | 26.60 | 28.72 | 36.00 | 31.04 | 39.36 |
| | 26.97 | 28.88 | 35.15 | 31.11 | No Ct |
| HPV0071, negative | 28.32 | 29.21 | 34.89 | 31.9 | 36.69 |
| | 28.48 | 28.90 | 34.50 | 32.14 | 35.78 |
| | 28.70 | 29.17 | 34.69 | 32.07 | 36.8 |
| HPV0074, negative | 28.37 | 27.09 | 32.97 | 31.06 | 35.18 |
| | 28.60 | 27.02 | 32.74 | 31.05 | 36.25 |
| | 28.46 | 27.00 | 33.01 | 31.3 | 36.26 |
| HPV0078, negative | 28.90 | 29.19 | 34.03 | 32.78 | 38.61 |
| | 28.91 | 29.16 | 34.63 | 32.94 | 36.39 |
| | 28.93 | 29.29 | 34.61 | 33.03 | 39.07 |

LSIL = low grade squamous intraepithelial lesion
HSIL = high grade squamous intraepithelial lesion This experiment demonstrates that mRNA expression markers can be detected in liquid PAP specimens.

5.6 Example 6: Microrna Detection in Clinical Samples by RT-PCR

Materials and Methods

Samples.

Total RNA from normal cervix was purchased from Applied Biosystems, Inc. (Foster City, Calif.; ABI AM 6992; "Ambion sample"). Total RNA from cervical tumor and normal specimens were prepared as in Example 3.

MicroRNAs Selected for Analysis.

miR-21 was analyzed for each of the samples shown in Table 27. miR-1290 was analyzed for a subset of the samples, as shown in Table 27. RNU44, U47, and RNU48 were used for normalization.

TABLE 27

RNA samples and microRNAs selected for expression analysis

| Sample name | Sample description | miR-21 | miR-1290 |
|---|---|---|---|
| SCC-1c | Frozen | x | x |
| SCC-3b | Frozen | x | x |
| SCC-4b | Frozen | x | x |
| SCC-5 | Frozen | x | x |
| SCC-8 | Frozen | x | x |
| SCC-9 | Frozen | x | x |
| SCC-10 | Frozen | x | x |
| SCC-11 | Frozen | | x |
| SCC-12 | Frozen | | x |
| SCC-13 | FFPE | | x |
| SCC-14 | FFPE | | x |
| SCC-15 | FFPE | | x |
| SCC-16 | FFPE | | x |
| SCC-17 | FFPE | | x |
| ASCC-1b | Frozen | x | |
| AIS-1 | FFPE | | x |
| AIS-2 | FFPE | | x |
| ADC-1b | Frozen | x | |
| ADC-2 | FFPE | | x |
| ADC-3 | FFPE | | x |
| ADC-4 | FFPE | | x |
| CIN3-2 | FFPE | x | |
| cx-normal-6 | Frozen | x | |
| cx-normal-8 | Frozen | x | |
| cx-normal-9 | Frozen | x | |
| cx-normal-12 | Frozen | x | x |
| cx-normal-13 | Frozen | | x |
| cx-normal-14 | Frozen | | x |
| cx-normal-15 | Frozen | | x |
| cx-normal-16 | Frozen | | x |
| cx-normal-17 | Frozen | | x |
| cx-normal-19 | Frozen | | x |
| cx-normal-20 | Frozen | | x |
| normal Ambion | ABI frozen | x | x |
| hyperplasia-1 (benign) | Frozen | | x |

SCC = Squamous Cervical Carcinoma, ADC = Cervical Adenocarcinoma, ASCC = Adeno-Squamous Cervical Carcinoma, AIS = Adenocarcinoma in situ RT-PCR Reactions.

All microRNA RT-PCR assays were purchased from Applied Biosystems Inc (Foster City, Calif.), including those for normalization genes. The cDNA synthesis and PCR reactions were performed according to manufacturer's protocols. All PCR reactions were run on an MX3000 instrument (Stratagene).

Expression Analysis.

For the analysis of relative expression, the GenEx 4.4.2 software (multiD analysis, Gothenburg, Sweden) was used. The GenEx software uses the ΔΔCt formula, compensating for differences in PCR efficiency. The GenEx statistical module was used for t-test analysis.

Results

Figure 5:
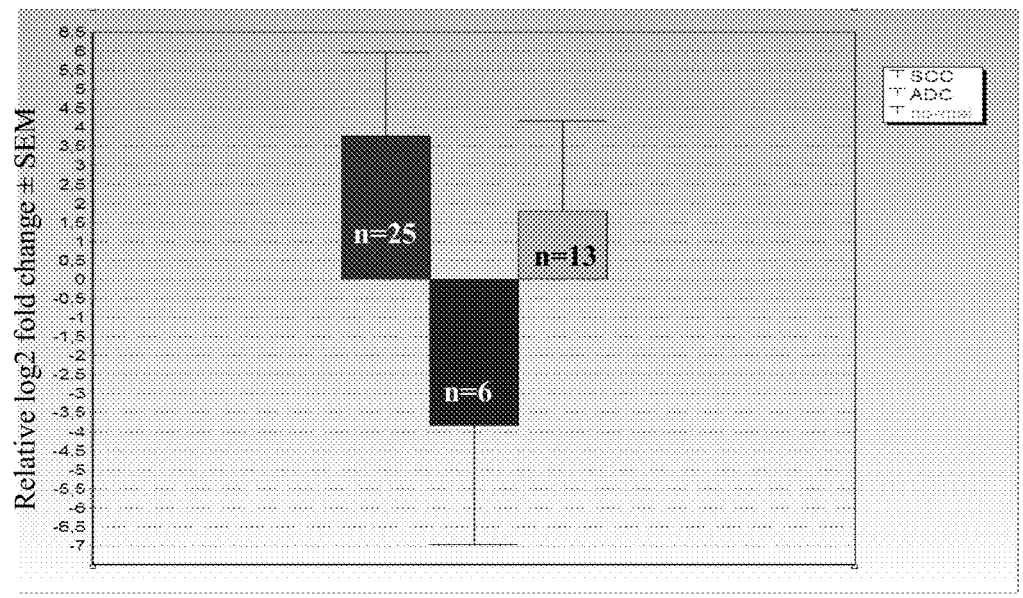
FIG. 5 shows relative log 2 fold changes±SD of miR-205 in cervical tumor samples and normal tissue, as discussed in Example 6. The left bar represents SCC samples, the middle bar represents ADC samples, and the right bar represents normal samples.
Figure 6:
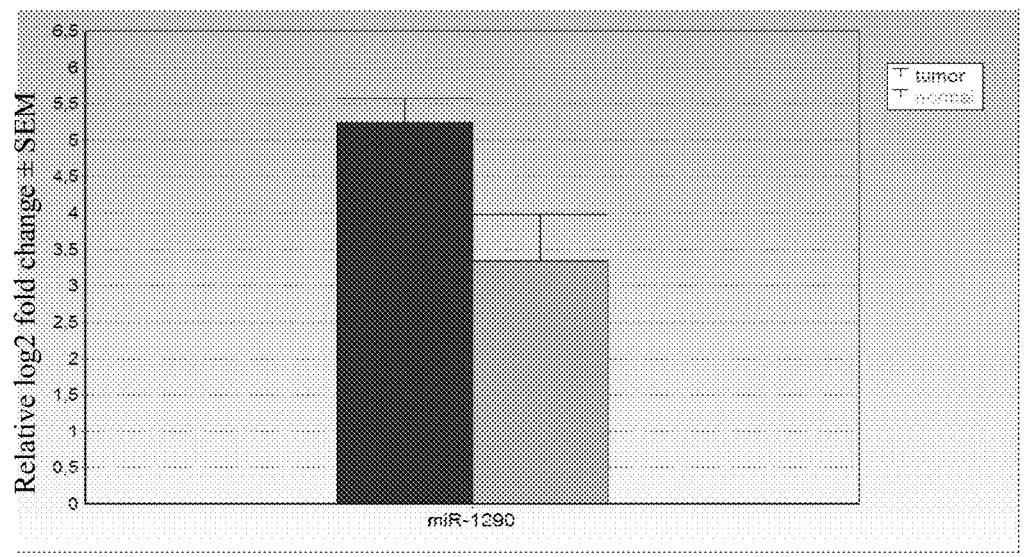
FIG. 6 shows relative log 2 fold changes±SD of miR-1290 in cervical tumor samples and normal tissue, as discussed in Example 6. The left bar represents tumor samples and the right bar represents normal samples.

MiR-205 and miR-1290 show a statistically significant difference in expression levels between tumor and normal samples. See FIGS. 5 and 6. Interestingly, miR-205 is markedly down-regulated in adeno-carcinoma specimens, which originate from glandular endothelial cells, while it is upregulated in squamous carcinoma specimens, which are derived from epithelial cells. This result is consistent with reports discussing other forms of cancer, such as lung cancer.

These results demonstrate that RT-PCR can be used to detect increases in expression of microRNAs in cervical specimens.

5.8 Example 7: Bioinformatic Analysis to Identify microRNAs

In order to identify the microRNAs detected with the probes shown, e.g., in Tables 1 and 11, small RNA sequencing (smRNASeq) datasets were analysed using the probe sequences to identify expressed microRNAs detected by those sequences. The analysis identified 44 sequences with precise ends, corresponding to 37 arms (i.e., some of the sequences appear to be isomirs, or multiple candidate microRNAs from a single arm). Those 44 candidate microRNA sequences are show in Table 28.

TABLE 28 microRNA candidate sequences corresponding to probes

| Arm name | microRNA candidate sequence 5' -> 3' | SEQ ID |
|---|---|---|
| 12726-L | TCCCCCAACCCACAGCACACAC | 345 |
| 12730-R | CCCGGAGAGCGGAGCACAACACA | 346 |
| 12730-R | CCGGAGAGCGGAGCACAAC | 347 |
| 13108-L | CCAAGGAAGGCAGCAGGC | 348 |
| 13122-L | GATGGAATTTCCTAAAGG | 349 |
| 13124-L | GGAGGGGAGGAGACATG | 350 |
| 13181-L | GCAGTGACTGTTCAGACGTCCA | 351 |
| 13207-R | TGTCTTTCCTTGTTGGAGCAGG | 352 |
| 13209-L | CAGCAGGCGAGTTACCTCAA | 353 |
| 13227-L | GAGGAGGACTGGGCCCTA | 354 |
| 13229-R | AGCCGCTCTTCTCCCTGCCCACA | 355 |
| 13229-R | AGCCGCTCTTCTCCCTGCCCACAG | 356 |
| 13231-L | TGGGGAGCGGCCCCCGGG | 357 |
| 13247-L | GAGGTCGGGAGGGGAAGGCGGCT | 358 |
| 13252-L | TCAAGGAGCTCACAGTC | 359 |
| 13254-R | GCATGAGTGGTTCAGTGGT | 360 |
| 13267-L | GTGGGCTGGGCTGGGCTGGGC | 361 |
| 13274-L | GGAGGACCCTGAGGGAGGGTGGG | 362 |
| 13274-L | TGAGGGAGGGTGGGAGC | 363 |
| 13283-L | TGGCAGCAAGGAAGGCAGGGGTC | 364 |
| 13291-L | GAGGGAAGGAGGGAGGAA | 365 |
| 13296-L | CAGGGCAGAGGGCACAGGAATCTGA | 366 |
| 13325-R | GGGAAGAGCCCAGCGCC | 367 |
| 13339-L | ACCCTCAGTCCGTATTGGTCTCT | 368 |
| 13504-R | GTCTCCCAGAGCAGGGACGCTTT | 369 |
| 25-R | TTAGAAAAAGAGGGGGTGAGG | 370 |
| 3371-L | TGGGGTGTGGAGGGGAGG | 371 |
| 3744-R | AGGGGAGCAGGGAGGAA | 372 |
| 3995-L | TGGCCTGACGTGAGGAGGAGG | 373 |

TABLE 28-continued microRNA candidate sequences corresponding to probes

| Arm name | microRNA candidate sequence 5' -> 3' | SEQ ID |
|---|---|---|
| 4417-R | ACGGACAGGGAACTTTTTGAT | 374 |
| 4440-L | GCCCAGTGCTCTGAATGTCAAA | 375 |
| 4440-L | TCTGCCCAGTGCTCTGAATGTCA | 376 |
| 4440-R | GGCGGGAGTAACTATGAC | 377 |
| 4440-R | CGGGTAAACGGCGGGAGTAACT | 378 |
| 4498-L | AGCAGGCGCACGGCCGTCTGGATC | 379 |
| 4498-L | GCACGGCCGTCTGGATCTCC | 380 |
| 5192-L | GAGGAAGGAAGGGGAAA | 381 |
| 6216-L | CAGTGCTCTGAATGTCAAAGTGAAGA | 382 |
| 6216-R | GGGTAAACGGCGGGAGTA | 383 |
| 6235-R | AAATGGATTTTTGGAGCAG | 384 |

TABLE 28-continued microRNA candidate sequences corresponding to probes

| Arm name | microRNA candidate sequence 5' -> 3' | SEQ ID |
|---|---|---|
| 6930-R | TGCAAGATCAGAGGGGAGA | 385 |
| 7578-L | GGGGCTGTAGCTCAGGG | 386 |
| 8339-R | GCCGGTACAGTGAAAAT | 387 |
| 8339-R | GCCGGTACAGTGAAAATG | 388 |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that changes can be made without departing from the spirit and scope of the invention(s).

What is claimed is:

1. A method comprising:
    detecting a level of at least one target RNA in a cervical sample from a human subject, wherein at least one target RNA is miR-1290, wherein miR-1290 comprises the sequence of SEQ ID NO.: 390, wherein the detecting comprises:
    (i) hybridizing nucleic acids derived from the sample with at least one polynucleotide comprising a sequence that is identical or fully complementary to at least 15 contiguous nucleotides of SEQ ID NO: 209; and
    (ii) detecting the presence of a complex comprising the polynucleotide hybridized to at least one nucleic acid selected from miR-1290 RNA, a DNA amplicon of miR-1290 RNA, and a complement of miR-1290 RNA; and
    wherein the at least one target RNA consists of 1 to 8 target RNAs.

2. The method of claim 1, wherein the at least one polynucleotide comprises the sequence SEQ ID NO: 209.

3. The method of claim 1, wherein the method further comprises isolating nucleic acids from the cervical sample.

4. The method of claim 3, wherein the nucleic acids comprise RNA that has been separated from DNA.

5. The method of claim 1, wherein the detecting miR-1290 in the sample is performed using real-time quantitative RT-PCR.

6. The method of claim 1, wherein the cervical sample is a sample of cervical cells obtained by routine Pap smear.

* * * * *